US009975927B2

(12) United States Patent
Lundberg et al.

(10) Patent No.: US 9,975,927 B2
(45) Date of Patent: May 22, 2018

(54) MUTANT FRAGMENTS OF OSPA AND METHODS AND USES RELATING THERETO

(71) Applicant: Valneva Austria GmbH, Vienna (AT)

(72) Inventors: Urban Lundberg, Pressbaum (AT); Wolfgang Schüler, Vienna (AT)

(73) Assignee: Valneva Austria GmbH, Vienna (AT)

( * ) Notice: Subject to any disclaimer, the term of this patent is extended or adjusted under 35 U.S.C. 154(b) by 0 days. days.

(21) Appl. No.: 15/110,151

(22) PCT Filed: Jan. 9, 2015

(86) PCT No.: PCT/EP2015/050365
§ 371 (c)(1),
(2) Date: Jul. 7, 2016

(87) PCT Pub. No.: WO2015/104396
PCT Pub. Date: Jul. 16, 2015

(65) Prior Publication Data
US 2016/0333056 A1    Nov. 17, 2016

(30) Foreign Application Priority Data

Jan. 9, 2014   (EP) .................................... 14150682

(51) Int. Cl.
| | | |
|---|---|---|
| C07K 14/20 | (2006.01) | |
| A61K 39/02 | (2006.01) | |
| C07K 16/12 | (2006.01) | |
| A61K 39/39 | (2006.01) | |
| A61K 39/00 | (2006.01) | |

(52) U.S. Cl.
CPC .......... *C07K 14/20* (2013.01); *A61K 39/0225* (2013.01); *A61K 39/39* (2013.01); *C07K 16/1207* (2013.01); *A61K 2039/55516* (2013.01); *A61K 2039/70* (2013.01); *C07K 2317/24* (2013.01); *C07K 2317/33* (2013.01); *C07K 2319/00* (2013.01); *C07K 2319/21* (2013.01)

(58) Field of Classification Search
None
See application file for complete search history.

(56) References Cited

U.S. PATENT DOCUMENTS

| | | | |
|---|---|---|---|
| 6,248,562 B1 | 6/2001 | Dunn et al. | |
| 8,986,704 B2* | 3/2015 | Comstedt | A61K 39/02 424/184.1 |
| 2004/0023325 A1 | 2/2004 | Luft et al. | |
| 2011/0293652 A1 | 12/2011 | Crowe et al. | |
| 2014/0010835 A1* | 1/2014 | Comstedt | A61K 39/02 424/190.1 |
| 2017/0101446 A1* | 4/2017 | Comstedt | A61K 39/02 |

FOREIGN PATENT DOCUMENTS

| | | |
|---|---|---|
| WO | WO 2008/031133 A2 | 3/2008 |
| WO | WO 2011/143617 A1 | 11/2011 |
| WO | WO 2011/143623 A1 | 11/2011 |
| WO | WO 2012/066420 A1 | 5/2012 |
| WO | WO 2012/066423 A1 | 5/2012 |
| WO | WO 2014/006226 A1 | 1/2014 |

OTHER PUBLICATIONS

Dykhuizen et al. 1993 (Borrelia burgdorferi is clonal: Implications for taxonomy and vaccine development; Proc. Natl. Acad. Sci. 90: 10163-10167).*
Baker et al., Electrostatics of nanosystems: application to microtubules and the ribosome. Proc Natl Acad Sci U S A. Aug. 28, 2001;98(18):10037-41.
Bessler et al., Synthetic lipopeptides as novel adjuvants. Res Immunol. Jun. 1992;143(5):548-53; discussion 579-80.
Betz, Disulfide bonds and the stability of globular proteins. Protein Sci. Oct. 1993;2(10):1551-8.
Bouchon et al., Analysis of the lipidated recombinant outer surface protein A from Borrelia burgdorferi by mass spectrometry. Anal Biochem. Mar. 1, 1997;246(1):52-61.
Caruthers et al., New chemical methods for synthesizing polynucleotides. Nucleic Acids Symp Ser. 1980;(7):215-23.
Comstedt et al., Design and development of a novel vaccine for protection against Lyme borreliosis. PLoS One. Nov. 19, 2014;9(11):e113294. doi: 10.1371/journal.pone.0113294.
Comstedt et al., Efficacy testing of a novel OspA based Lyme borreliosis vaccine. Jan. 19-24, 2014. Gordon Research Conference: Biology of Spirochetes. Abstract.
Comstedt et al., Investigation of a vaccine targeting Lyme borreliosis in Europe. Jan. 19-24, 2014. Gordon Research Conference: Biology of Spirochetes. Abstract.
Creighton et al., Mechanisms and catalysts of disulfide bond formation in proteins. Trends Biotechnol. Jan. 1995;13(1):18-23.
Crowe, A Lyme Borreliosis Vaccine for Europe and beyond. Baxter Innovations GmbH. Feb. 6, 2009.
Ding et al., Structural identification of a key protective B-cell epitope in Lyme disease antigen OspA. J Mol Biol. Oct. 6, 2000;302(5):1153-64.

(Continued)

*Primary Examiner* — Mary Maille Lyons
(74) *Attorney, Agent, or Firm* — Wolf, Greenfield & Sacks, P.C.

(57) ABSTRACT

The present invention relates to compositions and methods for the prevention and treatment of *Borrelia* infection. Particularly, the present invention relates to a polypeptide comprising a hybrid C-terminal fragment of an outer surface protein A (OspA), a nucleic acid coding the same, an antibody specifically binding the same, a pharmaceutical composition (particularly for use as a medicament or in a method of treating or preventing a *Borrelia* infection) comprising the polypeptide and/or the nucleic acid and/or the antibody, a method of treating or preventing a *Borrelia* infection and a method of immunizing a subject.

11 Claims, 6 Drawing Sheets

(56) References Cited

OTHER PUBLICATIONS

Dolinsky et al., PDB2PQR: expanding and upgrading automated preparation of biomolecular structures for molecular simulations. Nucleic Acids Res. Jul. 2007;35(Web Server issue):W522-5.

Fass, Disulfide bonding in protein biophysics. Annu Rev Biophys. 2012;41:63-79. doi: 10.1146/annurev-biophys-050511-102321.

Friguet et al., Measurements of the true affinity constant in solution of antigen-antibody complexes by enzyme-linked immunosorbent assay. J Immunol Methods. Mar. 18, 1985;77(2):305-19.

Gern et al., Immunization with a polyvalent OspA vaccine protects mice against Ixodes ricinus tick bites infected by Borrelia burgdorferi ss, Borrelia garinii and Borrelia afzelii. Vaccine. Oct. 1997;15(14):1551-7.

Golde et al., Reactivity with a specific epitope of outer surface protein A predicts protection from infection with the Lyme disease spirochete, Borrelia burgdorferi. Infect Immun. Mar. 1997;65(3):882-9.

Hertadi et al., Unfolding mechanics of multiple OspA substructures investigated with single molecule force spectroscopy. J Mol Biol. Nov. 7, 2003;333(5):993-1002.

Horn et al., Synthesis of oligonucleotides on cellulose. Part II: Design and synthetic strategy to the synthesis of 22 oligodeoxynucleotides coding for gastric inhibitory polypeptide (GIP). Nucleic Acids Symp Ser. 1980;(7):225-32.

Kiefer et al., The SWISS-MODEL Repository and associated resources. Nucleic Acids Res. Jan. 2009;37(Database issue):D387-92. doi: 10.1093/nar/gkn750.

Koide et al., Multistep denaturation of Borrelia burgdorferi OspA, a protein containing a single-layer beta-sheet. Biochemistry. Apr. 13, 1999;38(15):4757-67.

Koide et al., Structure-based design of a second-generation Lyme disease vaccine based on a C-terminal fragment of Borrelia burgdorferi OspA. J Mol Biol. Jul. 8, 2005;350(2):290-9.

Li et al., Crystal structure of Lyme disease antigen outer surface protein A complexed with an Fab. Proc Natl Acad Sci U S A. Apr. 15, 1997;94(8):3584-9.

Liang et al., An immunodominant conserved region within the variable domain of VlsE, the variable surface antigen of Borrelia burgdorferi. J Immunol. Nov. 15, 1999;163(10):5566-73.

Lindgren et al., Lyme borreliosis in Europe: influences of climate and climate change, epidemiology, ecology and adaptation measures. World Health Organization Europe. 2006.

Livey et al., A new approach to a Lyme disease vaccine. Clin Infect Dis. Feb. 2011;52 Suppl 3:S266-70. doi: 10.1093/cid/ciq118.

Livey et al., Development of a novel lyme disease vaccine. The international conference on lyme borreliosis and other tick borne diseases. 2010. Poster.

Marshall et al., Safety and immunogenicity of a meningococcal B bivalent rLP2086 vaccine in healthy toddlers aged 18-36 months: a phase 1 randomized-controlled clinical trial. Pediatr Infect Dis J. Oct. 2012;31(10):1061-8.

Nissen et al., A randomized, controlled, phase 1/2 trial of a Neisseria meningitides serogroup B bivalent rLP2086 vaccine in healthy children and adolescents. Pediatr Infect Dis J. Apr. 2013;32(4):364-71. doi: 10.1097/INF.0b013e31827b0d24.

Pantoliano et al., High-density miniaturized thermal shift assays as a general strategy for drug discovery. J Biomol Screen. Dec. 2001;6(6):429-40.

Pronk et al., GROMACS 4.5: a high-throughput and highly parallel open source molecular simulation toolkit. Bioinformatics. Apr. 1, 2013;29(7):845-54. doi: 10.1093/bioinformatics/btt055.

Richmond et al., A bivalent Neisseria meningitidis recombinant lipidated factor H binding protein vaccine in young adults: results of a randomised, controlled, dose-escalation phase 1 trial. Vaccine. Sep. 21, 2012;30(43):6163-74. doi:10.1016/j.vaccine.2012.07.065.

Richmond et al., Safety, immunogenicity, and tolerability of meningococcal serogroup B recombinant lipoprotein 2086 vaccine in healthy adolescents: a randomised, single-blind, placebo-controlled, phase 2 trial. Lancet Infect Dis. Aug. 2012;12(8):597-607.

Roberge et al., A strategy for a convergent synthesis of N-linked glycopeptides on a solid support. Science. Jul. 14, 1995;269(5221):202-4.

Schwendinger et al., Evaluation of OspA vaccination-induced serological correlates of protection against Lyme borreliosis in a mouse model. PLoS One. Nov. 18, 2013;8(11):e79022. doi: 10.1371/journal.pone.0079022.

Steere et al., Vaccination against Lyme disease with recombinant Borrelia burgdorferi outer-surface lipoprotein A with adjuvant. Lyme Disease Vaccine Study Group. N Engl J Med. Jul. 23, 1998;339(4):209-15.

Van Hoecke et al., Evaluation of the safety, reactogenicity and immunogenicity of three recombinant outer surface protein (OspA) lyme vaccines in healthy adults. Vaccine. Dec. 1996;14(17-18):1620-6.

Wilske et al., An OspA serotyping system for Borrelia burgdorferi based on reactivity with monoclonal antibodies and OspA sequence analysis. J Clin Microbiol. Feb. 1993;31(2):340-50.

Yoder et al., Tripalmitoyl-S-glyceryl-cysteine-dependent OspA vaccination of toll-like receptor 2-deficient mice results in effective protection from Borrelia burgdorferi challenge. Infect Immun. Jul. 2003;71(7):3894-900.

\* cited by examiner

Fig. 2

```
                          1                                                  50
Lip-S4D1-S3hybD1    (1)   CSSFNAKGELSEKTILRANGTRLEYTEIKSDGTGKAKEVLKDFALEGTLA
   Lip-S4D1-S3D1    (1)   CSSFNAKGELSEKTILRANGTRLEYTEIKSDGTGKAKEVLKDFALEGTLA
       Consensus    (1)   CSSFNAKGELSEKTILRANGTRLEYTEIKSDGTGKAKEVLKDFALEGTLA
                          51                                                100
Lip-S4D1-S3hybD1   (51)   ADKTTLKVTCGTVVLSKHIPNSGEITVELNDSNSTQATKKTGKWDSNTST
   Lip-S4D1-S3D1   (51)   ADKTTLKVTCGTVVLSKHIPNSGEITVELNDSNSTQATKKTGKWDSNTST
       Consensus   (51)   ADKTTLKVTCGTVVLSKHIPNSGEITVELNDSNSTQATKKTGKWDSNTST
                          101                                               150
Lip-S4D1-S3hybD1  (101)   LTISVNSKKTKNIVFTKEDTITVQKYDSAGTNLEGNAVEIKTLDELCNAL
   Lip-S4D1-S3D1  (101)   LTISVNSKKTKNIVFTKEDTITVQKYDSAGTNLEGNAVEIKTLDELCNAL
       Consensus  (101)   LTISVNSKKTKNIVFTKEDTITVQKYDSAGTNLEGNAVEIKTLDELCNAL
                          151                                               200
Lip-S4D1-S3hybD1  (151)   KGTSDKNNGSGSKEKNKDGKYSFNEKGEVSEKILTRSNGTTLEYSQMTDA
   Lip-S4D1-S3D1  (151)   KGTSDKNNGSGSKEKNKDGKYSFNDKGKLSEKVVTRANGTRLEYTEIKND
       Consensus  (151)   KGTSDKNNGSGSKEKNKDGKYSFN KG  SEK   TR NGT LEY
                          201                                               250
Lip-S4D1-S3hybD1  (201)   ENATKAVETLKNGIKLPGNLVGGKTKLTVTCGTVTLSKNISKSGEITVAL
   Lip-S4D1-S3D1  (201)   G-SGKAKEVLKGFALEGTLTDGGETKLTVTCGTVTLSKNISKSGEITVAL
       Consensus  (201)        KA E LK         GG TKLTVTCGTVTLSKNISKSGEITVAL
                          251                                               300
Lip-S4D1-S3hybD1  (251)   NDTETTPADKKTGEWKSDTSTLTISKNSQKTKQLVFTKENTITVQNYNRA
   Lip-S4D1-S3D1  (250)   NDTETTPADKKTGEWKSDTSTLTISKNSQKPKQLVFTKENTITVQNYNRA
       Consensus  (251)   NDTETTPADKKTGEWKSDTSTLTISKNSQK KQLVFTKENTITVQNYNRA
                          301        322
Lip-S4D1-S3hybD1  (301)   GNALEGSPAEIKDLAELCAALK
   Lip-S4D1-S3D1  (300)   GNALEGSPAEIKDLAELCAALK
       Consensus  (301)   GNALEGSPAEIKDLAELCAALK
```

Fig. 3

A. Nucleic acid encoding a mutant OspA heterodimer polypeptide:

Non-native codons for cysteine

5'- [ Lipidation signal | CSS | Mutant OspA fragment | Linker (LN1) | Mutant OspA fragment ] -3'

↓ Translation

B. Intermediate polypeptide:

introduced disulfide bonds

NH2- [ lip signal | CSS | mutant OspA fragment | LN1 | mutant OspA fragment ] -COOH
         S⋯⋯S                              S⋯⋯S ↓ Post-translational modification C. Final lipidated polypeptide:

lip signal (Cleaved lipidation signal)

Lip- [ CSS | mutant OspA fragment | LN1 | mutant OspA fragment ]
           S⋯⋯S                              S⋯⋯S

Fig. 4

Lip-[CSS][ST1 OspA mutant][LN1][ST2 OspA mutant]

Lip-[CSS][ST4 OspA mutant][LN1][ST3 hyb OspA mutant]

Lip-[CSS][ST5 OspA mutant][LN1][ST6 OspA mutant]

Fig. 5

MUTANT FRAGMENTS OF OSPA AND METHODS AND USES RELATING THERETO

RELATED APPLICATION

This application is a national stage filing under 35 U.S.C. § 371 if international application PCT/EP2015/050365, filed Jan. 9, 2015, which was published under PCT Article 21(2) in English, the contents of which are incorporated by reference herein in its entirety.

FIELD OF THE INVENTION

The present invention relates to compositions and methods for the prevention and treatment of *Borrelia* infection. Particularly, the present invention relates to a polypeptide comprising a hybrid C-terminal fragment of an outer surface protein A (OspA), a nucleic acid coding the same, an antibody specifically binding the same, a pharmaceutical composition (particularly for use as a medicament or in a method of treating or preventing a *Borrelia* infection) comprising the polypeptide and/or the nucleic acid and/or the antibody, a method of treating or preventing a *Borrelia* infection and a method of immunizing a subject.

BACKGROUND OF THE INVENTION

Lyme borreliosis, or Lyme disease, is the most commonly reported tick-borne disease in Europe and North America. The disease is caused by infection with the arthropod-borne gram-negative-like spirochete, *Borrelia burgdorferi* sensu lato (*B. burgdorferi* s.l.), and can involve multiple organs or tissues, resulting in skin, cardiac, musculoskeletal and neurological disorders. In most countries, Lyme borreliosis is not a notifiable disease; therefore, exact data regarding annual incident rates are not available. In the United States, the causative agent is *B. burgdorferi* sensu stricto (*B. burgdorferi* s.s.) and Lyme borreliosis is localized to northeastern, mid-Atlantic and upper north-central states. In 2010, a total of about 30,000 cases of Lyme borreliosis were reported to the US to the Centers for Disease Control and Prevention (CDC). An updated report by the CDC in 2013, which takes into account diagnostic data from other sources, estimates that the actual number of new cases per year in the United States is closer to 300,000 (http://www.cdc.gov/media/releases/2013/p0819-lyme-disease.html). In Europe, *B. afzelii* and *B. garinii* are the main causative agents of Lyme borreliosis, as well as *B. burgdorferi* s.s. and *B. bavariensis*, which contribute to a lesser extent depending on the geographic location. The prevalence of Lyme borreliosis varies considerably in different European countries with an overall increased prevalence from west to east. In much of Europe, the number of reported cases of Lyme borreliosis has increased since the early 1990s (e.g., the Czech Republic, Estonia, Lithuania; see Lyme borreliosis in Europe, WHO report of 2006), and the geographic distribution of cases has also expanded.

*Borrelia* belongs to the family Spirochaetaceae, which is subdivided into the medically important genera *Treponema*, *Leptospira* and *Borrelia*. *B. burgdorferi* s.l. is a spiral-shaped, vigorously motile gram-negative bacterium, about 10-20 μm long and 0.2-0.5 μm wide, that grows under microaerophilic conditions. The spirochetal cell wall consists of a cytoplasmic membrane surrounded by peptidoglycan and several flagella and then by a loosely-associated outer membrane.

Lyme borreliosis generally occurs in stages characterized by different clinical manifestations, with remissions and exacerbations. Stage 1, early infection, consists of a localized infection of the skin, followed within days or weeks by stage 2, disseminated infection, and months to years later by stage 3, persistent infection. However, the infection is variable; some patients have only localized infections of the skin, while others display only later manifestations of the illness, such as arthritis. Different clinical syndromes of Lyme borreliosis are also caused by infection with diverse *B. burgdorferi* s.l. species. *B. burgdorferi* s.s. more often causes joint manifestations (arthritis) and heart problems, *B. afzelii* causes mainly dermal symptoms (erythema migrans; EM and acrodermatitis chronica atrophicans; ACA), whereas *B. garinii* is implicated in most cases of neuroborreliosis.

Localized infection—The most common symptom of stage 1 of an infection is erythema migrans, which occurs in 70-80% of infected people. This skin lesion is often followed by flu-like symptoms, such as myalgia, arthralgia, headache and fever. These non-specific symptoms occur in 50% of patients with erythema migrans.

Disseminated infection—During stage 2, the bacteria move into the blood stream from the site of infection to distal tissues and organs. Neurological, cardiovascular and arthritic symptoms that occur in this stage include meningitis, cranial neuropathy and intermittent inflammatory arthritis.

Persistent infection—Stage 3 of the infection is chronic and occurs from months to years after the tick bite. The most common symptom in North America is rheumatoid arthritis, caused by an infection with *B. burgdorferi* s.s. Persistent infection of the central nervous system with *B. garinii* causes more severe neurological symptoms during stage 3, and a persistent infection of the skin with *B. afzelii* results in acrodermatitis chronica atrophicans.

In some risk groups, such as farmers, forestry workers, hikers, runners or vacationers, seroprevalence and disease incidence rates have increased, as well as in children under 15 years of age and adults between 39 and 59, without gender preference. This increased incidence of Lyme borreliosis is linked to changes in forest habitats as well as social factors. Environmental changes, such as forest fragmentation, have led to a sharp reduction of rodent predators such as foxes and birds of prey, which in turn has led to an increase in the mouse population, with a subsequent increase in the tick population. More recently, patchy reforestation has increased the number of deer and thus the number of ticks. Suburban sprawl and the increasing use of woodland areas for recreation such as camping and hiking has brought humans into greater contact with the larger number of tick *Borrelia* vectors. All of these factors together have contributed to a wider distribution of *Borrelia* and a higher incidence of Lyme borreliosis.

Antimicrobial agents are the principle method of treatment of *Borrelia* infection. The antibiotic used depends on the stage of the disease, symptoms, and the patient's allergies to medication. The length of the antibiotic course also depends on the stage of the disease and the severity of symptoms. Early Lyme borreliosis is typically treated with oral tetracyclines, such as doxycycline, and semi-synthetic penicillins, such as amoxicillin or penicillin V. Arthritic and neurological disorders are treated with high-dose intravenous penicillin G or ceftriaxone. Up to 30% of Lyme borreliosis patients do not display the early characteristic symptoms of infection with *Borrelia*, making diagnosis and treatment problematic. The antibiotic course can be long (up to several months) and sometimes ineffective and is thus debated in the *Borrelia* field, especially during later-stage disease. Even in the case of effective treatment of *Borrelia*, patients can be left with debilitating fatigue, pain, or neurological symptoms for years afterwards, which is referred to as post-treatment Lyme disease syndrome. In general, the use of antibiotics can have undesirable consequences, such as the development of resistance by the target micro-organisms. Finally, antibiotic therapy may effectively cure Lyme borreliosis, but provides no protection against subsequent infections.

A monovalent serotype 1-OspA-based vaccine (LYMErix™) was approved and marketed in the USA for the prevention of Lyme disease caused by *Borrelia burgdorferi* s.s., but the vaccine is no longer available. Furthermore, heterogeneity in OspA sequences across different serotypes in Europe and elsewhere precludes efficient protection with a vaccine based on OspA from only a single serotype.

Chimeric OspA molecules comprising the proximal portion from one OspA serotype, together with the distal portion form another OspA serotype, while retaining antigenic properties of both of the parent polypeptides, may be used in the prevention and treatment of Lyme disease or borreliosis (WO2011/143617, WO2011/143623).

Currently, there is no preventative medicament for Lyme borreliosis on the market and thus there is a need in the art for the development of such a medicament that can provide effective protection against *Borrelia* that are present in the USA, Europe and elsewhere, especially for the development of a medicament that can provide effective protection against several *Borrelia* serotypes simultaneously. The serotype 3 OspA-containing heterodimer, Lip-S4D1-S3hybD1, of the current invention improves on our previously-disclosed heterodimer, Lip-S4D1-S3D1 (see WO2014/006226) with regard to both ease of production and stimulation of specific antibodies as measured by antibody surface binding to serotype 3 *Borrelia* spirochetes. Additionally, the more specific quality of the immune response to the new heterodimer indicates that the potency is also superior in comparison to the previously-disclosed heterodimer.

SUMMARY OF THE INVENTION

The present invention relates to a polypeptide comprising a hybrid fragment of *Borrelia* outer surface protein A (OspA), a nucleic acid encoding the same, a vector which comprises such nucleic acid molecule, and a host cell comprising such vector. Furthermore, the invention provides a process for producing such polypeptide and a process for producing a cell which expresses such polypeptide. Moreover, the present invention provides antibodies specifically binding to such polypeptide, a hybridoma cell producing such antibodies, methods for producing such antibodies, a pharmaceutical composition comprising such polypeptide, nucleic acid molecule, vector or antibody, the use of such polypeptide, nucleic acid molecule, vector or antibody for the preparation of a medicament or a pharmaceutical composition (particularly for use as a vaccine or in a method of treating or preventing a *Borrelia* infection), methods for diagnosing an infection and methods for treating or preventing a *Borrelia* infection and methods of immunizing a subject. In particular, the invention relates to an improved polypeptide for immunization against serotype 3 *Borrelia*, in that the polypeptide is more favourable for purification and induces a more specific immune response to *Borrelia* as assessed by surface binding to *Borrelia* when compared with the serotype 3 OspA-containing construct disclosed in our previous application WO2014/006226.

Efforts to develop a subunit vaccine for prevention of Lyme borreliosis have been focused in large part on the use of borrelial outer surface protein A (OspA) as an antigen. The OspA protein is expressed by *Borrelia* only when it is in the gut of the tick vector. Thus, OspA antibodies produced by vaccination do not fight infection in the body, but rather enter the gut of the tick when it takes a blood meal. There, the antibodies neutralise the spirochetes and block the migration of bacteria from the midgut to the salivary glands of the tick, the route through which *Borrelia* enters the vertebrate host. Thus, OspA-specific antibodies prevent the transmission of *Borrelia* from the tick vector to the human host.

The lipidated form of OspA from *B. burgdorferi* s.s., strain ZS7, together with aluminium hydroxide was commercially developed as a vaccine against *Borrelia* (LYMErix™) by SmithKline Beecham, now GlaxoSmithKline (GSK) for the US market. Three doses of LYMErix™ over a period of one year were needed for optimal protection. After the first two doses, vaccine efficacy against Lyme borreliosis was 49%, and after the third dose, 76%. However, shortly after LYMErix™ was commercially available, it was withdrawn from the market in 2002. Reasons cited were matters of practical application of the vaccine, for example the need for booster injections every year or every other year, as well as the relatively high cost of this preventive approach compared with antibiotic treatment of early infection. In addition, there was a concern that LYMErix™ could trigger autoimmune reactions in a subgroup of the population due to sequence homology with a human protein, although this was never proven. In addition, cross-protection against other clinically important *Borrelia* species was not provided by this vaccine.

Accordingly, in one embodiment, it was an object of the present invention to provide an improved vaccine, e.g. for the prevention of Lyme borreliosis. Preferably, the vaccine is easily produced while being protective, safe and more effective than existing therapies and/or provides protection against more than one *Borrelia* species. Additionally, it is well-known in the art that different patients respond differently to different vaccine compositions. Therefore, in any case, it would be a distinct advantage to have alternative vaccines available as additional options for vaccinations against *Borrelia*.

The problem underlying the present invention is solved by a polypeptide comprising a hybrid C-terminal OspA fragment, wherein the hybrid fragment consists of a C-terminal domain of an OspA protein of *Borrelia* that is comprised of a fragment derived from an OspA protein of a *Borrelia* strain different than *B. garinii*, strain PBr, and a second fragment of OspA from *B. garinii*, strain PBr, and differs from the corresponding wild-type sequence at least by the introduction of at least one disulfide bond.

Surprisingly, the introduction of said hybrid C-terminal OspA fragment comprising a sequence from *B. valaisiana*, strain VS116, fused with a sequence from serotype 3 OspA (*B. garinii*, strain PBr), with an introduced disulfide bond, resulted in a heterodimer protein (Lip-S4D1-S3hybD1) that was easier to purify and stimulated a more specific immune response to serotype 3 OspA than the heterodimer Lip-S4D1-S3D1 of our previous invention (WO2014/006226). As shown in the Examples, the serotype 3 hybrid OspA C-terminal fragment of the present invention has a predicted electrostatic potential isocontour that is more similar to other OspA fragments from other serotypes than the serotype 3

OspA fragment. Furthermore, the serotype 3 hybrid OspA C-terminal fragment-containing heterodimer (Lip-S4D1-S3hybD1) was easier to purify, requiring less steps to get a much higher yield than the Lip-S4D1-S3D1 heterodimer of the previous invention. Additionally, although the observed antibody titers were similar, the antibodies stimulated by the improved heterodimer combination vaccine bound more specifically to *Borrelia* expressing serotype 3 OspA compared with the heterodimer combination vaccine of the previous invention. Finally, the in vivo protective capacity of the improved heterodimer combination vaccine was high against the four *Borrelia* serotypes tested.

DETAILED DESCRIPTION OF THE INVENTION

Accordingly, in a first aspect, the present invention relates to a polypeptide comprising a hybrid C-terminal fragment of an outer surface protein A (OspA), wherein said hybrid C-terminal OspA fragment consists of a C-terminal domain fusion of two different OspA of *Borrelia* strains and differs from the corresponding wild-type fragment at least by the introduction of at least one disulfide bond, e.g. a cystine. In particular, the hybrid C-terminal OspA fragment consists of a fusion of amino acids from the OspA proteins from a strain different to *B. garinii*, strain PBr, e.g., *B. valaisiana*, strain VS116, or *B. spielmanii*; with amino acids from the OspA protein of *B. garinii*, strain PBr, with the introduction of at least one disulfide bond (cystine). Specifically, the polypeptide comprises a hybrid C-terminal OspA (outer surface protein A of *Borrelia*) fragment, wherein the hybrid C-terminal OspA fragment consists, from the N- to C-terminal direction, of i) a first OspA portion consisting of amino acids 125-176 or amino acids 126-175 of OspA from a *Borrelia* strain that is not the corresponding fragment of *B. garinii*, strain PBr, with SEQ ID NO: 8, and ii) a second OspA portion consisting of amino acids 177-274 or amino acids 176-274, (but most preferably amino acids 177-274), of OspA from *B. garinii*, strain PBr (SEQ ID NO: 8), wherein the second OspA portion is mutant and cystine-stabilized in that it differs from the corresponding wild-type sequence at least by the substitution of the wild-type amino acid at position 182 of SEQ ID NO: 8 by a cysteine and by the substitution of the wild-type amino acid at position 269 of SEQ ID NO: 8 by a cysteine and wherein a disulfide bond between the cysteine at position 182 and the cysteine at position 269 of said second OspA fragment is present; and wherein the numbering of the amino acids and of the cysteine substitutions is according to the numbering of corresponding amino acids of the full length OspA of *B. burgdorferi* s.s., strain B31 (SEQ ID NO: 5).

Alternatively, the polypeptide comprises a hybrid C-terminal OspA fragment, wherein the hybrid C-terminal OspA fragment consists, from the N- to C-terminal direction, of
 i) a first OspA fragment (also referred to as a first OspA portion) consisting of amino acids 125-176 or amino acids 126-175 of OspA from a *Borrelia* strain that is not the corresponding fragment of *B. garinii*, strain PBr, with SEQ ID NO: 8, and
 ii) a second OspA fragment (also referred to as a second OspA portion) consisting of amino acids 177-274 of OspA from *B. garinii*, strain PBr (SEQ ID NO: 8), wherein the second OspA fragment differs from the corresponding wild-type sequence by the substitution of the wild-type amino acid at position 182 of SEQ ID NO: 8 by a cysteine and by the substitution of the wild-type amino acid at position 269 of SEQ ID NO: 8 and wherein a disulfide bond between the cysteine at position 182 and the cysteine at position 269 of said second OspA fragment is present; and
wherein the numbering of the cysteine substitutions is according to the numbering of corresponding amino acids of the full length OspA of *B. burgdorferi* s.s., strain B31 (SEQ ID NO: 5).

It has been found that a polypeptide according to the invention can be easily and effectively produced (see Example 2). Its production resulted in an increased yield in comparison to known products (see Example 2). Immunization with a polypeptide according to the invention produced higher levels of antibodies specific to the OspA protein in its native form and is thus an improved vaccine (see Example 3). Moreover, it provided protection against in vivo *Borrelia* challenge (see Example 4).

*Borrelia* is a genus of bacteria of the spirochete phylum. It causes borreliosis, a zoonotic, vector-borne disease transmitted primarily by ticks and some by lice, depending on the species. At present there are 36 known species of *Borrelia*. Of the 36 known species of *Borrelia*, 13 of these species are known to cause Lyme disease or borreliosis and are transmitted by ticks. The major *Borrelia* species causing Lyme disease are *Borrelia burgdorferi*, *Borrelia afzelii*, and *Borrelia garinii*. The term *B. burgdorferi* s.l. encompasses at least 13 *Borrelia* species (Table A-1). These species occur in different geographic regions, and live in nature in enzootic cycles involving ticks of the *Ixodes ricinus* complex (also called *Ixodes persulcatus* complex) and a wide range of animal hosts. Four *Borrelia* species are responsible for the majority of infections in humans: *B. burgdorferi* s.s., *B. afzelii*, *B. bavariensis* and *B. garinii*. Three other species, *B. lusitaniae*, *B. bissettii* and *B. spielmanii*, have occasionally been detected in humans, but their role in Lyme borreliosis is uncertain at present. New species of *Borrelia* are still being identified.

TABLE A-1

|  | Principal tick vector | Location |
| --- | --- | --- |
| Pathogenic species (4) | | |
| *Borrelia burgdorferi* | *Ixodes scapularis* | Northeastern/ |
| (*Borrelia burgdorferi* s.s.) | *Ixodes pacificus* | north-central US |
|  | *Ixodes ricinus* | Western US |
|  | *Ixodes persulcatus* | Europe |
|  |  | Asia |
| *Borrelia garinii* | *Ixodes ricinus* | Europe |
|  | *Ixodes persulcatus* | Asia |
| *Borrelia afzelii* | *Ixodes ricinus* | Europe |
|  | *Ixodes persulcatus* | Asia |
| *Borrelia bavariensis* | *Ixodes ricinus* | Europe |
|  | *Ixodes persulcatus* | Asia |
| Minimally pathogenic or non-pathogenic species (9) | | |
| *Borrelia andersonii* | *Ixodes dentatus* | Eastern US |
| *Borrelia bissettii* | *Ixodes spinipalpis* | Western US |
|  | *Ixodes pacificus* | Europe |
|  | *Ixodes ricinus* |  |
| *Borrelia valaisiana* | *Ixodes ricinus* | Europe and |
|  | *Ixodes columnae* | Asia |
| *Borrelia lusitaniae* | *Ixodes ricinus* | Europe |
| *Borrelia spielmanii* | *Ixodes ricinus* | Europe |
| *Borrelia japonica* | *Ixodes ovatus* | Japan |
| *Borrelia tanukii* | *Ixodes tanuki* | Japan |
| *Borrelia turdi* | *Ixodes turdus* | Japan |
| *Borrelia sinica* | *Ixodes persulcatus* | China |

As detailed above, *Borrelia* outer surface protein A (OspA) is an abundant immunogenic lipoprotein of *Borrelia* of particular interest because of its potential as a vaccine candidate. OspA of *B. burgdorferi* s.l. is a basic lipoprotein that has a molecular mass of approximately 30 kDa and is encoded on a linear plasmid. An important aspect of the OspA protein is its N-terminal lipidation; that is, fatty acids with a chain length of between C14 and C19 with or without double bonds are attached to the N-terminal cysteine residue, a feature that enhances the immunogenicity of the OspA protein. It has been shown that poorly-immunogenic synthetic peptides induce stronger antibody responses when lipidated; for example, when covalently coupled to $Pam_3Cys$ (Bessler and Jung, Research Immunology (1992) 143:548-552), a fatty acid substitution found at the amino terminus of many bacterial lipoproteins that are synthesized with a signal sequence specifying lipid attachment. Additionally, the $Pam_3Cys$ moiety was shown to enhance immune responses to OspA in mice, partially through its interaction with TLR-2/1 (Yoder, et al. (2003) Infection and Immunity 71:3894-3900). Therefore, lipidation of a C-terminal fragment of OspA would be expected to enhance the immunogenicity and protective capacity of the fragment.

Analysis of isolates of *B. burgdorferi* s.l. obtained in North America and Europe has revealed that OspA has antigenic variability and that several distinct groups can be defined based on serology. Anti-OspA mAbs which bind to specific N- and C-terminal antigenic determinants have been reported. X-ray crystallography and NMR analysis have been used to identify immunologically important hypervariable domains in OspA and have mapped the LA-2 epitope to C-terminal amino acids 203-257 (Ding et al., Mol. Biol. 302: 1153-64, 2000). Previous studies have shown that the production of antibodies against the C-terminal epitope LA-2 correlates with protective immunity after vaccination with OspA (Van Hoecke et al. Vaccine (1996) 14(17-18):1620-6 and Steere et al., N Engl J Med (1998) 339:209-215). Antibodies to LA-2 were shown to block the transmission of *Borrelia* from tick to host (Golde et al., Infect Immun (1997) 65(3):882-889). These studies suggested that the C-terminal portion of the OspA protein may be sufficient for inducing protective immunity. It should be noted that the sequence of the C-terminal portion of OspA is less highly-conserved between *Borrelia* serotypes than is the N-terminal portion (see FIG. 1).

Based on information from the studies outlined above, along with others, truncated forms of OspA comprising the C-terminal portion (also referred to herein as "OspA fragment" or "monomer") were used in the previous invention (WO2014/006226). The truncated forms of OspA proved to be less protective than the full-length OspA protein. Surprisingly, however, it was found in the course of the previous invention that the introduction of a disulfide bond in the truncated form (also referred to herein as "mutant OspA fragment", "cystine-stabilized OspA fragment", or "mutant fragment" or "cystine-stabilized fragment") overcomes this disadvantage. While not being limited to a specific mechanism, it is thought that improved protection is due to increased stability of the OspA fragment, as shown in assays measuring thermal stability.

In accordance with the previous invention, the mutant OspA fragment (in the present invention also referred to as second OspA fragment) may be derived from any *Borrelia* species; however, due to their prevalence in the medical field, particularly for humans, *B. burgdoiferi* s.s., *B. afzelii*, *B. bavariensis* and *B. garinii* are preferred. In accordance with the present invention, the first OspA portion is from any *Borrelia* strain except *B. garinii*, strain PBr and the second portion is from *B. garinii*, strain PBr. Therefore, the hybrid OspA fragment is derived from a fusion of amino acids from the OspA of *B. garinii*, strain PBr with amino acids from the OspA from any *Borrelia* species except *B. garinii*, strain PBr (and therefore an amino acid sequence different from that amino acids from the OspA from *B. garinii*, strain PBr), particularly from *B. burgdoiferi* s.s., *B. afzelii*, and *B. bavariensis*, especially *B. valaisiana*, strain VS116. The first OspA portion consists of amino acids 125-176 or amino acids 126-175 of OspA from a *Borrelia* strain that is not the corresponding fragment of *B. garinii*, strain PBr, with SEQ ID NO: 8, and the second OspA portion consists of amino acids 176-274 or most preferably amino acids 177-274 of OspA from *B. garinii*, strain PBr (SEQ ID NO: 8), wherein the second OspA portion is mutant and cystine-stabilized in that it differs from the corresponding wild-type sequence at least by the substitution of the wild-type amino acid at position 182 of SEQ ID NO: 8 by a cysteine and by the substitution of the wild-type amino acid at position 269 of SEQ ID NO: 8 by a cysteine and wherein a disulfide bond between the cysteine at position 182 and the cysteine at position 269 of said second OspA fragment is present; and wherein the numbering of the amino acids and of the cysteine substitutions is according to the numbering of corresponding amino acids of the full length OspA of *B. burgdorferi* s.s., strain B31 (SEQ ID NO: 5). However, further mutations relative to the wild-type portions may be present in the first and second portions according to the invention (see also below). In a preferred embodiment the above substitutions with cysteine at positions 182 and 269 are the only mutations relative to the wild-type. Alternatively, the cystine-stabilized amino acids 177-274 from *Borrelia garinii*, strain PBr differs therefrom by the substitution of the threonine residue at amino acid 233 of wild-type OspA of *Borrelia garinii*, strain PBr, with a proline residue only.

Preferred examples of polypeptides comprise a hybrid C-terminal OspA fragment consisting of amino acids 125-176 from *B. valaisiana*, strain VS116, and the cystine-stabilized amino acids 177-274 from *Borrelia garinii*, strain PBr (SEQ ID NO: 1), or a hybrid C-terminal OspA fragment consisting of amino acids 126-175 from *B. spielmanii* and the cystine-stabilized amino acids 177-274 from *Borrelia garinii*, strain PBr (SEQ ID NO: 51).

Therefore, in a preferred embodiment of the invention, the polypeptide comprises or consists of the amino acid sequence of SEQ ID NO: 1. Alternatively, the polypeptide comprises or consists of the amino acid sequence of SEQ ID NO: 51.

In one embodiment of the present invention, the second OspA portion is identical to the cystine-stabilized amino acids 177-274 from *Borrelia garinii*, strain PBr, but differs therefrom by the substitution of the threonine residue at amino acid 233 of wild-type OspA of *Borrelia garinii*, strain PBr, with a proline residue (SEQ ID NO: 7).

The four *Borrelia* species *B. burdorferi* s.s., *B. afzelii*, *B. bavariensis* and *B. garinii* can be further classified according to their OspA serotypes, which have been determined by analysis with monoclonal antibodies specific to the respective OspA protein. Serotypes 1-7, which account for the majority of human *Borrelia* infections, along with their rates of prevalence, are shown in Table A-2 below.

TABLE A-2

Serotype designation and prevalence of *B. burdorferi* s.s., *B. afzelii*, *B. bavariensis* and *B. garinii*. *Borrelia* isolated from human cerebrospinal fluid or skin or from tick vectors were serotyped by probing whole-cell lysates with mouse monoclonal antibodies, each specific to a particular epitope of OspA (as described by Wilske et al., J. of Clin Microbiol (1993) 31(2): 340-350 and presented by Baxter Bioscience at "Climate change effect on ticks and tick-borne diseases", Brussels, 6 Feb. 2009).

| *Borrelia* sp. | OspA serotype defined by mAb testing | Prevalence in human disease | Strain source for sequence | Seq ID No: |
|---|---|---|---|---|
| *B. burgdorferi* s.s. | 1 | 11% | B31 | 5 |
| *B. afzelii* | 2 | 63% | K78 | 6 |
| *B. garinii* | 3 | 1.5% | PBr | 7, 8 |
| *B. bavariensis* | 4 | 4% | PBi | 9 |
| *B. garinii* | 5 | 6% | PHei | 10 |
| *B. garinii* | 6 | 13% | DK29 | 11 |
| *B. garinii* | 7 | 0.5% | T25 | 12 |

The structure of the OspA protein from *B. burgdorferi* s.s. strain B31 was determined by Li et al. (Proc Natl Acad Sci (1997) 94:3584-3589). It is composed of N-terminal (α-strands 1 to 4) and central β-sheets (α-strands 5 to 14n [N-terminal part]), barrel sheet 1 (α-strands 14c [C-terminal part] to 16), barrel sheet 2 (α-strands 17 to 21) and a C-terminal α-helix. The term "C-terminal OspA fragment" or "OspA C-terminal domain" or "C-terminal domain" or "wild-type fragment" or "C-terminal portion" with respect to OspA as used throughout the present specification shall mean the C-terminal amino acid sequence of OspA, i.e., OspA lacking at least the N-terminal β-sheet (including α-strands 1 to 4). In OspA from *B. burgdorferi* s.s. strain B31, the N-terminal sheet consists of amino acids 17 to 70 (following post-translational cleavage of the 16 amino acid long lipidation signal peptide).

The C-terminal OspA fragment of the current invention may also include a lipidation signal sequence at the N-terminus, e.g., the lipidation signal sequence of amino acids 1 to 16 of OspA (SEQ ID NO: 13) or OspB (SEQ ID NO: 14) from *B. burgdorferi* s.s. strain B31, a lipidation signal sequence from *E. coli*, referred to herein as the "lpp lipidation signal" (SEQ ID NO: 15), or any other signal sequence, e.g., as defined below.

Lipidation of a protein with an N-terminal lipidation signal sequence, such as those present on a nascent OspA polypeptide, occurs in the *E. coli* expression vector by the step-wise action of the enzymes diacylglyceryl transferase, signal peptidase II and transacylase, respectively. The first step is the transfer of a diacylglyceride to the cysteine sulfhydryl group of the unmodified prolipoprotein, followed by the cleavage of the signal peptide by signal peptidase II and, finally, the acylation of the □-amino group of the N-terminal cysteine of the apolipoprotein. The result is the placement of one lipid and a glycerol group with two further lipids attached on the N-terminal cysteine residue of the polypeptide. The lipidation signal sequence, which is cleaved off during lipidation, is not present in the final polypeptide sequence.

Polypeptides are biological molecules of chains of amino acid monomers linked by peptide (amide) bonds. The covalent chemical bonds are formed when the carboxyl group of one amino acid reacts with the amino group of another. Polypeptides of the present invention are continuous and unbranched amino acid chains. The polypeptide of the present invention comprises a cystine bond. According to the current invention, the mutant OspA fragment may be a lipidated protein, also lipoprotein, wherein the lipid moieties, along with the glycerol group, is also referred to as "Lip". According to the invention, Lip comprises one to three lipids such as $C_{14-20}$ alkyl and/or $C_{14-20}$ alkenyl attached to a glycerol and an amino group of the N-terminal cysteine of the polypeptide of the invention, or preferably wherein Lip is a moiety of formula (I) below, $$\begin{array}{cc}
\text{O} & \text{O} \\
\| & \| \\
\text{O}-\text{C}-\text{R}_1 & \text{HN}-\text{C}-\text{R}_3, \\
| & | \\
\text{CH}_2-\text{CH}-\text{CH}_2-\text{S}-\text{CH}_2-\text{CH} \\
| & | \\
\text{O}-\text{C}-\text{R}_2 & \text{C}=\text{O} \\
\| & | \\
\text{O} & \text{X}
\end{array}$$

Formula (I)

in which one of $R_1$, $R_2$ or $R_3$ is $C_{14}$-$C_{20}$ alkyl or alkenyl, and each of the others, independently, is $C_{14}$-$C_{20}$ alkyl or $C_{14}$-$C_{20}$ alkenyl, and X is an amino acid sequence attached to the cysteine residue shown in Formula (I). More preferably, Lip plus the N-terminal cysteine of the polypeptide is N-palmitoyl-S-(2RS)-2,3-bis-(palmitoyloxy) propyl cysteine (referred to herein as "Pam₃Cys") and is connected via the carbonyl C of the cysteine to said amino acid sequence of the invention. In Formula (I) above, $R_1$, $R_2$ and $R_3$ would be palmitoyl moieties and X is an amino acid sequence attached to the cysteine residue.

In accordance with the current invention, the C-terminal domain of an OspA may lack at least the N-terminal domain homologous to amino acids 17 to 70 of OspA from *B. burgdorferi* s.s., strain B31. Additionally, the OspA C-terminal domain according to the present invention may also lack further portions of the central sheet as defined by Li and co-workers (Li et al., supra), particularly further strands such as the amino acid portions from amino acid 17 to 82, 93, 105, 118 or 119, preferably 17 to 129, more preferably 1 to 124, 1 to 125, 1 to 129 or 1 to 130 of any *Borrelia*, particularly *B. burgdorferi* s.s., strain B31, or homologous portions of an OspA protein from a *Borrelia* sp. other than *B. burgdorferi* s.s., strain B31.

In the context of the present invention, the OspA C-terminal domain is also referred to as "OspA fragment" or "fragment of OspA".

The "mutant C-terminal OspA fragment" or "mutant fragment" or "mutant OspA fragment" in the context of the polypeptide of the present invention and as used throughout the present specification shall mean the OspA C-terminal fragment, as defined above and herein, which differs from the wild-type fragment at least by at least two introduced cysteines that can form a disulfide bond; i.e., a cystine. Without being bound to that theory, it is assumed that the disulfide bond stabilizes the fragment in a conformation conducive to the induction of antibody binding. The fold of the wild-type C-terminal fragment of OspA shows reduced temperature stability in comparison to the full-length protein (Koide et al., Structure-based Design of a Second-generation Lyme Disease Vaccine Based on a C-terminal Fragment of *Borrelia burgdorferi* OspA, J. Mol. Biol. (2005) 350:290-299). For the present invention, the sequence of the C-terminal domain of the *B. burgdorferi* s.s., strain B31 OspA has been in silico analyzed to determine positions for introduced disulfide bridges that may enhance the stability of the fold of this C-terminal domain. The results of the analysis have been transferred to homologous OspA fragments of other *Borrelia* species with the assumption that the fold is conserved across species.

The "hybrid C-terminal OspA fragment" or "hybrid fragment" or "hybrid OspA fragment" in the context of the polypeptide of the present invention and as used throughout the present specification shall mean the OspA C-terminal fragment, as defined above and herein, which differs from the wild-type fragment in that a) the hybrid C-terminal OspA fragment consists of a fusion of amino acids from a first OspA protein from a strain different to *B. garinii*, strain PBr, e.g. *B. valaisiana*, strain VS116, or *B. spielmanii* (referred to as first OspA portion); with amino acids from a second OspA protein of *B. garinii*, strain PBr, with the introduction of at least one disulfide bond (cystine) (referred to as second OspA portion) and optionally one or more further mutations; and b) the at least two introduced cysteines in the hybrid C-terminal OspA fragment form a disulfide bond, i.e. a cystine, and wherein said introduced cysteines are introduced as described herein and in accordance with the teaching of WO2014/006226; and wherein the hybrid C-terminal OspA fragment results in a naturally folded fragment as measured e.g. by the efficiency of binding of antibodies resulting from the vaccination by this hybrid C-terminal OspA fragment in e.g. mice to *Borrelia* serotype 3 antigen, e.g. by testing the binding of said antibodies (obtained after three immunizations) to the surface of serotype 3 *Borrelia* by flow cytometry, e.g. as described in the Examples.

Typically, the disulfide bond may be introduced by the introduction of one or more, preferably two, cysteine residues, wherein a disulfide bond (S—S bridge) is formed between the thiol groups of two cysteine residues forming the amino acid cystine. Only one cysteine residue need be introduced if a disulfide bond is formed with a cysteine residue present in the wild-type OspA fragment. The two cysteines are introduced by amino acid substitution. Substitutions are a) at position 182 of the amino acid of the relevant wild-type OspA amino acid sequence by a cysteine and b) at position 269 of the amino acid of the relevant wild-type OspA amino acid sequence by a cysteine and wherein a disulfide bond between the cysteine at position 182 and the cysteine at position 269 of said OspA fragment is present forming thus a cystine. The numbering of the cysteine substitutions is according to the numbering of corresponding amino acids of the full length OspA of *B. burgdorferi* s.s., strain B31 (SEQ ID NO: 5).

The mutant or hybrid OspA fragment may also comprise further mutations relative to the wild-type. As detailed above, the structure and surface domain of OspA are known in the art. Accordingly, the mutant fragment may comprise further mutations, particularly at sites not on the surface of the protein and/or not involved in the immune response and, therefore not impacting antigenic capacity. These can include one or more amino acid deletion(s), particularly small (e.g., up to 10, 9, 8, 7, 6, 5, 4, 3, 2 or 1 amino acids) deletions, one or more amino acid addition(s) (particularly C- or N-terminally), one or more amino acid substitution(s), particularly one or more conservative amino acid substitutions. Preferably, the number of further muations in the first and second portion relative to the respective wild-type is at most 10, 9, 8, 7, 6, 5, 4, more preferably 3 or 2, especially 1. More preferably the further mutation(s) is/are in the second OspA portion only. Preferred mutations are substitutions, especially conservative substitutions. Examples of conservative amino acid substitutions include, but are not limited to, those listed below:

| Ala | Ser | Leu | Ile; Val |
|-----|-----|-----|----------|
| Arg | Lys | Lys | Arg; Gln; Asn |
| Asn | Gln; His | Met | Leu; Ile |
| Asp | Glu | Phe | Met; Leu; Tyr |
| Cys | Ser | Ser | Thr |
| Gln | Asn | Thr | Ser |
| Glu | Asp | Trp | Tyr |
| His | Asn; Gln | Tyr | Trp; Phe |
| Ile | Leu, Val | Val | Ile; Leu |

Preferred mutations include changes in selected portions of the fragment, for example, wherein the sequence with sequence similarity to human leukocyte function-associated antigen (hLFA-1), which exists in *B. burgdorferi* s.s. is modified, for example, replaced by a homologous sequence from an OspA protein from another *Borrelia* sp. The rationale for this modification is to reduce the risk for inducing immunological cross-reaction with human proteins. Another preferred mutation is the substitution of a proline for the threonine at position 233 in the OspA polypeptide sequence from *B. garinii*, strain PBr (SEQ ID NO: 8). Also possible is the addition of a signal sequence for lipidation in the final, or an intermediate, fragment, or the addition of a marker protein (e.g., for identification or purification).

In some embodiments, the mutant or hybrid OspA fragment has an amino acid sequence that has 60%, preferably at least 70%, more preferably at least 80%, more preferably at least 85%, more preferably at least 90%, even more preferably at least 95% sequence identity to the wild-type fragment. In another embodiment, the sequence differs by at most 10%, at most 9%, at most 8%, at most 7%, at most 6%, 5%, 4%, 3%, 2%, most preferably at most 1%, due to a sequence addition, deletion or substitution.

Identity, as known in the art and as used herein, is the relationship between two or more polypeptide sequences, as determined by comparing the sequences. In the art, identity also means the degree of sequence relatedness between polypeptide or polynucleotide sequences, as the case may be, as determined by the match between strings of such sequences. Identity can be readily calculated. While a number of methods exist to measure identity between two polynucleotides or two polypeptide sequences, the term is well known to skilled artisans (e.g. Sequence Analysis in Molecular Biology, von Heinje, G., Academic Press, 1987). Preferred methods to determine identity are designed to give the largest match between the sequences tested. Methods to determine identity are codified in computer programs. Preferred computer program methods to determine identity between two sequences include, but are not limited to, the GCG program package (Devereux, J. et al., 1984), BLASTP, BLASTN, and FASTA (Altschul, S. et al., 1990).

In contrast to the mutant or hybrid OspA fragment, the "wild-type fragment" or "wild-type OspA fragment" in the context of the present invention relates to a fragment of a naturally-occurring OspA of *Borrelia*. The wild-type fragment is obtained by N-terminal deletions, but it does not comprise internal deletions (except from signal sequences as detailed herein) or mutations. In relation to the hybrid and mutant OspA fragment, the wild-type fragment consists of an identical part of the OspA (identical length and same strain of OspA, etc.) and differs only in the alteration(s) detailed above.

The Polypeptides of the Invention

A polypeptide is a single linear polymer of amino acids linked by peptide bonds, in some cases also by disulfide bonds. In accordance with the present invention, the polypeptide may also comprise one or more posttranslational modifications; i.e., an attached biochemical functional group, such as an attached acetate, phosphate, lipid or carbohydrate, preferably a lipid or lipids attached to the N-terminal cysteine along with a glycerol, more preferably 1 to 3 $C_{14}$-$C_{20}$ alkyl or alkenyl moieties, even more preferably 1 to 3 palmitoyl groups, most preferably three palmitoyl groups ($Pam_3$).

The polypeptide of the present invention is as defined above and comprises or consists of a hybrid C-terminal OspA fragment, wherein the hybrid C-terminal OspA fragment consists, from the N- to C-terminal direction, of
  i) a first OspA portion consisting of amino acids of a first C-terminal part of OspA from a *Borrelia* strain that is not the corresponding fragment of *B. garinii*, strain PBr, with SEQ ID NO: 8, and starts at a position around 125 or 126 and ends at position 175 or 176; and
  ii) a second OspA portion consisting of a second C-terminal part of OspA that continuously follows the first C-terminal part (e.g. if the first C-terminal part ends at position 175, the second C-terminal part continues at position 176; or if the first C-terminal part ends at positions 176, the second C-terminal part continues at positions 177 and so forth, however it may also be that one or two or more up to 10 amino acids may be deleted in the fusion area of the 2 C-terminal parts, e.g. and most preferably if the first C-terminal part ends at position 175, the second C-terminal part continues at position 177), wherein the second OspA fragment differs from the corresponding wild-type sequence by the substitution of the wild-type amino acid at position 182 of SEQ ID NO: 8 by a cysteine and by the substitution of the wild-type amino acid at position 269 of SEQ ID NO: 8 by a cysteine and wherein a disulfide bond between the cysteine at position 182 and the cysteine at position 269 of said second OspA fragment is present forming a cysteine (also referred to as "cystine-stablized OspA fragment"); and
wherein the numbering of the amino acids and of the cysteine substitutions is according to the numbering of corresponding amino acids of the full length OspA of *B. burgdorferi* s.s., strain B31 (SEQ ID NO: 5).

In a further embodiment of the present invention, the polypeptide comprises or consists of the hybrid C-terminal OspA fragment consisting of amino acids 125-176 from *B. valaisiana*, strain VS116, and the cystine-stabilized amino acids 177-274 from *Borrelia garinii*, strain PBr (SEQ ID NO: 1).

In a further embodiment of the present invention, the polypeptide comprises or consists of the hybrid C-terminal OspA fragment consisting of amino acids 126-175 from *B. spielmanii* and the cystine-stabilized amino acids 177-274 from *Borrelia garinii*, strain PBr (SEQ ID NO: 51).

In a further embodiment of the present invention, the polypeptide is as defined herein, and wherein the second OspA portion is identical to the cystine-stabilized amino acids 177-274 from *Borrelia garinii*, strain PBr, but differs therefrom only by the substitution of the threonine residue at amino acid 233 of wild-type OspA of *Borrelia garinii*, strain PBr, with a proline residue.

The polypeptides of the invention as defined above and further as defined herein provide for antibody titers in immunized animals, wherein said antibodies show improved binding to their respective antigens in situ when compared to relevant prior art polypeptides (e.g. as defined in WO2014/006226). Preferably, a polypeptide comprising the hybrid C-terminal OspA fragment of the invention effects at least a 1.5-fold increase, preferably at least a 2-fold increase, more preferably at least a 3-fold increase, even more preferably at least a 4-fold increase, even more preferably at least a 5-fold increase, most preferably at least a 10-fold increase in fluorescence intensity, measured by flow cytometry and illicited by antibodies raised after three immunizations with the polypeptide in mice by binding to the surface of serotype 3 *Borrelia*, in comparison to the fluorescence intensity illicited by antibodies raised to a polypeptide comprising a C-terminal domain of an OspA protein of *Borrelia* which differs from the corresponding wild-type OspA sequence by at least the addition of at least one cysteine bond, more preferably the Lip-S4D1-S3D1 heterodimer protein as defined by SEQ ID NO: 31, particularly wherein the increase may be determined as described in Example 3.

Furthermore, in a further embodiment of the present invention, the polypeptide of the invention as defined above and herein can be produced in higher yields with standard processes and require less purification steps when compared to relevant prior art polypeptides (e.g. as defined in WO2014/006226). Preferably, a polypeptide comprising the hybrid C-terminal OspA fragment of the invention shows at least a 1.5-fold increase, preferably at least a 2-fold increase, more preferably at least a 3-fold increase, even more preferably at least a 4-fold increase, even more preferably at least a 5-fold increase, most preferably at least a 10-fold increase in production yield, measured in milligrams per gram biomass, in comparison to a polypeptide comprising a C-terminal domain of an OspA protein of *Borrelia* which differs from the corresponding wild-type OspA sequence by at least the addition of at least one cysteine bond, more preferably the Lip-S4D1-S3D1 heterodimer protein as defined by SEQ ID NO: 31, particularly wherein the increase may be determined as described in Example 2.

Preferably, a polypeptide comprising the hybrid C-terminal OspA fragment of the invention requires less steps for purification than a polypeptide comprising a C-terminal domain of an OspA protein of *Borrelia* which differs from the corresponding wild-type OspA sequence by at least the addition of at least one cysteine bond, more preferably the Lip-S4D1-S3D1 heterodimer protein as defined by SEQ ID NO: 31; more specifically, requires at least one less chromatography step.

In a further embodiment of the present invention, the polypeptide comprises a) a hybrid C-terminal OspA fragment as defined above and herein, and b) a mutant OspA fragment.

In a further embodiment of the present invention, the polypeptide of the invention comprises a) a hybrid C-terminal OspA fragment as defined herein, and b) a second OspA fragment, wherein said OspA fragment is C-terminal in that it consists of a C-terminal domain of an OspA protein of *Borrelia* and is mutant and cystine-stabilized in that it differs from the corresponding wild-type OspA sequence at least by the substitution of the amino acid at position 182 of the wild-type sequence by a cysteine and by the substitution of the amino acid at position 269 of the wild-type sequence by a cysteine and wherein a disulfide bond between the cysteine at position 182 and the cysteine at position 269 of said OspA fragment is present; and furthermore wherein said mutant OspA fragment starts at position 123, 124, or 125 and ends at position 273 or 274; and furthermore wherein the numbering of the amino acids and of the cysteine substitutions is according to the numbering of corresponding amino acids of the full length OspA of *B. burgdorferi* s.s., strain B31 (SEQ ID NO: 5). In one embodiment of the present invention, the second OspA fragment may be any of the mutant C-terminal fragments of OspA as defined above, e.g. in the context of the previous invention (WO2014/006226).

According to the present invention, said mutant OspA fragment and hybrid fragment of the invention do not comprise (i) the N-terminal sheet as defined above and (ii) optionally one or more further strands of the central sheet as defined above. However, the polypeptide may comprise one or more functional sequences such as a signal sequence, e.g., a lipidation signal sequence or a posttranslational modification, such as lipidation.

In a further embodiment of the present invention, the polypeptide of the present invention consists of (i) one or more mutant OspA fragments, wherein at least one is a hybrid C-terminal OspA fragment according to the present invention, optionally joined by linkers, e.g., as defined below or one or more mutant OspA fragments and a serotype 3 hybrid OspA C-terminal fragment and (ii) optionally one or more amino acids heterologous to OspA, particularly a signal sequence and (iii) optionally a posttranslational modification, such as lipidation.

Thus, in a further embodiment of the present invention, the polypeptide of the invention as defined above and herein additionally may comprise:
i) a polypeptide that is lipidated or wherein the polypeptide comprises a lipidation signal, preferably the *E. coli*-derived lpp lipidation signal MKATKLVL-GAVILGSTLLAG (SEQ ID NO: 15); and/or
ii) a polypeptide that comprises a lipidation site peptide lead by an N-terminal cysteine residue as a site for lipidation, preferably CSS; and/or
iii) a polypeptide that comprises a linker between the hybrid C-terminal OspA fragment and the second cysteine-stabilized OspA fragment, particularly wherein said linker comprises e.g. GTSD-KNNGSGSKEKNKDGKYS (SEQ ID NO: 16).

In one embodiment of the present invention, the second C-terminal OspA fragment is a hybrid C-terminal fragment of OspA according to the present invention.

In a further embodiment of the present invention, the polypeptide comprises or consists of the heterodimer of Lip-S4D1-S3hybD1 (SEQ ID NO: 27). Therefore, in a further aspect, the present invention relates to a polypeptide comprising or consisting of an amino acid sequence of SEQ ID NO: 27 (heterodimer of Lip-S4D1-S3hybD1).

The polypeptide of the present invention has protective capacity. As detailed above, the introduction of a disulfide bond into the hybrid and hybrid/mutant OspA fragment but also the hybrid nature of the OspA fragment of the invention increases the protective capacity of the polypeptide relative to a polypeptide comprising the respective fragment without the disulfide bond(s) and hybrid nature of the OspA fragment. In some embodiments, the protective capacity is increased by at least 10%, more preferably by at least 20%, more preferably by at least 30%, more preferably by at least 40%, more preferably by at least 50%, more preferably by at least 60%, more preferably by at least 70%, more preferably by at least 80%, even more preferably by at least 90% relative to a polypeptide comprising the respective fragment without the disulfide bond(s) and hybrid nature of the OspA fragment.

The term protective capacity describes the ability to protect a subject against a *Borrelia* infection. With respect to the polypeptide of the invention, protective capacity relates to the ability of the polypeptide to induce an immune response that protects a subject against a *Borrelia* infection. Protective capacity can be tested by administering to a subject the polypeptide in a manner to induce an immune reaction against the polypeptide. Thereafter, the subject may be challenged with *Borrelia*.

The subject's reaction to the infection is monitored. Particularly, the presence of *Borrelia* in the subject may be determined. For example, the polypeptide is protective if *Borrelia* cannot be detected in the subject. The presence of *Borrelia* can be determined by detecting *Borrelia*-specific nucleic acids (e.g., by PCR) or *Borrelia*-specific antibodies (e.g., by ELISA or Western blot) or by detecting *Borrelia* itself (e.g., culturing organs or tissues in growth medium and verifying the presence of *Borrelia* by microscopy). In particular, the protective capacity ("pc"), reported as a percentage, for a particular dose is defined as follows:

$$pc\ (\%)=[(\text{number of total tested subjects}-\text{number of }Borrelia\text{-infected subjects})/\text{number of total tested subjects}]\times 100$$

Differences in protective capacity ($\Delta pc$) may be determined by, e.g. comparing the protective capacity (pc) of a mutant OspA fragment with a disulfide bond(s) (pc [with bond]) to the protective capacity of an OspA fragment without a disulfide bond(s) (pc [w/o bond]). In accordance with the present invention, the polypeptides to be compared differ only in the introduction of at least one disulfide bond. The change in protective capacity ($\Delta pc$) by the introduction of the disulfide bond(s) is determined as follows:

$$\Delta pc=(pc[\text{sample}]-pc[\text{control}])$$

e.g. $\Delta pc=(pc[\text{with bond}]-pc[\text{w/o bond}])$

If $\Delta pc$ is greater than zero (>0), assuming all other parameters (e.g., dose and assay) are the same, then the protective capacity of the sample (e.g. the mutant OspA fragment with a disulfide bond(s)) is better than the protective capacity of the control (e.g. the OspA fragment without a disulfide bond(s)). Conversely, if $\Delta pc$ is less than zero (<0) and assuming all other parameters (e.g., dose and assay) are the same, then the protective capacity of the sample (e.g. the mutant OspA fragment with a disulfide bond(s)) is less than the protective capacity of the comparison (e.g., the OspA fragment without a disulfide bond(s)).

Preferably, the polypeptide of the present invention is assessed for its protective capacity by an in vivo challenge assay wherein mice immunized with the polypeptide of the invention or with a placebo control are challenged with *Borrelia* introduced into the immunized subjects with a hypodermic needle (Needle Challenge Method) or by introduction by a tick vector (Tick Challenge Method).

The Needle Challenge Method is carried out for the desired *Borrelia* strain (e.g., *B. burgdorferi*, strain ZS7) by subcutaneously introducing *Borrelia* at a dose between 20 and 50 times the Infectious Dose $(ID)_{50}$ to mice that are immunized with said first polypeptide of the first aspect or with an appropriate placebo (negative) control, such as buffer or adjuvant alone and comparing the rates of infection in the challenged mice. The $ID_{50}$ is defined as the dose at which 50% of the challenged mice are infected. The dose of *Borrelia* is measured in numbers of bacteria. The challenge dose can vary widely and is strain-dependent; therefore, the virulence of the strain must first be assessed by challenge experiments for determination of $ID_{50}$. Four weeks after needle challenge, blood and tissues are collected for readout methods to determine the infection status. These readout methods can be e.g. VlsE ELISA on sera or qPCR on collected tissues for identification of *Borrelia*, as described herein, or other methods.

The Tick Challenge Method is carried out by applying at least one tick nymph (e.g., *I. ricinus*) infected with *Borrelia* (e.g., *B. afzelii*, strain IS1), to a mouse that is immunized with said first polypeptide of the first aspect; and b) applying at least one infected tick nymph to a second mouse that is immunized with said second polypeptide of the first aspect; and c) comparing the rates of infection in the two mice, generally six weeks after challenge. Preferably, the assay or test is done with a group of mice per polypeptide to be tested. A suitable test is also described and illustrated in the Examples. Assessment of infection status can be done using VlsE ELISA on sera or qPCR on DNA isolated from collected tissues, or using other suitable methods.

In a preferred embodiment of the present invention, the products of the invention such as, e.g. the polypeptides of the invention comprising the hybrid OspA fragment and preferably the mutant OspA C-terminal fragment administered 3 times to a subject at a dose of 30 µg, preferably 10 µg, preferably 5.0 µg, preferably 1.0 µg, preferably 0.3 µg or lower have a protective capacity of 50% or more, preferably 60% or more, preferably 70% or more, more preferably 80% or more, more preferably 90% or more, even more preferably 95% or more, most preferred 99% or more. In one embodiment, the protective capacity is assessed in an in vivo challenge method, preferably a Tick Challenge Method, more preferably a Needle Challenge Method, e.g. as described in the Examples.

In a preferred embodiment, the difference in protective capacity (Δpc) between the polypeptides of the invention comprising the hybrid OspA C-terminal fragment and the placebo (negative) control is at least 50%, especially at least 60%, preferably at least 70%, more preferably at least 80%, even more preferably at least 90%, even more preferably at least 95%, most preferably at least 99%, when administered 3 times to a subject at a dose of 30 µg, preferably 10 µg, preferably 5.0 µg, preferably 1.0 µg, preferably 0.3 µg or lower.

In accordance with the present invention, the first part of the hybrid OspA may be from any *Borrelia* strain other than *B. garinii*, strain PBr, with SEQ ID NO: 8, particularly from those specified herein such as *B. burgdorferi* s.s., *B. garinii* (not strain PBr), *B. afzelii*, *B. andersoni*, *B. bissettii*, *B. valaisiana*, *B. lusitaniae*, *B. spielmanii*, *B. japonica*, *B. tanukii*, *B. turdi* or *B. sinica*, *B. bavariensis*, preferably from *B. burgdorferi* s.s., *B. afzelii*, *B. bavariensis* or *B. garinii*, or a fusion of OspA protein fragments from two or more of these species. Preferably, the OspA is from *B. valaisiana*, particularly strain VS116 (SEQ ID NO: 4) but may be from *B. afzelii*, particularly strain K78, OspA serotype 2 (SEQ ID NO: 6); *B. burgdorferi* s.s., particularly strain B31, OspA serotype 1 (SEQ ID NO: 5); *B. garinii*, particularly strain PBr, OspA serotype 3 (SEQ ID NO: 8); *B. bavariensis*, particularly strain PBi, OspA serotype 4 (SEQ ID NO: 9); *B. garinii*, particularly strain PHei, OspA serotype 5 (SEQ ID NO: 10); *B. garinii*, particularly strain DK29, OspA serotype 6 (SEQ ID NO: 11) or *B. garinii*, particularly strain T25, OspA serotype 7 (SEQ ID NO: 12). The amino acid sequences of these OspA proteins (full-length) are given below.

In accordance with the present invention, the disulfide bond may also be formed between cysteines that have been introduced at any position of the OspA fragment allowing or supporting appropriate folding of the fragment. The positions may be selected, as detailed above, based on the known structure of the OspA. In a preferred embodiment, the polypeptide of the current invention contains at least one disulfide bond introduced by the insertion of a cysteine residue at one of residues 182+/−3 and one of residues 269+/−3 (disulfide bond type 1; "D1") of a *B. afzelii*, particularly *B. afzelii* K78 serotype 2 OspA, or the homologous amino acids of an OspA from a *Borrelia* other than *B. afzelii*, such as *B. burgdorferi* s.s., particularly strain B31, serotype 1; *B. garinii*, particularly strain PBr, serotype 3; *B. bavariensis*, particularly strain PBi, serotype 4; *B. garinii*, particularly strain PHei, serotype 5; *B. garinii*, particularly strain DK29, serotype 6; *B. garinii*, particularly strain T25, serotype 7 or a fusion of amino acids 125-176 of OspA of *B. valaisiana*, strain VS116, or amino acids 126-175 of OspA of *B. spielmanii* and amino acids 177-274 of *B. garinii*, strain PBr (SEQ ID NO: 8).

It is noted that:

Position 182+/−3 is an abbreviation for position 179, 180, 181, 182, 183, 184 or 185, preferably 182.

Position 269+/−3 is an abbreviation for position 266, 267, 268, 269, 270, 271 or 272, preferably 269.

In a preferred embodiment, the additional mutant fragment is derived from the amino acids from position 125, 126, 130 or 131 to position 273 of the wild-type sequence of the OspA of *B. afzelii* strain K78, serotype 2 (SEQ ID NO: 6) and differs only by the introduction of at least one disulfide bond, particularly wherein the at least one disulfide bond is between positions 182 and 269 (disulfide bond type 1); or the homologous fragments and positions of an OspA from a *Borrelia* sp. other than *B. afzelii*, such as *B. burgdorferi* s.s., particularly strain B31, serotype 1; *B. garinii*, particularly strain PBr, serotype 3; *B. bavariensis*, particularly strain PBi, serotype 4; *B. garinii*, particularly strain PHei, serotype 5; *B. garinii*, particularly strain DK29, serotype 6 or *B. garinii*, particularly strain T25, serotype 7.

In a further embodiment, the mutant fragment may be an amino acid sequence selected from the group consisting of SEQ ID NO: 43, SEQ ID NO: 44, SEQ ID NO: 45, SEQ ID NO: 46, SEQ ID NO: 47, SEQ ID NO: 48, most preferably SEQ ID NO: 46, and an amino acid sequence that has at least 80%, more preferably at least 85%, more preferably at least 90%, even more preferably at least 95% sequence identity to at least one of sequences with SEQ ID NOs: 19 to 25, wherein the cysteines are not replaced. Further details on mutations and sequence identity are given above.

As detailed above, the polypeptide of the present invention may comprise signal sequences. It has been shown that lipidation confers adjuvant properties on OspA. Accordingly, lipidated forms of the polypeptide of the invention or polypeptides comprising a lipidation signal are preferred. In a preferred embodiment, the polypeptide of the current invention comprises a lipidation signal, preferably a lipidation signal of a *Borrelia* outer surface protein, OspA or OspB (SEQ ID NOs: 13 and 14, respectively) or more preferably an *E. coli* lpp lipidation signal sequence (SEQ ID NO: 15). The OspA fragment of the invention comprising a lipidation signal is lipidated during processing and the lipidation signal peptide is cleaved off; therefore, the signal peptide is no longer present in the mature lipidated protein.

Lipidated proteins according to the current invention are labeled with "Lip" at the N-terminus to indicate the addition of 3 fatty acid groups and a glycerol to the polypeptide. Suitable lipidation signals as described above include MKKYLLGIGLILALIA (SEQ ID NO: 13), MRLLIGFALALALIG (SEQ ID NO: 14) and MKATKLVLGAVILGSTLLAG (SEQ ID NO: 15). Because lipid moieties and a glycerol are attached to the N-terminal cysteine residue which is present in the full-length wild-type OspA protein, OspA C-terminal fragments for lipidation may additionally comprise a peptide comprising a cysteine residue followed by additional amino acids. For example, sequences such as CSS or CKQN (SEQ ID NO: 62) immediately C-terminal to the lipidation signal sequence provide an N-terminal cysteine residue for lipidation upon cleavage of the lipidation signal peptide. The lipidated cysteine-containing peptides are present in the final lipidated polypeptide of the invention.

It has been speculated that the OspA protein of *B. burgdorferi* s.s. comprises a sequence with the capacity to bind to a T cell receptor that also has the capacity to bind to human leukocyte function-associated antigen (hLFA-1) (herein referred to also as "hLFA-1-like sequence"). The similarity of this OspA region to hLFA-1 may result in an immune response with cross-reactivity upon administration of *B. burgdorferi* s.s. OspA to a human subject and may induce autoimmune diseases, particularly autoimmune arthritis, in susceptible individuals. Accordingly, in a preferred embodiment, the polypeptide of the current invention does not comprise a sequence with binding capacity to the T cell receptor that has a binding capacity to the human leukocyte function-associated antigen (hLFA-1), and particularly does not comprise the amino acid sequence GYVLEGTLTAE (SEQ ID NO: 17). To this end, the hLFA-1-like sequence, particularly the amino acid sequence GYVLEGTLTAE (SEQ ID NO: 17), may be replaced with a homologous sequence from an OspA protein of another *Borrelia* sp., particularly with NFTLEGKVAND (SEQ ID NO: 18).

In a preferred embodiment, the polypeptide of the current invention comprising at least one disulfide bond essentially establishes the same protective capacity with said polypeptide against a *Borrelia* infection relative to at least one of the wild-type full-length OspA proteins derived from at least one *Borrelia* strain, particularly *B. afzelii* K78, OspA serotype 2 (SEQ ID NO: 6); *B. burgdorferi* s.s., particularly strain B31, serotype 1 (SEQ ID NO: 5); *B. garinii*, particularly strain PBr, serotype 3 (SEQ ID NOs: 7 and 8); *B. bavariensis*, particularly strain PBi, serotype 4 (SEQ ID NO: 9); *B. garinii*, particularly strain PHei, serotype 5 (SEQ ID NO: 10); *B. garinii*, particularly strain DK29, serotype 6 (SEQ ID NO: 11) or *B. garinii*, particularly strain T25, serotype 7 (SEQ ID NO: 12).

Please note that further details on mutations and sequence identity are given above.

TABLE A-3

Nomenclature and SEQ ID NOs. of the lipidated mutant OspA fragment heterodimers described in the current invention.

| Lipidated mutant OspA fragment heterodimer* | SEQ ID NO: |
| --- | --- |
| Lip-S1D1-S2D1 | 29 |
| Lip-S5D1-S6D1 | 33 |
| Lip-S4D1-S3D1 | 31 |
| Lip-S4D1-S3hybD1 | 27 |

*S = Serotype (1-6) (see Table A-2); S3hyb = fusion of amino acids 125-176 of *B. valaisiana* and amino acids 177-274 of *B. garinii*, strain PBr D1 = Disulfide Bond Type 1(cysteine residues inserted at position 183 +/− 3 and 270 +/− 3); Lip = lipidation: the N-terminal addition of glycerol and fatty acid residues.

In another preferred embodiment, the polypeptide according to the first aspect comprises at least two or three mutant fragments which are connected via one or more linkers. A linker is a rather short amino acid sequence employed to connect two fragments. It should be designed in order to avoid any negative impact on the fragments, their interaction in subjects to be treated or vaccinated or upon their protective capacity. Preferred are short linkers of at most 21 amino acids, particularly at most 15 amino acids, especially at most 12 or 8 amino acids. More preferably, the one or more linkers is/are composed of small amino acids in order to reduce or minimize interactions with the fragments, such as glycine, serine and alanine. A preferred linker is the "LN1" peptide linker, a fusion of two separate loop regions of the N-terminal half of OspA from *B. burgdorferi* s.s., strain B31 (aa 65-74 and aa 42-53, with an amino acid exchange at position 53 of D53S) which has the following sequence: GTSDKNNGSGSKEKNKDGKYS (SEQ ID NO: 16). The linker may comprise a lipitation site.

In another preferred embodiment, the polypeptide according to the first aspect comprises a polypeptide with a total size of at most 500 amino acids, comprising two or three different mutant fragments as defined in preferred embodiments of the first aspect; or a polypeptide which consists of essentially two or three different mutant fragments, one or two linkers and, optionally, an N-terminal cysteine; and/or a polypeptide which consists of essentially two or three different mutant fragments, an N-terminal extension of the fragment consisting of at most 24, 23, 22, 21, 20, 19, 18, 17, 16, 15, 14, 13, 12 or 11 amino acids, preferably at most 10, 9, 8, 7 or 6 amino acids, still more preferably at most 5, 4, 3, 2 or 1 amino acid(s), wherein the N-terminal extension is located directly N-terminally from the fragment in the respective *Borrelia* OspA and, optionally, an N-terminal cysteine. The N-terminal cysteine may optionally be followed by a short peptide linker from 1-10 amino acids long, and preferably takes the form of an N-terminal CSS peptide.

The Nucleic Acids of the Invention and Related Aspects

In a further aspect, the present invention relates to a nucleic acid coding for a polypeptide as defined herein and above in the context of the present invention. The nucleic acid may be comprised in a vector and/or cell.

The invention further provides a nucleic acid encoding a polypeptide of the invention. For the purposes of the invention the term "nucleic acid(s)" generally refers to any polyribonucleotide or polydeoxyribonucleotide, which may be unmodified RNA or DNA or modified RNA or DNA including single and double-stranded regions/forms.

The term "nucleic acid encoding a polypeptide" as used herein encompasses polynucleotides that include a sequence encoding a peptide or polypeptide of the invention. The term also encompasses polynucleotides that include a single continuous region or discontinuous regions encoding the peptide or polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

It will be appreciated by those of ordinary skill in the art that, as a result of the degeneracy of the genetic code, there are many nucleotide sequences that encode a polypeptide as described herein. Some of these polynucleotides bear minimal similarity to the nucleotide sequence of any native (i.e., naturally occuring) gene. Nonetheless, polynucleotides that vary due to differences in codon usage are specifically contemplated by the present invention, for example polynucleotides that are optimized for human and/or primate and/or *E. coli* codon selection.

Sequences encoding a desired polypeptide may be synthesized, in whole or in part, using chemical methods well known in the art (see Caruthers, M. H. et al., Nucl. Acids Res. Symp. Ser. pp. 215-223 (1980), Horn et al., Nucl. Acids Res. Symp. Ser. pp. 225-232 (1980)). Alternatively, the protein itself may be produced using chemical methods to synthesize the amino acid sequence of a polypeptide, or a portion thereof. For example, peptide synthesis can be performed using various solid-phase techniques (Roberge et al., Science 269:202-204 (1995)) and automated synthesis may be achieved, for example, using the ASI 431 A Peptide Synthesizer (Perkin Elmer, Palo Alto, Calif.).

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In a further aspect of the invention the present invention relates to vectors comprising a nucleic acid of the invention, e.g. linked to an inducible promoter such that when the promoter is induced a polypeptide encoded by the nucleic acid is expressed. In a preferred embodiment, the vector is pET28b(+) (http://www.addgene.org/vector-database/2566/).

A further aspect of the invention comprises said vector wherein the inducible promoter is activated by addition of a sufficient quantity of IPTG (Isopropyl β-D-1-thiogalactopyranoside) preferably to the growth medium. Optionally this is at a concentration of between 0.1 and 10 mM, 0.1 and 5 mM, 0.1 and 2.5 mM, 0.2 and 10 mM, 0.2 and 5 mM, 0.2 and 2.5 mM, 0.4 and 10 mM, 1 and 10 mM, 1 and 5 mM, 2.5 and 10 mM, 2.5 and 5 mM, 5 and 10 mM. Alternatively the promoter may be induced by a change in temperature or pH.

Nucleic acid molecule as used herein generally refers to any ribonucleic acid molecule or deoxyribonucleic acid molecule, which may be unmodified RNA or DNA or modified RNA or DNA. Thus, for instance, nucleic acid molecule as used herein refers to at least single- and double-stranded DNA, hybrid molecules comprising DNA and RNA that may be single-stranded or, more typically, double-stranded, or a mixture of single- and double-stranded regions. As used herein, the term nucleic acid molecule includes DNA or RNA molecules as described above that contain one or more modified bases. Thus, DNA or RNA molecules with backbones modified for stability or for other reasons are "nucleic acid molecule" as that term is intended herein. Moreover, DNA or RNA species comprising unusual bases, such as inosine, or modified bases, such as tritylated bases, to name just two examples, are also nucleic acid molecules as defined herein. It will be appreciated that a great variety of modifications have been made to DNA and RNA molecules that serve many useful purposes known to those of skill in the art. The term nucleic acid molecule as used herein embraces such chemically, enzymatically or metabolically modified forms of nucleic acid molecules, as well as the chemical forms of DNA and RNA characteristic of viruses and cells, including simple and complex cells, inter alia. The term nucleic acid molecule also encompasses short nucleic acid molecules often referred to as oligonucleotide(s). The terms "polynucleotide" and "nucleic acid" or "nucleic acid molecule" are used interchangeably herein.

The nucleic acids according to the present invention may be chemically synthesized. Alternatively, the nucleic acids can be isolated from *Borrelia* and modified by methods known to one skilled in the art. The same applies to the polypeptides according to the present invention.

Furthermore, the nucleic acid of the present invention can be functionally linked, using standard techniques such as cloning, to any desired sequence(s), whether a *Borrelia* regulatory sequence or a heterologous regulatory sequence, heterologous leader sequence, heterologous marker sequence or a heterologous coding sequence to create a fusion gene.

Nucleic acid molecules of the present invention may be in the form of RNA, such as mRNA or cRNA, or in the form of DNA, including, for instance, cDNA and genomic DNA obtained by cloning or produced by chemical synthesis techniques or by a combination thereof. The DNA may be triple-stranded, double-stranded or single-stranded. Single-stranded DNA may be the coding strand, also known as the sense strand, or it may be the non-coding strand, also referred to as the anti-sense strand.

The nucleic acid of the present invention may be comprised in a vector or in a host cell. Accordingly, the present invention also relates to a vector or a host cell, preferably *E. coli*, comprising a nucleic acid molecule according to the present invention. The vector may comprise the above-mentioned nucleic acid in such a manner that the vector is replicable and can express the protein encoded by the nucleotide sequence in a host cell.

For recombinant production of the polypeptides of the invention, host cells can be genetically engineered to incorporate expression systems or portions thereof of the nucleic acid of the invention. Introduction of a nucleic acid into a host cell can be effected by methods described in many standard laboratory manuals, such as Davis, et al., BASIC METHODS IN MOLECULAR BIOLOGY, (1986) and Sambrook, et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, conjugation, transduction, scrape loading, ballistic introduction and infection.

Representative examples of appropriate hosts include gram negative bacterial cells, such as cells of *E. coli, Acinetobacter, Actinobacillus, Bordetella, Brucella, Campylobacter, Cyanobacteria, Enterobacter, Erwinia, Franciscella, Helicobacter, Hemophilus, Klebsiella, Legionella, Moraxella, Neisseria, Pasteurella, Proteus, Pseudomonas, Salmonella, Serratia, Shigella, Treponema, Vibrio, Yersinia*. In one embodiment, the host cell is an *Escherichia coli* cell. In a preferred embodiment, the host cell is an *E. coli* BL21(DE3) cell or an *E. coli* BL21 Star™ (DE3) cell.

Alternatively, gram positive bacterial cells may also be used. A great variety of expression systems can be used to produce the polypeptides of the invention. In one embodiment the vector is derived from bacterial plasmids. Generally any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL (supra).

In one embodiment of the current invention, the cells are grown under selective pressure, such as in the presence of antibiotics, preferably kanamycin. In another embodiment, cells are grown in the absence of antibiotics.

A great variety of expression vectors can be used to express the polypeptides according to the present invention. Generally, any vector suitable to maintain, propagate or express nucleic acids to express a polypeptide in a host may be used for expression in this regard. In accordance with this aspect of the invention the vector may be, for example, a plasmid vector, a single- or double-stranded phage vector or a single- or double-stranded RNA or DNA viral vector. Starting plasmids disclosed herein are either commercially available, publicly available, or can be constructed from available plasmids by routine application of well-known, published procedures. Preferred among vectors, in certain respects, are those for expression of nucleic acid molecules and the polypeptides according to the present invention. Nucleic acid constructs in host cells can be used in a conventional manner to produce the gene product encoded by the recombinant sequence. Alternatively, the polypeptides according to the present invention can be synthetically produced by conventional peptide synthesizers.

In addition, the present invention relates to a host cell comprising this vector. Representative examples of appropriate host cells include bacteria, such as streptococci, staphylococci, *E. coli, Streptomyces* and *Bacillus subtilis*; fungi, such as yeast and *Aspergillus*; insect cells such as *Drosophila* S2 and *Spodoptera* Sf9 cells; mammalian cells such as CHO, COS, HeLa, C127, 3T3, BHK, 293 or Bowes melanoma cells; and plant cells. Cell-free translation systems can also be employed to produce such proteins using RNA derived from the DNA construct of the present invention.

In order to express the desired amino acid sequence practically by introducing the vector according to the present invention into a host cell, the vector may contain, in addition to the nucleic acid sequence according to the present invention, other sequences for controlling the expression (e.g., promoter sequences, terminator sequences and enhancer sequences) and gene markers for selecting microorganisms, insect cells, animal culture cells, or the like (e.g., neomycin resistance genes and kanamycin resistance genes). Furthermore, the vector may contain the nucleic acid sequence according to the present invention in a repeated form (e.g., in tandem). The vector may be constructed based on procedures which are conventionally used in the field of genetic engineering.

The host cells may be cultured in an appropriate medium, and the protein according to the present invention may be obtained from the culture product. The protein according to the present invention may be recovered from the culture medium and purified in the conventional manner.

Accordingly, the present invention also relates to a process for producing a cell which expresses a polypeptide according to the present invention, comprising transforming or transfecting a suitable host cell with the vector according to the present invention or a process for producing the polypeptide according to the present invention, comprising expressing the nucleic acid molecule according to the present invention.

Alternatively, a method for producing a polypeptide as defined above may be characterized by the following steps:
 a) introducing a vector encoding the polypeptide into a host cell,
 b) growing the host cell under conditions allowing for expression of said polypeptide,
 c) homogenizing said host cell, and
 d) subjecting the host cell homogenate to purification steps.

The invention further relates to a method for producing a polypeptide as defined above, characterized by the following steps:
 a) introducing a nucleic acid encoding a polypeptide into a vector,
 b) introducing said vector into a host cell,
 c) growing said host cell under conditions allowing for expression of polypeptide,
 d) homogenizing said host cell,
 e) enriching polypeptide in the lipid phase by phase separation, and
 f) further purifying over a gel filtration column.

The invention further relates to a method for producing a polypeptide as defined above, characterized by the following steps:
 a) introducing a nucleic acid encoding a polypeptide into a vector,
 b) introducing said vector into a host cell,
 c) growing said host cell under conditions allowing for expression of polypeptide,
 d) homogenizing said host cell,
 e) enriching polypeptide in the lipid phase by phase separation,
 g) purifying over a gel filtration column, and
 h) optionally, further processing over a buffer exchange column.

The Antibodies of the Invention and Related Aspects

The problem underlying the present invention is solved in a further aspect by an antibody, or at least an effective part thereof, which selectively binds to the hybrid C-terminal OspA fragment as defined in the context of the present invention, but not to the first OspA portion and the second OspA portion alone (i.e. if not fused to the other portion).

In a preferred embodiment the antibody is a monoclonal antibody.

In another preferred embodiment said effective part comprises an Fab fragment, an F(ab) fragment, an F(ab)N fragment, an F(ab)$_2$ fragment or an F$_v$ fragment or single domain antobody.

In still another embodiment of the invention the antibody is a chimeric antibody.

In yet another embodiment the antibody is a humanized antibody.

In a preferred aspect, antibodies of the invention bind specifically to hybrid OspA fragment polypeptides of the invention, but not to the first OspA portion and the second OspA portion alone and not to corresponding wild-type OspA fragment polypeptides. In a more preferred aspect, the antibody binds specifically to the disulfide bond of the mutant OspA fragment of the invention.

The term "specificity" refers to the number of different types of antigens or antigenic determinants to which a particular antigen-binding molecule or antigen-binding protein (such as a Nanobody or a polypeptide of the invention) can bind. The specificity of an antigen-binding protein can be determined based on affinity and/or avidity. The affinity, represented by the equilibrium constant for the dissociation of an antigen with an antigen-binding protein ($K_D$), is a measure for the binding strength between an antigenic determinant and an antigen-binding site on the antigen-binding protein: the lesser the value of the $K_D$, the stronger the binding strength between an antigenic determinant and the antigen-binding molecule (alternatively, the affinity can also be expressed as the affinity constant ($K_A$), which is $1/K_D$).

As will be clear to the skilled person (for example on the basis of the further disclosure herein), affinity can be determined in a manner known per se, depending on the specific antigen of interest. Avidity is the measure of the strength of binding between an antigen-binding molecule (such as an antibody or an effective part thereof of the invention) and the pertinent antigen. Avidity is related to both the affinity between an antigenic determinant and its antigen binding site on the antigen-binding molecule and the number of pertinent binding sites present on the antigen-binding molecule. Typically, antigen-binding proteins (such as an antibody or an effective part thereof of the invention) will bind to their antigen with a dissociation constant ($K_D$) of $10^{-5}$ to $10^{-12}$M or less, and preferably $10^{-7}$ to $10^{-12}$M or less and more preferably $10^{-8}$ to $10^{-12}$M (i.e. with an association constant ($K_A$) of $10^5$ to $10^{12}$ $M^1$ or more, and preferably $10^7$ to $10^{12}$ liter/moles or more and more preferably $10^8$ to $10^{12}$ $M^{-1}$). Any $K_D$ value greater than $10^4$ M (or any $K_A$ value lower than $10^4$ $M^{-1}$) is generally considered to indicate non-specific binding. Preferably, a monovalent immunoglobulin sequence of the invention will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art, as well as the other techniques mentioned herein.

The dissociation constant may be the actual or apparent dissociation constant, as will be clear to the skilled person. Methods for determining the dissociation constant will be clear to the skilled person, and for example include the techniques mentioned herein. In this respect, it will also be clear that it may not be possible to measure dissociation constants of more than $10^{-4}$ M or $10^{-3}$ M (e.g., of $10^{-2}$ M). Optionally, as will also be clear to the skilled person, the (actual or apparent) dissociation constant may be calculated on the basis of the (actual or apparent) association constant ($K_A$), by means of the relationship [$K_D=1/K_A$].

The affinity denotes the strength or stability of a molecular interaction. The affinity is commonly given as by the $K_D$, or dissociation constant, which has units of mole/liter (or M). The affinity can also be expressed as an association constant, $K_A$, which equals $1/K_D$ and has units of (liter/mole)$^{-1}$ (or $M^{-1}$). In the present specification, the stability of the interaction between two molecules (such as an amino acid sequence, Nanobody or polypeptide of the invention and its intended target) will mainly be expressed in terms of the $K_D$ value of their interaction; it being clear to the skilled person that in view of the relation $K_A=1/K_D$, specifying the strength of molecular interaction by its $K_D$ value can also be used to calculate the corresponding $K_A$ value. The $K_D$ value characterizes the strength of a molecular interaction also in a thermodynamic sense as it is related to the free energy (DG) of binding by the well known relation DG=RT·ln($K_D$) (equivalently DG=−RT·ln($K_A$)), where R equals the gas constant, T equals the absolute temperature and ln denotes the natural logarithm.

The $K_D$ for biological interactions which are considered meaningful (e.g. specific) are typically in the range of $10^{-10}$ M (0.1 nM) to $10^{-5}$ M (10000 nM). The stronger an interaction, the lower its $K_D$.

In a preferred embodiment, the $K_D$ of the antibody of the invention is between $10^{-12}$ M and $10^{-5}$ M, preferably less than $10^{-6}$, preferably less than $10^{-7}$, preferably less than $10^{-8}$ M, preferably less than $10^{-9}$ M, more preferably less than $10^{-10}$ M, even more preferably less than $10^{-11}$ M, most preferably less than $10^{-12}$ M.

The $K_D$ can also be expressed as the ratio of the dissociation rate constant of a complex, denoted as $k_{off}$, to the rate of its association, denoted $k_{on}$ (so that $K_D=k_{off}/k_{on}$ and $K_A=k_{on}/k_{off}$). The off-rate $k_{off}$ has units s$^{-1}$ (where s is the SI unit notation for second). The on-rate $k_{on}$ has units $M^{-1}S^{-1}$. The on-rate may vary between $10^2$ $M^{-1}$ s$^{-1}$ to about $10^7$ $M^{-1}s^{-1}$, approaching the diffusion-limited association rate constant for bimolecular interactions. The off-rate is related to the half-life of a given molecular interaction by the relation $t_{1/2}=\ln(2)/k_{off}$. The off-rate may vary between $10^{-6}$ s$^{-1}$ (near irreversible complex with a $t_{1/2}$ of multiple days) to 1 s$^{-1}$ ($t_{1/2}=0.69$ s).

The affinity of a molecular interaction between two molecules can be measured via different techniques known per se, such as the well known surface plasmon resonance (SPR) biosensor technique (see for example Ober et al., Intern Immunology, 13, 1551-1559, 2001) where one molecule is immobilized on the biosensor chip and the other molecule is passed over the immobilized molecule under flow conditions yielding $k_{on}$, $k_{off}$ measurements and hence $K_D$ (or $K_A$) values. This can for example be performed using the well-known BIACORE instruments.

It will also be clear to the skilled person that the measured $K_D$ may correspond to the apparent $K_D$ if the measuring process somehow influences the intrinsic binding affinity of the implied molecules for example by artefacts related to the coating on the biosensor of one molecule. Also, an apparent $K_D$ may be measured if one molecule contains more than one recognition site for the other molecule. In such situation the measured affinity may be affected by the avidity of the interaction by the two molecules.

Another approach that may be used to assess affinity is the 2-step ELISA (Enzyme-Linked Immunosorbent Assay) procedure of Friguet et al. (J. Immunol Methods, 77, 305-19, 1985). This method establishes a solution phase binding equilibrium measurement and avoids possible artefacts relating to adsorption of one of the molecules on a support such as plastic.

However, the accurate measurement of $K_D$ may be quite labor-intensive; therefore, apparent $K_D$ values are often determined in order to assess the binding strength of two molecules. It should be noted that as long as all measurements are made in a consistent way (e.g. keeping the assay conditions unchanged), apparent $K_D$ measurements can be used as an approximation of the true $K_D$ and hence in the present document $K_D$ and apparent $K_D$ should be treated with equal importance or relevance.

Finally, it should be noted that in many situations the experienced scientist may judge it to be convenient to determine the binding affinity relative to some reference molecule. For example, to assess the binding strength between molecules A and B, one may e.g. use a reference molecule C that is known to bind to B and that is suitably labelled with a fluorophore or chromophore group or other chemical moiety, such as biotin for easy detection in ELISA or flow cytometry or other format (the fluorophore for fluorescence detection, the chromophore for light absorption detection, the biotin for streptavidin-mediated ELISA detection). Typically, the reference molecule C is kept at a fixed concentration and the concentration of A is varied for a given concentration or amount of B. As a result an Inhibitory Concentration ($IC_{50}$) value is obtained corresponding to the concentration of A at which the signal measured for C in absence of A is halved. Provided $K_{D\ ref}$, the $K_D$ of the reference molecule, is known, as well as the total concentration $c_{ref}$ of the reference molecule, the apparent $K_D$ for the interaction A-B can be obtained from following formula: $K_D=IC_{50}/(1+c_{ref}/K_{Dref})$. Note that if $c_{ref} \ll K_{Dref}$, $K_D \approx IC_{50}$. Provided the measurement of the $IC_{50}$ is performed in a consistent way (e.g. keeping $c_{ref}$ fixed) for the binders that are compared, the strength or stability of a molecular interaction can be assessed by the $IC_{50}$ and this measurement is judged as equivalent to $K_D$ or to apparent $K_D$ throughout this text.

Another aspect of the invention relates to a hybridoma cell line, which produces an antibody as defined above.

The problem underlying the present invention is furthermore solved by a method for producing an antibody as defined above, characterized by the following steps:
a) initiating an immune response in a non-human animal by administering a polypeptide as defined above to said animal,
b) removing an antibody containing body fluid from said animal, and
c) producing the antibody by subjecting said antibody containing body fluid to further purification steps.

The invention further relates to a method for producing an antibody as defined above, characterized by the following steps:
a) initiating an immune response in a non-human animal by administering a polypeptide as defined above to said animal,
b) removing the spleen or spleen cells from said animal,
c) producing hybridoma cells of said spleen or spleen cells,
d) selecting and cloning hybridoma cells specific for said polypeptide,
e) producing the antibody by cultivation of said cloned hybridoma cells, and
f) optionally conducting further purification steps.

Pharmaceutical Compositions and Related Medical Aspects

Another aspect of the present invention is related to a pharmaceutical composition comprising
(i) the polypeptide according to the present invention, the nucleic acid according to the present invention, and/or the antibody according to the present invention; and
(ii) optionally a pharmaceutically acceptable excipient.

Accordingly, the polypeptide according to the present invention, the nucleic acid according to the present invention, the antibody according to the present invention or the pharmaceutical composition according to the present invention may be
for use as a medicament, particularly as a vaccine or
for use in a method of treating or preventing a Borrelia infection, particularly a B. burgdorferi s.s., B. garinii, B. afzelii, B. andersoni, B. bavariensis, B. bissettii, B. valaisiana, B. lusitaniae, B. spielmanii, B. japonica, B. tanukii, B. turdi or B. sinica infection, preferably a B. burgdoiferi s.s., B. afzelii or B. garinii infection.

Preferably, the composition additionally comprises Lip-S1D1-S2D1 (SEQ ID NO: 29) and Lip-S5D1-S6D1 (SEQ ID NO: 33), the composition additionally comprises Lip-S1D1-S2D1 (SEQ ID NO: 29), the composition additionally comprises Lip-S5D1-S6D1 (SEQ ID NO: 33), or the composition comprises Lip-S1D1-S2D1 (SEQ ID NO: 29), Lip-S4D1-S3hybD1 (SEQ ID NO: 27) and Lip-S5D1-S6D1 (SEQ ID NO: 33).

Still another aspect relates to a pharmaceutical composition as defined above for use in the treatment or prevention of an infection with Borrelia species, more preferably pathogenic Borrelia species as disclosed herein more preferably comprising B. burgdorferi s.s., B. afzelii, B. bavariensis and B. garinii.

The problem underlying the present invention is solved in another aspect by the use of the polypeptide according to the present invention, the nucleic acid according to the present invention, and/or the antibody according to the present invention for the preparation of a pharmaceutical composition for treating or preventing infections with Borrelia species, more preferably pathogenic Borrelia species as disclosed herein more preferably comprising B. burgdorferi s.s., B. afzelii, B. bavariensis and B. garinii.

The pharmaceutical composition may optionally contain any pharmaceutically acceptable carrier or excipient, such as buffer substances, stabilisers or further active ingredients, especially ingredients known in connection with pharmaceutical compositions and/or vaccine production. Preferably, the pharmaceutically acceptable excipient comprises L-methionine. Preferably, the pharmaceutical composition is for use as a medicament, particularly as a vaccine or for preventing or treating an infection caused by Borrelia species, more preferably pathogenic Borrelia species as disclosed herein more preferably comprising B. burgdorferi s.s., B. afzelii, B. bavariensis and B. garinii, and/or other pathogens against which the antigens have been included in the vaccine. Preferably, the pharmaceutical composition is for use in a method of treating or preventing a Borrelia infection, particularly a B. burgdoiferi s.s., B. garinii, B. afzelii, B. andersoni, B. bavariensis, B. bissettii, B. valaisiana, B. lusitaniae, B. spielmanii, B. japonica, B. tanukii, B. turdi or B. sinica infection, preferably a B. burgdoiferi s.s., B. afzelii or B. garinii infection.

In one embodiment the pharmaceutical composition further comprises an adjuvant. The choice of a suitable adjuvant to be mixed with bacterial toxins or conjugates made using the processes of the invention is within the knowledge of the person skilled in the art. Suitable adjuvants include an aluminium salt such as aluminium hydroxide or aluminum phosphate, but may also be other metal salts such as those of calcium, magnesium, iron or zinc, or may be an insoluble suspension of acylated tyrosine, or acylated sugars, cationically or anionically derivatized saccharides, or polyphosphazenes. In a preferred embodiment, the pharmaceutical composition is adjuvanted with aluminium hydroxide.

In a further embodiment, the pharmaceutical composition further comprises an immunostimulatory substance, preferably selected from the group consisting of polycationic polymers, especially polycationic peptides, immunostimulatory oligodeoxynucleotides (ODNs), especially oligo (dIdC)$_{13}$ (SEQ ID NO: 63), peptides containing at least two LysLeuLys motifs, especially peptide KLKLLLLLKLK (SEQ ID NO: 61), neuroactive compounds, especially human growth hormone, aluminium hydroxide, aluminium phosphate, Freund's complete or incomplete adjuvants, or combinations thereof. Preferably, the immunostimulatory substance is a combination of either a polycationic polymer and immunostimulatory deoxynucleotides or of a peptide containing at least two LysLeuLys motifs and immunostimulatory deoxynucleotides, preferably a combination of KLKLLLLLKLK (SEQ ID NO: 61) and oligo(dIdC)$_{13}$ (SEQ ID NO: 63). More preferably, said polycationic peptide is polyarginine.

In a further embodiment, the pharmaceutical composition comprises sodium phosphate, sodium chloride, L-methionine, sucrose and Polysorbate-20 (Tween-20) at a pH of 6.7+/−0.2. Preferably, the pharmaceutical composition also comprises aluminium hydroxide, preferably at a concentration of 0.15%.

In one embodiment, the formulation comprises between 5 mM and 50 mM sodium phosphate, between 100 and 200 mM sodium chloride, between 5 mM and 25 mM L-Methionine, between 2.5% and 10% Sucrose, between 0.01% and 0.1% Tween 20 and between 0.1% and 0.2% (w/v) aluminium hydroxide. More preferably, the formulation comprises 10 mM sodium phosphate, 150 mM sodium chloride, 10 mM L-Methionine, 5% Sucrose, 0.05% Tween 20 and 0.15% (w/v) aluminium hydroxide at pH 6.7±0.2. Even more preferably, the formulation comprises at least one, at least two, at least three mutant OspA heterodimers according to the invention.

In one embodiment, the pharmaceutical composition comprises 3 heterodimers, preferably Lip-S1D1-S2D1 (SEQ ID NO: 29), Lip-S4D1-S3hybD1 (SEQ ID NO: 27) and Lip-S5D1-S6D1 (SEQ ID NO: 33). Preferably, the three heterodimers are mixed at a molar ratio of 1:2:1, 1:3:1, 1:1:2, 1:1:3, 1:2:2, 1:2:3, 1:3:2, 1:3:3, 2:1:1, 2:1:2, 2:1:3, 2:2:3, 2:2:1, 2:3:1, 2:3:2, 2:3:3, 3:1:1, 3:1:2, 3:1:3, 3:2:1, 3:2:2, 3:2:3, 3:3:1, 3:3:2, most preferably 1:1:1.

In a further embodiment, the pharmaceutical composition comprises two heterodimers, preferably Lip-S1D1-S2D1 (SEQ ID NO: 29) and Lip-S5D1-S6D1 (SEQ ID NO: 33), Lip-S1D1-S2D1 (SEQ ID NO: 29) and Lip-S4D1-S3hybD1 (SEQ ID NO: 27) or Lip-S4D1-S3hybD1 (SEQ ID NO: 27) and Lip-S5D1-S6D1 (SEQ ID NO: 33) in a molar ratio of 1:2, 1:3, 2:1, 3:1, 2:3, 3:2, preferably 1:1.

In one embodiment the pharmaceutical composition or vaccine of the invention further comprises at least one additional antigen from *Borrelia* or a pathogen other than *Borrelia* (herein referred to generically as "combination pharmaceutical composition or vaccine"). In a preferred embodiment, the at least one additional antigen is derived from a *Borrelia* species causing Lyme borreliosis. In various aspects, the at least one additional antigen is derived from another pathogen, preferably a tick-borne pathogen. In a further aspect, the pathogen causes Rocky Mountain spotted fever, Human granulocytic ehrlichiosis (HGE), *Sennetsu* Fever, Human Monocytic Ehrlichiosis (HME), Anaplasmosis, Boutonneuse fever, *Rickettsia parkeri* Rickettsiosis, Southern Tick-Associated Rash Illness (STARI), Helvetica Spotted fever, 364D Rickettsiosis, African spotted fever, Relapsing fever, Tularemia, Colo. tick fever, Tick-borne encephalitis (TBE, also known as FSME), Crimean-Congo hemorrhagic fever, Q fever, Omsk hemorrhagic fever, Kyasanur forest disease, Powassan encephalitis, Heartland virus disease or Babesiosis. In a further aspect, the disease is Japanese encephalitis.

In a further embodiment, the at least one additional antigen is derived from a vector-borne, preferably a tick-borne, pathogen selected from the group comprising *Borrelia hermsii, Borrelia parkeri, Borrelia duttoni, Borrelia miyamotoi, Borrelia turicatae, Rickettsia rickettsii, Rickettsia australis, Rickettsia conori, Rickettsia helvetica, Francisella tularensis, Anaplasma phagocytophilum, Ehrlichia sennetsu, Ehrlichia chaffeensis, Neoehrlichia mikurensis, Coxiella burnetii* and *Borrelia lonestari*, Tick-borne encephalitis virus (TBEV aka FSME virus), Colorado tick fever virus (CTFV), Crimean-Congo hemorrhagic fever virus (CCHFV), Omsk Hemorrhagic Fever virus (OHFV), Japanese encepalitis virus (JEV) and *Babesia* spp.

In another aspect, the invention relates to a kit comprising the pharmaceutical composition of the present invention and an additional antigen as defined above, wherein the at least one additional antigen is comprised in a second composition, particularly wherein the second composition is a vaccine, preferably a tick-borne encephalitis vaccine, a Japanese encephalitis vaccine or a Rocky Mountain spotted fever vaccine. The first composition may be a vaccine as well. The combination pharmaceutical composition or vaccine of the invention comprises any composition discussed herein in combination with at least a second (vaccine) composition. In some aspects, the second vaccine composition protects against a vector-borne disease, preferably a tick-borne disease. In various aspects, the second vaccine composition has a seasonal immunization schedule compatible with immunization against *Borrelia* infection or Lyme borreliosis. In other aspects, combination vaccines are useful in the prevention of multiple diseases for use in geographical locations where these diseases are prevalent.

In one aspect, the second composition is a vaccine selected from the group consisting of a tick-borne encephalitis vaccine, a Japanese encephalitis vaccine, and a Rocky Mountain Spotted Fever vaccine. In a preferred aspect, the vaccine composition is FSME-IMMUN® (Baxter), Encepur® (Novartis Vaccines), EnceVir® (Microgen NPO) or TBE Moscow Vaccine® (Chumakov Institute of Poliomyelitis and Viral Encephalitides of Russian Academy of Medical Sciences). In another preferred aspect, the vaccine composition is IXIARO®/JESPECT® (Valneva SE), JEEV® (Biological E, Ltd.) or IMOJEV® (Sanofi Pasteur).

There is further provided a pharmaceutical composition which is a vaccine, this vaccine may further comprise a pharmaceutically acceptable excipient. In a preferred embodiment, the excipient is L-methionine.

The invention also includes immunogenic compositions. In some aspects, an immunogenic composition of the invention comprises any of the compositions discussed herein and a pharmaceutically acceptable carrier. In various aspects, the immunogenic composition has the property of inducing production of an antibody that specifically binds an outer surface protein A (OspA) protein. In certain aspects, the immunogenic composition has the property of inducing production of an antibody that specifically binds *Borrelia*. In particular aspects, the immunogenic composition has the property of inducing production of an antibody that neutralizes *Borrelia*. In some aspects, the antibody is produced by an animal. In further aspects, the animal is a mammal. In even further aspects, the mammal is human.

The vaccine preparations containing pharmaceutical compositions of the present invention may be used to protect a mammal susceptible to *Borrelia* infection or treat a mammal with a *Borrelia* infection, by means of administering said vaccine via a systemic or mucosal route. These administrations may include injection via the intramuscular, intraperitoneal, intradermal or subcutaneous routes; or via mucosal administration to the oral/alimentary, respiratory or genitourinary tracts. Although the vaccine of the invention may be administered as a single dose, components thereof may also be co-administered together at the same time or at different times.

In one aspect of the invention is provided a vaccine kit, comprising a vial containing a pharmaceutical composition of the invention, optionally in lyophilised form, and further comprising a vial containing an adjuvant as described herein. It is envisioned that in this aspect of the invention, the adjuvant will be used to reconstitute the lyophilised immunogenic composition. In a further aspect, the pharmaceutical composition of the invention may be pre-mixed in a vial, preferably in a syringe.

A further aspect of the invention is a method of treating or preventing a *Borrelia* infection in a subject in need thereof comprising the step of administering to the subject a therapeutically-effective amount of a polypeptide of the present invention, the nucleic acid of the present invention, the antibody of the present invention or the pharmaceutical composition of the present invention.

A further aspect of the invention is a method of immunizing a subject in need thereof comprising the step of administering to the subject a therapeutically-effective amount of a polypeptide of the present invention, the nucleic acid of the present invention, the antibody of the present invention or the pharmaceutical composition of the present invention.

A still further aspect relates to a method for immunizing an animal or human against infection with a *Borrelia* organism, comprising the step of administering to said animal or human an effective amount a polypeptide of the present invention, the nucleic acid of the present invention, the antibody of the present invention or the pharmaceutical composition of the present invention, wherein the effective amount is suitable to elicit an immune response in said animal or human.

Yet another aspect relates to a method for stimulating an immune response in an animal or human against a *Borrelia* organism, comprising the step of administering to said animal or human an effective amount of a polypeptide of the present invention, the nucleic acid of the present invention, the antibody of the present invention or the pharmaceutical composition of the present invention, wherein the effective amount is suitable to stimulate an immune response in said animal or human.

Preferably, the *Borrelia* organism is selected from the group comprising *B. burgdorferi*, particularly *B. burgdorferi* s.s., *B. garinii*, *B. afzelii*, *B. andersoni*, *B. bavariensis*, *B. bissettii*, *B. valaisiana*, *B. lusitaniae*, *B. spielmanii*, *B. japonica*, *B. tanukii*, *B. turdi* or *B. sinica*, preferably *B. burgdorferi* s.s., *B. afzelii* or *B. garinii*.

In one embodiment there is provided a method of preventing or treating primary and/or recurring episodes of *Borrelia* infection comprising administering to the host an immunoprotective dose of the pharmaceutical composition or vaccine or kit of the invention.

A further aspect of the invention is a pharmaceutical composition of the invention for use in the treatment or prevention of Borrelial disease. In one embodiment there is provided a pharmaceutical composition for use in the treatment or prevention of *Borrelia* infection.

A further aspect of the invention is the use of the pharmaceutical composition or vaccine or kit of the invention in the manufacture of a medicament for the treatment or prevention of *Borrelia* infection. In one embodiment there is provided a pharmaceutical composition of the invention for use in the manufacture of a medicament for the treatment or prevention of *Borrelia* infection.

The invention also includes methods for inducing an immunological response in a subject. In various aspects, such methods comprise the step of administering any of the immunogenic compositions or vaccine compositions discussed herein to the subject in an amount effective to induce an immunological response. In certain aspects, the immunological response comprises production of an anti-OspA antibody.

The invention includes methods for preventing or treating a *Borrelia* infection or Lyme boreliosis in a subject. In various aspects, such methods comprise the step of administering any of the vaccine compositions discussed herein or any of the combination vaccines discussed herein to the subject in an amount effective to prevent or treat the *Borrelia* infection or Lyme borreliosis.

The invention includes uses of polypeptides, nucleic acids, antibodies, pharmaceutical compositions or vaccines of the invention for the preparation of medicaments. Other related aspects are also provided in the instant invention.

The terms "comprising", "comprise" and "comprises" herein are intended by the inventors to be optionally substitutable with the terms "consisting of", "consist of" and "consists of", respectively, in every instance. The term "comprises" means "includes". Thus, unless the context requires otherwise, the word "comprises", and variations such as "comprise" and "comprising" will be understood to imply the inclusion of a stated compound or composition (e.g., nucleic acid, polypeptide, antibody) or step, or group of compounds or steps, but not to the exclusion of any other compounds, composition, steps, or groups thereof. The abbreviation, "e.g." is derived from the Latin exempli gratia, and is used herein to indicate a non-limiting example. Thus, the abbreviation "e.g." is synonymous with the term "for example".

Embodiments herein relating to "vaccine compositions" of the invention are also applicable to embodiments relating to "pharmaceutical compositions" of the invention, and vice versa.

Unless otherwise explained, all technical and scientific terms used herein have the same meaning as commonly understood by one of ordinary skill in the art to which this disclosure belongs. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The singular terms "a", "an", and "the" include plural referents unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values given for nucleic acids or polypeptides are approximate, and are provided for description. Additionally, numerical limitations given with respect to concentrations or levels of a substance, such as an antigen, may be approximate.

A preferable carrier or excipient for the polypeptides according to the present invention in their diverse embodiments, or a nucleic acid molecule according to the present invention is an immunostimulatory compound such as an adjuvant for further stimulating the immune response to the polypeptide according to the present invention or a coding nucleic acid molecule thereof.

Adjuvants or immunostimulatory compounds may be used in compositions of the invention. Preferably, the immunostimulatory compound in pharmaceutical compositions according to the present invention is selected from the group of polycationic substances, especially polycationic peptides, immunostimulatory nucleic acids molecules, preferably immunostimulatory deoxynucleotides, oil-in-water or water-in-oil emulsions, MF59, aluminium salts, Freund's complete adjuvant, Freund's incomplete adjuvant, neuroactive compounds, especially human growth hormone, or combinations thereof.

The use of an aluminium hydroxide and/or aluminium phosphate adjuvant is particularly preferred, and antigens are generally adsorbed to these salts. Preferably, aluminium hydroxide is present at a final concentration of 0.15%. A useful aluminium phosphate adjuvant is amorphous aluminium hydroxyphosphate with $PO_4$/Al molar ratio between 0.84 and 0.92. Another adjuvant useful in the current invention is an aluminium salt that is able to provide an aqueous composition having less than 350 ppb heavy metal based on the weight of the aqueous composition. A further useful aluminium-based adjuvant is AS04, a combination of aluminium hydroxide and monophosphoryl lipid A (MPL).

Also, the pharmaceutical composition in accordance with the present invention is a pharmaceutical composition which comprises at least any of the following compounds or combinations thereof: the nucleic acid molecules according to the present invention, the polypeptides according to the present invention in their diverse embodiments, the vector according to the present invention, the cells according to the present invention and the antibody according to the present invention. In connection therewith, any of these compounds may be employed in combination with a non-sterile or sterile carrier or carriers for use with cells, tissues or organisms, such as a pharmaceutical carrier suitable for administration to a subject. Such carriers may include, but are not limited to, saline, buffered saline, dextrose, water, glycerol, ethanol and combinations thereof. The formulation should suit the mode of administration.

In one embodiment, the pharmaceutical composition comprises a stabilizer. The term "stabilizer" refers to a substance or vaccine excipient which protects the immunogenic composition of the vaccine from adverse conditions, such as those which occur during heating or freezing, and/or prolongs the stability or shelf-life of the immunogenic composition in a stable and immunogenic condition or state. Examples of stabilizers include, but are not limited to, sugars, such as sucrose, lactose and mannose; sugar alcohols, such as manitol; amino acids, such as glycine or glutamic acid; and proteins, such as human serum albumin or gelatin.

The pharmaceutical compositions of the present invention may be administered in any effective, convenient manner including, for instance, administration by topical, oral, anal, vaginal, intravenous, intraperitoneal, intramuscular, subcutaneous, intranasal, intratracheal or intradermal routes, among others. In a preferred embodiment, the pharmaceutical compositions are administered subcutaneously or intramuscularly, most preferably intramuscularly.

In therapy or as a prophylactic, the active agent of the pharmaceutical composition of the present invention may be administered to an individual as an injectable composition, for example as a sterile aqueous dispersion, preferably isotonic.

Alternatively the composition, preferably the pharmaceutical composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

In a preferred embodiment the pharmaceutical composition is a vaccine composition. Preferably, such vaccine composition is conveniently in injectable form. Conventional adjuvants may be employed to enhance the immune response. A suitable unit dose for vaccination with a protein antigen is for adults between 0.02 µg and 3 µg antigen per kg body weight and for children between 0.2 µg and 10 µg antigen per kg body weight, and such dose is preferably administered 1 to 3 times at intervals of 2 to 24 weeks.

At the indicated dose range, no adverse toxicological effects are expected with the compounds of the invention, which would preclude their administration to suitable individuals.

As an additional aspect, the invention includes kits which comprise one or more pharmaceutical formulations for administration to a subject packaged in a manner which facilitates their use for administration to subjects. In a preferred embodiment, the kits comprise the formulation in a final volume of 2 mL, more preferably in a final volume of 1 mL.

In a specific embodiment, the invention includes kits for producing a single dose administration unit. The kits, in various aspects, each contain both a first container having a dried protein and a second container having an aqueous formulation. Also included within the scope of this invention are kits containing single and multi-chambered pre-filled syringes (e.g., liquid syringes and lyosyringes).

In another embodiment, such a kit includes a pharmaceutical formulation described herein (e.g., a composition comprising a therapeutic protein or peptide), packaged in a container such as a sealed bottle or vessel, with a label affixed to the container or included in the package that describes use of the compound or composition in practicing the method. In one embodiment, the pharmaceutical formulation is packaged in the container such that the amount of headspace in the container (e.g., the amount of air between the liquid formulation and the top of the container) is very small. Preferably, the amount of headspace is negligible (i.e., almost none).

In one aspect, the kit contains a first container having a therapeutic protein or peptide composition and a second container having a physiologically acceptable reconstitution solution for the composition. In one aspect, the pharmaceutical formulation is packaged in a unit dosage form. The kit optionally further includes a device suitable for administering the pharmaceutical formulation according to a specific route of administration. In some aspects, the kit contains a label that describes use of the pharmaceutical formulations.

The pharmaceutical composition can contain a range of different antigens. Examples of antigens are whole-killed or attenuated organisms, subtractions of these organisms, proteins, or, in their most simple form, peptides. Antigens can also be recognized by the immune system in the form of glycosylated proteins or peptides and may also be or contain polysaccharides or lipids. Short peptides can be used, since cytotoxic T cells (CTL) recognize antigens in the form of short, usually 8-11 amino acid long, peptides in conjunction with major histocompatibility complex (MHC). B cells can recognize linear epitopes as short as 4 to 5 amino acids, as well as three-dimensional structures (conformational epitopes).

In a preferred embodiment, the pharmaceutical composition of another aspect additionally comprises a hyperimmune serum-reactive antigen against a *Borrelia* protein or an active fragment or variant thereof, such as, e.g., the antigens, fragments and variants as described in WO2008/031133.

According to the invention, the pharmaceutical composition according to another aspect may be used as a medicament, particularly as a vaccine, particularly in connection with a disease or disease condition which is caused by, linked or associated with *Borrelia*.

The pharmaceutical composition of the present invention may be used as a medicament, particularly as a vaccine, particularly in connection with a disease or disease condition which is caused by, linked with or associated with *Borrelia*, more preferably any pathogenic *Borrelia* species and more preferably in a method for treating or preventing a *Borrelia* infection, particularly a *B. burgdorferi* s.s., *B. garinii*, *B. afzelii*, *B. andersoni*, *B. bavariensis*, *B. bissettii*, *B. valaisiana*, *B. lusitaniae*, *B. spielmanii*, *B. japonica*, *B. tanukii*, *B. turdi* or *B. sinica* infection, preferably a *B. burgdorferi* s.s., *B. afzelii* or *B. garinii* infection.

In connection therewith, it should be noted that the various *Borrelia* species, including *B. burgdorferi* s.l., comprise several species and strains including those disclosed herein. A disease related, caused or associated with the bacterial infection to be prevented and/or treated according to the present invention includes Lyme borreliosis (Lyme disease). Further aspects, symptoms, stages and subgroups of Lyme borreliosis as well as specific groups of patients suffering from such disease as also disclosed herein, including in the introductory part, are incorporated herein by reference. More specifically, Lyme borreliosis generally occurs in stages, with remission and exacerbations with different clinical manifestation at each stage. Early infection stage 1 consists of localized infection of the skin, followed within days or weeks by stage 2, disseminated infection, and months to years later by stage 3, persistent infection. However, the infection is variable; some patients have only localized infections of the skin, while others display only later manifestations of the illness, such as arthritis.

In a fourth aspect, the present invention relates to a method of treating or preventing a *Borrelia* infection in a subject in need thereof, comprising the step of administering to the subject a therapeutically effective amount of a pharmaceutical composition according to the third aspect.

The term "subject" is used throughout the specification to describe an animal, preferably a mammal, more preferably a human, to whom a treatment or a method according to the present invention is provided. For treatment of those infections, conditions or disease states which are specific for a specific animal such as a human patient, the term patient refers to that specific animal Preferably, the subject is a human; however, the medical use of the composition may also include animals such as poultry including chicken, turkey, duck or goose, livestock such as horse, cow or sheep, or companion animals such as dogs or cats.

The term "effective amount" is used throughout the specification to describe an amount of the present pharmaceutical composition which may be used to induce an intended result when used in the method of the present invention. In numerous aspects of the present invention, the term effective amount is used in conjunction with the treatment or prevention. In other aspects, the term effective amount simply refers to an amount of an agent which produces a result which is seen as being beneficial or useful, including in methods according to the present invention where the treatment or prevention of a *Borrelia* infection is sought.

The term effective amount with respect to the presently described compounds and compositions is used throughout the specification to describe that amount of the compound according to the present invention which is administered to a mammalian patient, especially including a human patient, suffering from a *Borrelia*-associated disease, to reduce or inhibit a *Borrelia* infection.

In a preferred embodiment, the method of immunizing a subject according to the above aspect comprises the step of administering to the subject a therapeutically effective amount of a pharmaceutical composition of the third aspect of the current invention.

The method comprises inducing an immunological response in an individual through gene therapy or otherwise, by administering a polypeptide or nucleic acid according to the present invention in vivo in order to stimulate an immunological response to produce antibodies or a cell-mediated T cell response, either cytokine-producing T cells or cytotoxic T cells, to protect said individual from disease, whether or not that disease is already established within the individual.

The products of the present invention, particularly the polypeptides and nucleic acids, are preferably provided in isolated form, and may be purified to homogeneity. The term "isolated" as used herein means separated "by the hand of man" from its natural state; i.e., if it occurs in nature, it has been changed or removed from its original environment, or both. For example, a naturally-occurring nucleic acid molecule or a polypeptide naturally present in a living organism in its natural state is not "isolated", but the same nucleic acid molecule or polypeptide separated from the coexisting materials of its natural state is "isolated", as the term is employed herein. As part of or following isolation, such nucleic acid molecules can be joined to other nucleic acid molecules, such as DNA molecules, for mutagenesis, to form fusion genes, and for propagation or expression in a host, for instance. The isolated nucleic acid molecules, alone or joined to other nucleic acid molecules such as vectors, can be introduced into host cells, in culture or in whole organisms. Introduced into host cells in culture or in whole organisms, such DNA molecules still would be isolated, as the term is used herein, because they would not be in their naturally-occurring form or environment. Similarly, the nucleic acid molecules and polypeptides may occur in a composition, such as medium formulations, solutions for introduction of nucleic acid molecules or polypeptides, for example, into cells, compositions or solutions for chemical or enzymatic reactions, for instance, which are not naturally occurring compositions, and, therein remain isolated nucleic acid molecules or polypeptides within the meaning of that term as it is employed herein.

The invention is not limited to the particular methodology, protocols and reagents described herein because they may vary. Furthermore, the terminology used herein is for the purpose of describing particular embodiments only and is not intended to limit the scope of the present invention. As used herein and in the appended claims, the singular forms "a", "an", and "the" include plural reference unless the context clearly dictates otherwise. Similarly, the words "comprise", "contain" and "encompass" are to be interpreted inclusively rather than exclusively.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the preferred methods, and materials are described herein.

The present invention is further illustrated by the following Figures, Tables, Examples and the Sequence listing, from which further features, embodiments and advantages may be taken. As such, the specific modifications discussed are not to be construed as limitations on the scope of the invention. It will be apparent to the person skilled in the art that various equivalents, changes, and modifications may be made without departing from the scope of the invention, and it is thus to be understood that such equivalent embodiments are to be included herein.

In connection with the present invention

FIG. 1 shows electrostatic potential isocontours of disulfide-bond-stabilized fragments of serotype 1-serotype 6 and *B. valaisiana* OspA (S1D1-S6D1 and BvaD1), as well as the mutant fusion OspA fragment of the invention consisting of amino acids 125-176 of *B. valaisiana*, strain VS116, and amino acids 177-274 of *B. garinii*, strain PBr, with an introduced disulfide bond (S3hybD1).

FIG. 2 shows the amino acid alignment of Lip-S4D1-S3hybD1, the mutant serotype 3 OspA fusion fragment-containing heterodimer protein of the invention, with the heterodimer protein Lip-S4D1-S3D1.

FIG. 3 schematically shows the production of mutant OspA fragment heterodimers according to the current invention.

FIG. 4 schematically represents the polypeptide components of a pharmaceutical composition of the current invention, an "improved combination vaccine", comprising three different mutant OspA heterodimers, including Lip-S4D1-S3hybD1.

FIG. 5 shows the chemical structure of Pam$_3$Cys, an example of a fatty acid substituted cysteine, such as would be found at the N-terminus of lipidated polypeptides of the current invention.

Table 1 compares the purification yield of the Lip-S4D1-S3hybD1 heterodimer and the Lip-S4D1-S3D1 heterodimer Table 2 shows the protective capacity of the improved heterodimer combination vaccine of the invention against in vivo challenge with OspA serotypes 1, 2, 5 and 6 *Borrelia*.

The figures and tables which may be referred to in the specification are described below in more detail.

Figure 1:
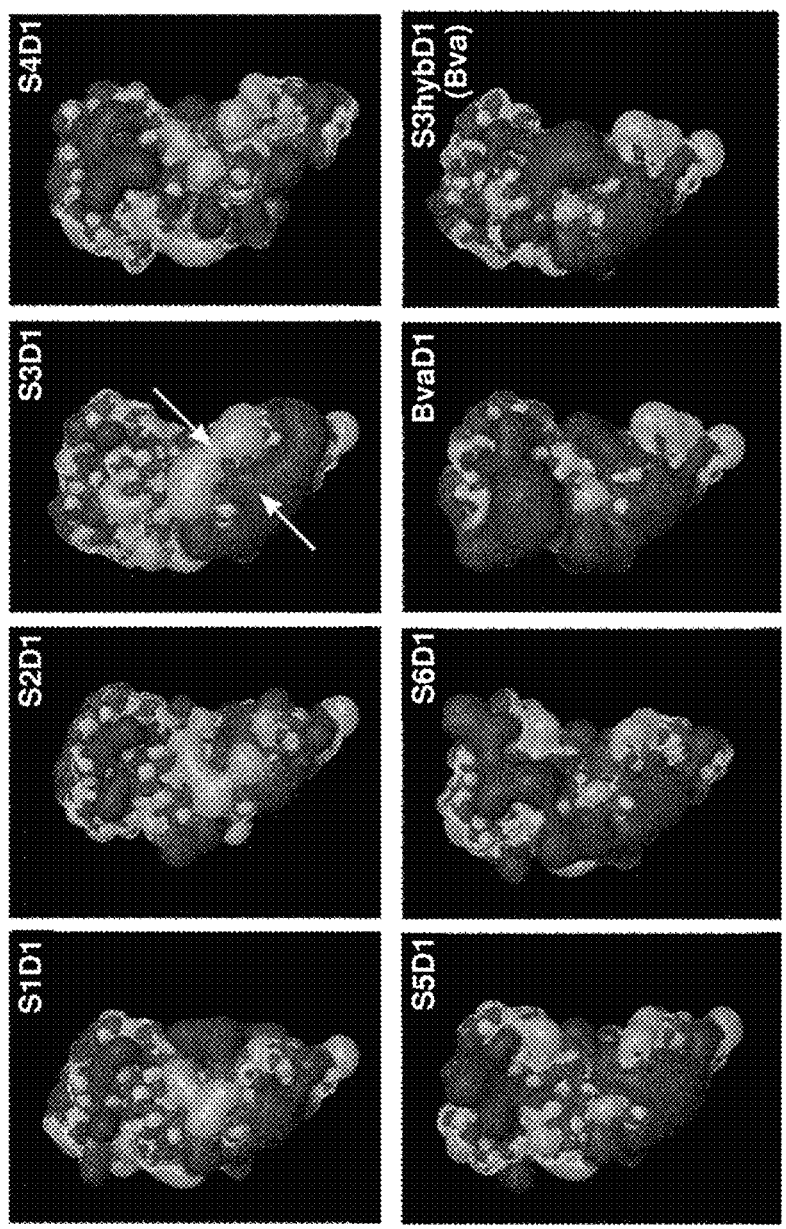

FIG. 1 Electrostatic potential simulation of the disulfide-bond-stabilized OspA fragments from serotypes 1-6 (S1D1-S6D1) and *B. valaisiana* (BvaD1) as well as the disulfide-bond-stabilized fusion OspA fragment (S3hybD1). Isocontours (+/−1 kT/e) are colored bright for negative charges and dark for positive charges, as a solid surface. The solvent-accessible surface is rendered as a wireframe. The white arrows indicate the position of the two extended clusters giving rise to electrostatic polarity on the same plane of the serotype 3 fragment. It can be seen that the surfaces of the hybrid OspA C-terminal fragment do not possess the extended electrostatic polar clusters as the S3D1 monomer.

FIG. 2 Amino acid sequence alignment of Lip-S4D1-S3hybD1 and Lip-S4D1-S3D1 heterodimer polypeptides, showing the consensus sequence. The Lip-S4D1-S3hybD1 heterodimer differs from the Lip-S4D1-S3D1 heterodimer by only 31 amino acids in total.

FIG. 3 Production of a mutant OspA heterodimer of the invention comprising two mutant OspA C-terminal fragments selected from different OspA serotypes of *Borrelia* sp. or a hybrid mutant OspA C-terminal fragment (A) Schematic representation of a nucleic acid encoding a lipidated mutant OspA heterodimer. The components, from 5' to 3', comprise the coding sequences for a lipidation signal sequence (Lip signal), a CSS peptide for N-terminal lipidation, a mutant C-terminal fragment of OspA with two non-native cysteines, a short linker peptide (LN1), followed by a second mutant OspA C-terminal fragment with two non-native cysteines. (B) The intermediate mutant OspA heterodimer polypeptide comprises the nascent product directly following translation of the nucleic acid construct. From the N- to the C-terminus, this polypeptide consists of a lipidation signal sequence (Lip signal), a CSS peptide for lipidation, a mutant OspA fragment with a non-native disulfide bond, a short linker peptide (LN1), followed by a second mutant OspA fragment with a non-native disulfide bond. (C) The final lipidated mutant OspA heterodimer polypeptide after post-translational modification. The heterodimer, from the N- to the C-terminus, consists of a CSS peptide with the N-terminal cysteine lipidated, a mutant OspA fragment stabilized by a disulfide bond, a linker peptide (LN1), and a second mutant OspA fragment stabilized by a disulfide bond. The lipidation signal sequence is cleaved off during post-translational modification of the polypeptide as shown.

FIG. 4 An example of a preferred pharmaceutical composition according to the current invention. Three mutant OspA heterodimers, each comprising two mutated OspA fragments selected from different *Borrelia* OspA serotypes or a hybrid mutant OspA C-terminal fragment (S3hybD1) are present in the composition, together providing OspA antigens from six different *Borrelia* OspA serotypes. Such a pharmaceutical composition enables simultaneous immunization against six *Borrelia* serotypes.

FIG. 5 Illustration of the chemical structure of Pam$_3$Cys, an example of a fatty acid substitution of the N-terminal cysteine of full-length wild-type OspA protein as well as of lipidated mutant OspA fragment heterodimers of the invention. During post-translational modification of a full-length OspA protein or polypeptides of the invention, the N-terminal lipidation signal sequence is cleaved off and fatty acids, most commonly three palmitoyl moieties ("Pam$_3$"), are enzymatically covalently attached to the N-terminal cysteine residue (the sulfur atom, "S", is indicated by an arrow). The remaining residues of the polypeptide chain, which are located C-terminally from the Pam$_3$Cys residue, are represented by "Xn". (Modified from Bouchon, et al. (1997) Analytical Biochemistry 246: 52-61.)

Figure 6:
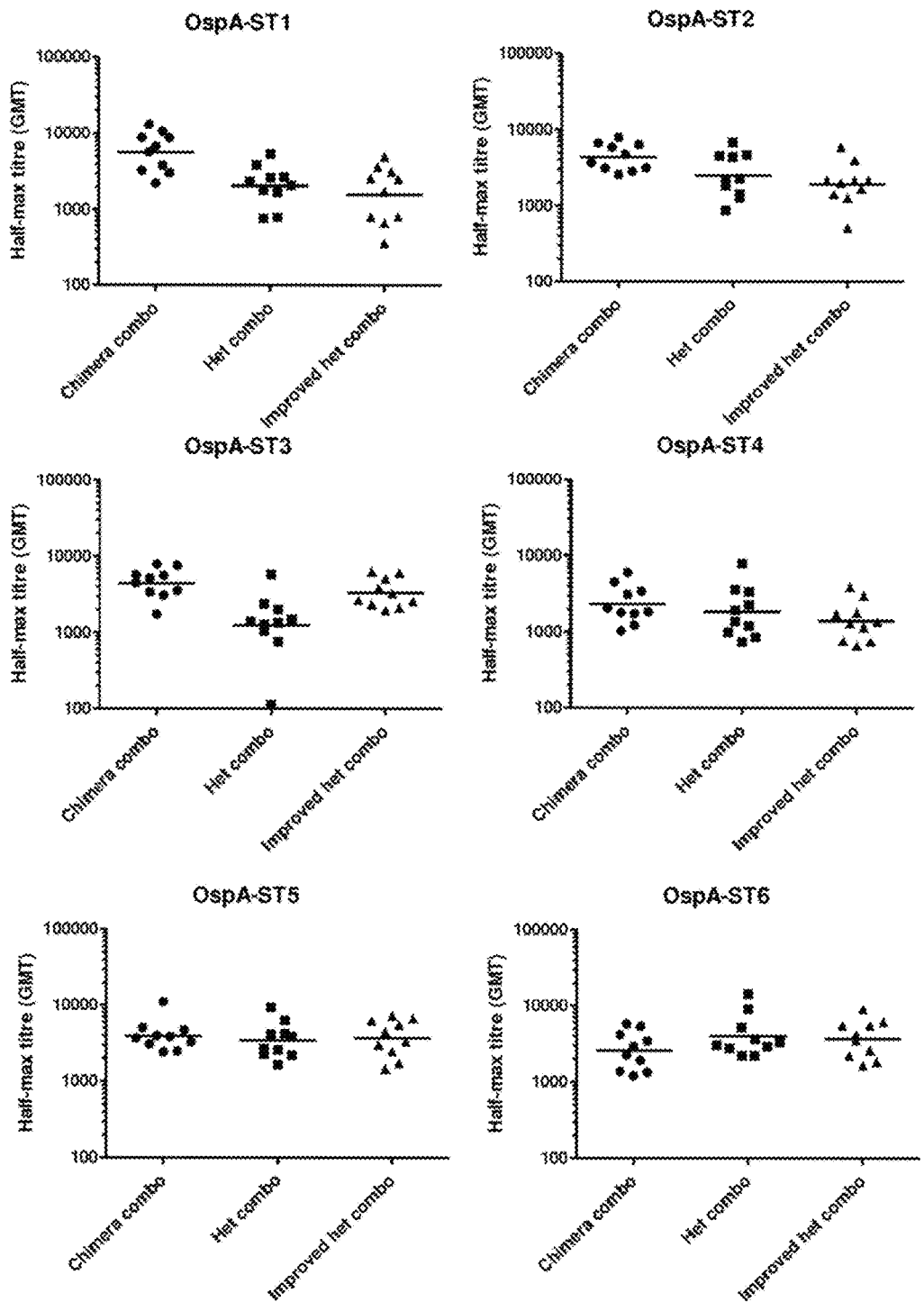
FIG. 6 shows IgG antibody titers to *Borrelia* OspA proteins of serotype 1-6 produced in mice in response to immunization with the improved heterodimer combination vaccine of the invention.

FIG. 6 Antibody titers generated to all six serotypes of full-length OspA proteins. Mice were immunized three times with 3 μg each of the indicated combination vaccines: Lip-S1D1-S2D1, Lip-S4D1-S3D1 and Lip-S5D1-S6D1 together in a 1:1:1 ratio ("Het combo"); Lip-S1D1-S2D1, Lip-S4D1-S3hybD1 and Lip-S5D1-S6D1 together in a 1:1:1 ratio ("Improved het combo") or with Lip-Chimeric OspA ST1/ST2-His, Lip-Chimeric OspA ST5/ST3-His and Lip-Chimeric OspA ST6/ST4-His together in a 1:1:1 ratio ("Chimera combo") at two week intervals and sera were collected at one week after the last dose. Titers of IgG antibodies to six different serotypes of full-length OspA proteins were determined by ELISA.

Figure 7:
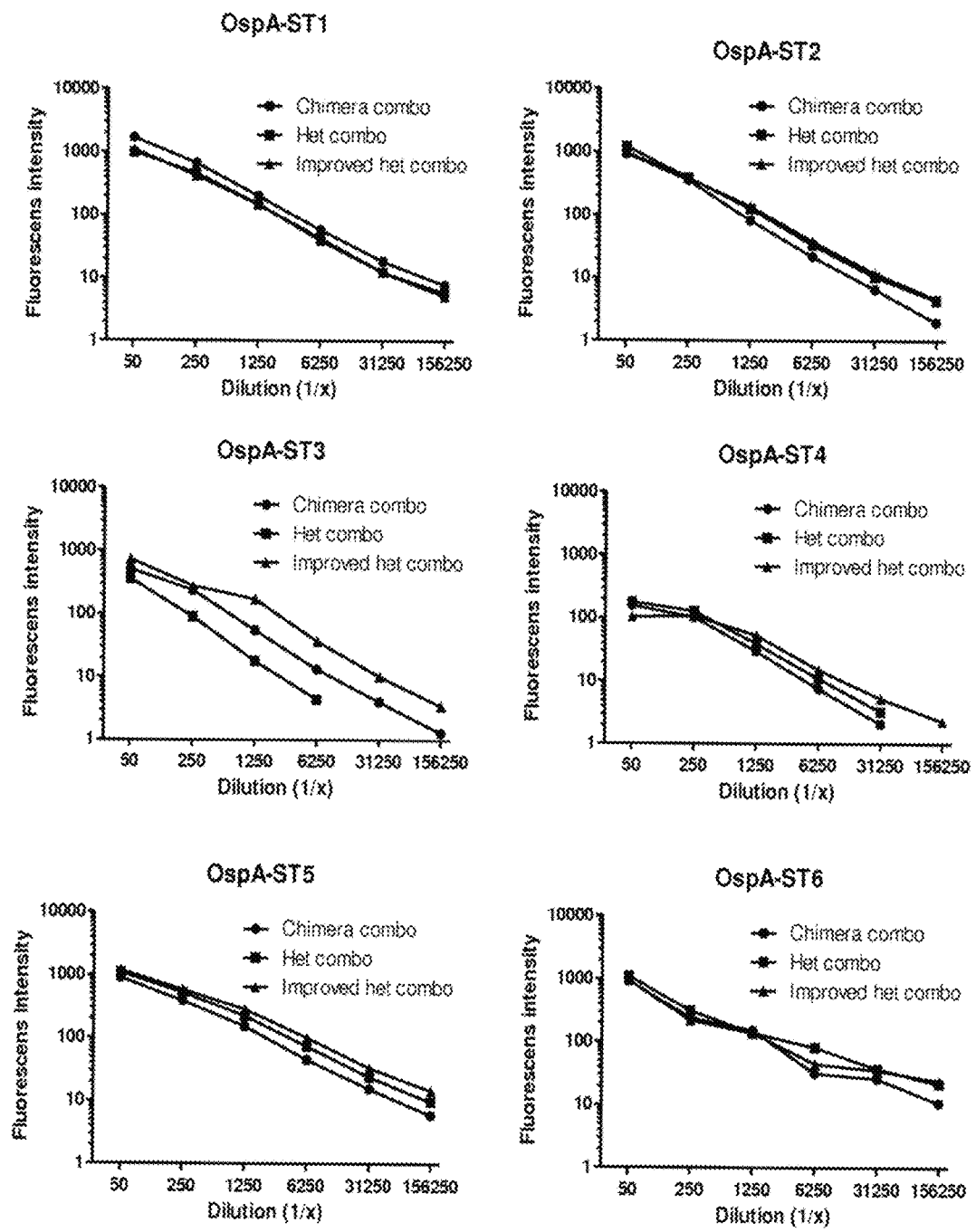
FIG. 7 shows the binding of antibodies from mice immunized with the improved heterodimer combination vaccine of the invention to the cell surface of *Borrelia* spirochetes of OspA serotypes 1-6.

FIG. 7 Binding of antibodies from immunized mice to the cell surface of Borrelia spirochetes. Mice were immunized as above and sera were collected at one week after the last dose and pooled. Serial dilutions of the sera were tested for binding to the cell surface of Borrelia spirochetes via cell staining and flow cytometry. Fluorescence intensity values observed when staining with sera collected from control mice immunized with Al(OH)$_3$ adjuvant alone were subtracted to account for non-specific binding. (Borrelia used in the binding assay were: B. burgdorferi, OspA serotype 1, strain N40; B. afzelii, OspA serotype 2, strain PKo; B. garinii, OspA serotype 3, strain Fr; B. bavariensis, OspA serotype 4, strain Fin; B. garinii, OspA serotype 5, strain PHei; B. garinii, OspA serotype 6, strain KL11.)

EXAMPLES

Example 1

Molecular Modelling of the Hybrid Serotype 3 OspA C-Terminal Fragment

Motivation to Construct Hybrid OspA ST3 C-Terminal Fragments

The Lyme borreliosis combination vaccine as described in our previous application (WO2014/006226) is composed of three mutant OspA heterodimers. Short stabilized fragments from two different OspA serotypes (ST), derived from the C-terminal domain, are fused with a short linker to form a heterodimer. The three heterodimers are composed of OspA ST1-ST2, ST4-ST3 and ST5-ST6. For improvement of the immunogenicity of the heterodimers, a signal sequence for lipidation is added in analogy with mature full-length OspA which is a lipoprotein.

The lipidated heterodimer composed of OspA ST4-ST3 (Lip-S4D1-S3D1; SEQ ID NO: 31) proved to be less soluble than the two other heterodimers, which results in low recovery during purification. This problem can mostly be attributed to the short stabilized OspA ST3 portion since this protein, as a lipidated monomer, cannot be expressed and purified.

Molecular Modelling

A comparative structural investigation of the stabilized monomers was undertaken in silico to elucidate the compatibility of the folds between the monomer models compared to the OspA crystal structure (PDB:1OSP; Li H, Dunn J J, Luft B J, Lawson C L (1997) Crystal structure of Lyme disease antigen outer surface protein A complexed with an Fab. Proc Natl Acad Sci 94: 3584-3589) and to compare their surface properties with the ST3 type monomer. The crystal structure represents serotype 1 of Borrelia burgdorferi B31, and shows OspA bound with its N-terminus, to the murine antibody Fab 184.1. Homology structure models of the six short stabilized OspA monomers were constructed starting with the ST1 OspA crystal structure and available homology models (SwissModel; Kiefer F, Arnold K, Kunzli M, Bordoli L, Schwede T (2009) The SWISS-MODEL Repository and associated resources. Nucleic Acids Res 37: D387-392), which were then modified to incorporate the stabilizing disulfide bonds and sequence changes where applicable (The PyMOL Molecular Graphics System, Version Open-Source, Schrödinger LLC).

The electrostatic potential isocontours of all six short stabilized OspA monomers were simulated with the adaptive Poisson-Boltzmann solver (APBS; Baker N A, Sept D, Joseph S, Holst M J, McCammon J A (2001) Electrostatics of nanosystems: application to microtubules and the ribosome. Proc Natl Acad Sci 98: 10037-10041, pdb2pqr; Dolinsky T J, Czodrowski P, Li H, Nielsen J E, Jensen J H, et al. (2007) PDB2PQR: expanding and upgrading automated preparation of biomolecular structures for molecular simulations. Nucleic Acids Res 35: W522-525) to determine if the short stabilized OspA ST3 protein has a pattern in surface electrostatics which deviates from the other OspA STs, which could explain the solubility problem of short stabilized OspA ST3 ("S3D1", FIG. 1). A significant polarity in the charge distribution was observed on one side of S3D1 (see arrows), which was not observed in any of the other short stabilized OspA STs.

An electrostatic potential simulation was also performed with short stabilized OspA from B. valaisiana ("BvaD1", FIG. 1). The BvaD1 OspA fragment displayed a variant polarity of the electrostatic potential isocontours on the surface, which made it a potential candidate building block for a partial segmental exchange with the aim to modify the overall surface to not show any significant extended clusters of extended electrostatic polarity as found in S3D1. The preferred link between the serotype 3 part and the exchanged part from B. valaisiana in the hybrid monomer was chosen to replace the N-terminal beta-sheet of the monomer and to leave two beta sheets and the C-terminal helix of the serotype 3 portion intact, under retention of the overall fold. The latter condition depends largely on the steric compatibility of the densely packed hydrophobic residues in the core of the molecule. Fold compatibility for the model of the hybrid stabilized monomer, S3hybD1, was verified with molecular mechanics simulation (Gromacs; Pronk S, Pall S, Schulz R, Larsson P, Bjelkmar P, et al. (2013) GROMACS 4.5: a high-throughput and highly parallel open source molecular simulation toolkit. Bioinformatics 29: 845-854).

Application in the Form of Heterodimers Containing the Hybrid OspA Fragment

As a result of the electrostatic potential simulations, a new heterodimer containing the experimental fusion of fragments OspA proteins from B. valaisiana and B. garinii (S3hybD1, FIG. 1), was cloned: Lip-S4D1-S3hybD1. In addition to the changes of the first one-third of the serotype 3 OspA fragment in the heterodimer, S4D1-S3hybD1, compared with Lip S4D1-S3D1, an amino acid substitution at position 233 (P233T, amino acid nomenclature according the immature full-length OspA; SEQ ID NO: 8) of OspA ST3 was introduced.

As illustrated in further detail below, this new heterodimer shows substantially improved solubility as well as immunogenicity against Borrelia expressing serotype 3 OspA when purified and used to immunize mice.

Example 2

Purification and Formulation of Lipidated Mutant OspA Fragment Heterodimers

Cloning and Expression of Lipidated Non-his-Tagged Mutant OspA Fragment Heterodimers The fusion OspA monomer B. valaisiana/B. garinii strain VS116/PBr was codon-optimized for E. coli expression by GeneArt (Germany) The lipidation signal sequence added to the N-terminal end was derived from the E. coli major outer membrane lipoprotein, Lpp, and was followed directly C-terminally by a CSS peptide to provide an N-terminal cysteine for lipidation. The improved heterodimer construct was generated by fusing the mutant serotype 4 OspA fragment and the hybrid serotype 3 OspA fragment via the linker sequence "LN1". Gene fragments were cloned into the pET28b(+) vector (Novagen, USA), and the stabilized heterodimers were expressed in BL21(DE3) cells (Invitrogen, USA). Cells were collected after 4 h by centrifugation and the pellet was stored at −70° C. for up to 12 months prior to further processing.

Purification of Lipidated Mutant OspA Fragment Heterodimers

Cells were disrupted mechanically by high-pressure homogenization and the lipidated mutant OspA fragment heterodimers, Lip-S4D1-S3D1 and Lip-S4D1-S3hybD1, were enriched in the lipid phase by phase separation, using Triton X-114 as detergent. Subsequently, the diluted detergent phase was subjected to anion exchange chromatography (Q-sepharose; GE Healthcare, United Kingdom) operated in non-binding mode. The resulting flow-through was loaded on a hydroxyapatite column (Bio-Rad, USA) and the lipidated proteins were eluted from the column by a linear salt gradient. The eluate was subjected to further purification over a DEAE-Sepharose column (GE Healthcare) in non-binding mode followed by gel filtration column (Superdex 200, GE Healthcare) for buffer exchange. The lipidated mutant OspA heterodimer peaks were pooled on the basis of the analytical size exclusion column and SDS-PAGE. After sterile filtration, the purified heterodimers were stored at −20° C. until formulation.

Formulation of the Combination Vaccine

Studies regarding the formulation of the combination vaccine of the invention were carried out in order to optimize stability. Different types of buffers and stabilizers were tested at various concentrations in combination with aluminium hydroxide and antigen, as described in our previous application WO2014/006226. An optimal formulation of 40 μg/mL each of three heterodimers (120 μg total protein), 10 mM sodium phosphate, 150 mM sodium chloride, 10 mM L-Methionine, 5% Sucrose, 0.05% Tween 20 (polysorbate 20) and 0.15% (w/v) aluminium hydroxide at pH 6.7±0.2 was determined.

Results

The improved heterodimer, Lip-S4D1-S3hybD1 showed an about 4-fold higher yield in terms of mg/g biomass, a significant improvement over Lip-S4D1-S3D1. Additionally, comparable purity of the improved heterodimer preparation was achievable with one less chromatography step. (See Table 1.)

TABLE 1

Improved yield of heterodimer Lip S4D1-S3hybD1 compared with Lip-S4D1-S3D1.

| Construct | Yield (mg/g biomass) | Purity (%) RP-HPLC | Purity (%) SEC-HPLC | Purity (%) SDS-PAGE | Number of Chromatography steps |
|---|---|---|---|---|---|
| Lip-S4D1-S3D1 | 0.35 | 88 | 95 | 90 | 5 |
| Lip-S4D1-S3hybD1 | 2.5 | 82 | 96 | 97 | 4 |

Example 3

Immunogenicity of Lipidated Mutant OspA Fragment Heterodimers of Different Serotypes Immunization of Mice Female C3H/HeN mice were used for all studies. Prior to immunizations, groups of ten mice were bled via the facial vein and pre-immune sera were prepared and pooled. Three s c immunizations of 100 μL each were administered at two week intervals. Each dose contained 1 μg of the respective heterodimer proteins. For the improved heterodimer combination vaccine: Lip-S1D1-S2D1 (SEQ ID NO: 29), Lip-S4D1-S3hybD1 (SEQ ID NO: 27) and Lip-S5D1-S6D1 (SEQ ID NO: 33); for the heterodimer combination vaccine of the previous invention: Lip-S1D1-S2D1 (SEQ ID NO: 29), Lip-S4D1-S3D1 (SEQ ID NO: 31) and Lip-S5D1-S6D1 (SEQ ID NO: 33) and for the chimera combination vaccine: Lip-Chimeric OspA ST1/ST2-His (Seq ID No: 40), Lip-Chimeric OspA ST5/ST3-His (Seq ID No: 41) and Lip-Chimeric OspA ST6/ST4-His (SEQ ID NO: 42). All combination vaccines were formulated with aluminium hydroxide ($Al(OH)_3$) at a final concentration of 0.15%. One week after the third immunization, blood was collected from the facial vein and immune sera prepared. In each experiment, one group immunized with PBS formulated with $Al(OH)_3$ was included as a negative control (placebo group). All animal experiments were conducted in accordance with Austrian law (BGB1 Nr. 501/1989) and approved by "Magistratsabteilung 58".

OspA ELISA

ELISA plates (Maxisorp, Nunc, Denmark) were coated with 50 ng (1 μg/mL) protein diluted in coating buffer (PBS) per well and incubated at 4° C. for 16 to 72 hours. The coating antigens were C-terminally His-tagged full length lipidated OspA ST1-6. The coating buffer was discarded and 100 μL blocking buffer (1% BSA, 0.5% Tween-20, PBS) was added and incubated at ambient temperature for 1-2 hours. Plates were washed three times with 300 μL (overflow) PBST (0.1% Tween-20, PBS). Five-fold dilutions of the sera were made in blocking buffer and 50 μL were added to each well and incubated for 1 hour at ambient temperature. Plates were washed three times with 300 μL (overflow) PBST. The secondary antibody (horseradish peroxidase [HRP]-conjugated rabbit anti-mouse IgG, DAKO, Denmark) was diluted 1:2000 in blocking buffer and 50 μL was added to each well and incubated for 1 hour at ambient temperature. Plates were washed three times with 300 μL (overflow) PBST. ABTS (2,2'-azino-bis(3-ethylbenzothiazoline-6-sulfonic acid), Sigma-Aldrich, USA) was used as substrate for HRP, 50 μL of ABTS was added to each well and incubated for 15 minutes in the dark at ambient temperature. The reaction was stopped by the addition of 50 μL 1% SDS and the absorbance was read at 405 nm A plate was regarded as valid when the absorbance of the blank was below 0.1. A sample was valid when the lowest dilution had an absorbance above 1.0 and the highest dilution was below 0.1. When these criteria were met, the half-max titer was determined. The half-max titer is the reciprocal of the dilution that corresponds to the mean absorbance between the highest and lowest dilutions.

Flow Cytometry

Spirochetes ($1\times10^6$) were mixed with an equal volume of 4% paraformaldehyde and incubated for 2 hours at room temperature in a 96-well plate (Nunclon 96U, Nunc). The plate was centrifuged for 5 minutes at 2,000 g and the supernatant was discarded. Cells were washed with 150 μL HBSS with 2% BSA (HBSS-B), centrifuged as above, and the supernatant was discarded. Mouse sera were heat inactivated by incubating them at 56° C. for 35 minutes. Heat inactivated sera were diluted in HBSS-B and sterile filtered by centrifuging at 4,000 g for 3 minutes using Costar spin-X centrifuge tube filters (0.22 µm, Corning, USA). Spirochetes were dissolved in 100 µL serum and incubated for 45 minutes at room temperature. The plate was centrifuged for 15 minutes at 2,000 g and the supernatant was discarded. The cells were washed once with 150 µL HBSS-B and then resuspended in 100 µL HBSS-B. One microliter secondary antibody (PE conjugated goat anti-mouse IgG, Beckman Coulter, USA) was added to the cells and incubated at room temperature for 45 minutes in the dark. Spirochetes were washed once with 150 µL at HBSS-B and then resuspended in 200 µL at HBSS containing 2.5 µM SYTO-17 DNA dye and incubated for 10 minutes at room temperature in the dark. The stained spirochetes were pelleted by centrifuging for 5 minutes at 2,000 g and subsequently resuspended in 200 µL HBSS. Labelled spirochetes were measured with an FC500 (Beckman Coulter) flow cytometer, gated for SYTO-17 positive events.

Results

Two different OspA heterodimer formulations ("het combo" and "improved het combo") as well as an OspA chimera combination ("chimera combo") were tested for immunogenicity in mice. Hyperimmune sera were analysed by ELISA for reactivity against full-length OspA (coating antigen) as well as for surface binding to Borrelia strains expressing different OspA serotypes (ST1 to ST6).

The ELISA results indicated that all vaccine combinations stimulated antibody responses to all six OspA serotypes (see FIG. 6). It is especially noteworthy with regard to the current invention that the improved OspA heterodimer combination vaccine resulted in higher levels of antibodies specific to serotype 3 OspA in comparison with the OspA heterodimer combination vaccine of the previous invention, whereas antibody levels to other OspA serotypes were comparably stimulated by both vaccines.

Binding of antibodies from hyperimmune mouse sera directly to borrelia spirochetes was observed in the case of Borreliae expressing all six OspA serotypes (see FIG. 7), indicating that the antibodies generated in response to all of the antigens are functionally active and can bind native OspA in situ. The fluorescence intensity was linear over a large range of serum dilutions. The fluorescence intensity observed in response to the improved heterodimer combination vaccine to spirochetes was comparable to those observed in response to the heterodimer combination vaccine and the chimera combination vaccine. Notably, with regard to binding to serotype 3 OspA borrelia, the antibodies generated by immunization with the improved vaccine were superior to antibodies generation in response to both of the other combination vaccines.

Example 4

Protective Capacity of the Improved Heterodimer Combination Vaccine Against In Vivo Borrelia Challenge Immunization of Mice Female C3H/HeN (H-2$^k$) mice were used for all studies (Janvier, France). Prior to each challenge, groups of five 8-week-old mice were bled via the tail vein and pre-immune sera were prepared and pooled. Three subcutaneous (s c) immunizations of 100 µL were administered at two week intervals at the doses indicated in Table 2. Both the improved heterodimer combination vaccine and the chimera combination vaccine included three proteins at a ratio of 1:1:1 as described in Example 3. All formulations included aluminium hydroxide (Al(OH)$_3$) at a final concentration of 0.15%. One week after the third immunization, blood was collected and hyper-immune sera were prepared. In each experiment, one group injected with Al(OH)$_3$ alone (in formulation buffer or PBS) was included as a negative control and one group of mice immunized with the wild-type full-length lipidated OspA protein from the appropriate OspA serotype served as a positive control group (B. burgdorferi strain B31 (OspA serotype 1, SEQ ID NO: 34), B. afzelii strain K78 (OspA serotype 2, SEQ ID NO: 35), B. garinii strain PHei (OspA serotype 5, SEQ ID NO: 38) or B. garinii strain DK29 (OspA serotype 6, SEQ ID NO: 39)). All animal experiments were conducted in accordance with Austrian law (BGB1 Nr. 501/1989) and approved by "Magistratsabteilung 58".

Needle Challenge of Immunized Mice with In Vitro Grown Borrelia

Two weeks after the last immunization, mice were challenged s.c. with spirochetes diluted in 100 µL growth medium (BSKII). B. burgdorferi strain ZS7 expressing OspA serotype 1 (experiments 1 and 2), B. garinii strain PHei expressing OspA serotype 5 (experiments 10 to 13) or B. garinii strain Ma expressing OspA serotype 6 (experiments 14 to 17) were used for challenge. The challenge doses were strain-dependent and dependent on the virulence of the individual strains, which was assessed by challenge experiments for determination of ID$_{50}$. Doses employed for needle challenge experiments ranged from 20 to 50 times the ID$_{50}$. Prior to each challenge, OspA expression was verified by flow cytometry (see example 3). Challenge of mice was only performed with cultures where >80% of cells were positive for OspA expression.

Challenge of Immunized Mice with Ticks Infected with B. burgdorferi or B. afzelii ("Tick Challenge")

Two weeks after the last immunization, mice were challenged with ticks harboring B. burgdorferi strain Pra4 expressing OspA serotype 1 (experiment 3), B. burgdorferi strain Pra1 expressing OspA serotype 1 (experiments 4 and 5) or B. afzelii expressing OspA serotype 2 (experimens 6 to 9). In order to facilitate tick infection of the immunized mice, the hair of the back of each mouse was removed with Veet® Cream (Reckitt Benckiser, United Kingdom) and a small ventilated container was glued to the skin with super glue (Pattex, Germany). Thereafter, two to three I. ricinus nymphs infected with B. burgdorferi strain Pra1 or Pra 4 or B. afzelii strain IS1 were applied per mouse and allowed to attach and feed until they were fully engorged and dropped off. The feeding status was monitored daily for each individual tick. Only those mice from which at least one fully- or almost fully-fed tick was collected were included in the final readout.

Sacrifice of Mice and Collection of Material

Four or six weeks after needle or tick challenge, respectively, mice were sacrificed by cervical dislocation. Blood was collected by orbital bleeding and final sera were prepared and used for VlsE ELISA and/or western blot to determine infection status. In addition, the urinary bladder from each mouse was collected and DNA was extracted and subjected to quantitative PCR (qPCR) for identification of Borrelia.

ELISA with the Invariable Region 6 (IR6) of VISE

A biotinylated 25-mer peptide (MKKDDQIAAAMVL-RGMAKDGQFALK, SEQ ID NO: 59) derived from the sequence of B. garinii strain IP90 was used for the analysis (Liang F T, Alvarez A L, Gu Y, Nowling J M, Ramamoorthy R, Philipp M T. An immunodominant conserved region within the variable domain of VlsE, the variable surface antigen of Borrelia burgdorferi. J Immunol 1999; 163:5566-73). Streptavidin pre-coated 96-well ELISA plates (Nunc), were coated with 100 µL/well (1 µg/mL) peptide in PBS supplemented with 0.1% Tween (PBS/0.1T). The plates were incubated overnight at 4° C. After coating with the peptide, the plates were washed once with PBS/0.1T. The plates were then blocked for one hour at room temperature (RT) with 100 µL/well of PBS+2% BSA, before being washed again with PBS/0.1T. Reactivity of post-challenge sera (final sera) to the peptide was tested at 1:200 and 1:400 dilutions in PBS+1% BSA. Plates were incubated for 90 minutes at RT before being washed three times with PBS/0.1T. Each well then received 50 µL of 1.3 µg/mL polyclonal rabbit anti-mouse IgG conjugated to HRP (Dako) in PBS+1% BSA. The plates were then incubated for 1 hour at RT. After three washes with PBS/0.1T, ABTS (50 µL/well) was added as substrate (Sigma-Aldrich) and color was allowed to develop for 30 minutes. Absorbance was measured at 405 nm. All sera were tested in duplicate. Negative controls included PBS instead of sera as well as plates not coated with the peptide. Sera from mice shown to be culture positive for borrelia infection were used as positive controls.

DNA Extraction and Purification

The urinary bladder from each mouse was subjected to DNA extraction and purification using the DNeasy Blood and Tissue Kit (Qiagen) according to the manufacturer's instructions with the following modification. Each urinary bladder was digested overnight at 60° C. using 100 µL recombinant Proteinase K (PCR grade; 14-22 mg/mL, Roche). The DNA was eluted in 50 µL sterile deionized water and stored at −20° C. As a negative control, every tenth sample was followed by one empty purification column in each DNA extraction and purification.

qPCR Targeting recA

Oligonucleotide primers were designed for the recA gene in a manner that they could be used in qPCR for identification of all relevant Borrelia species causing Lyme borreliosis (forward: CATGCTCTTGATCCTGTTTA, SEQ ID NO: 57, reverse: CCCATTTCTCCATCTATCTC, SEQ ID NO: 58). The recA fragment was cloned from the B. burgdorferi s.s. strain N40 into pET28b(+), to be used as standard in each reaction. The chromosomal DNA extracted from mouse urinary bladders was diluted 1:4 in water in order to reduce matrix effects observed with undiluted DNA. A master mix consisting of 10 µL SSoAdvanced™ SYBR® Green Supermix, 0.3 µL of each primer (10 µM), and 7.4 µL water was prepared for each experiment. Eighteen µL of master mix was mixed with 2 µL of the diluted DNA extracted from urinary bladder in micro-titer plates and the DNA was amplified using a CFX96 real-time PCR detection system (Bio-Rad). The DNA was denatured for 3 minutes at 95° C., followed by 50 cycles of 15 seconds at 95° C. and 30 seconds at 55° C. After amplification, the DNA was prepared for melting curve analysis by denaturation for 30 seconds at 95° C. followed by 2 minutes at 55° C. The melting curve analysis was performed by 5 seconds incubation at 55° C., with a 0.5° C. increase per cycle, and 5 seconds at 95° C. On each plate, four no-template controls (NTC) were included as well as a standard curve in duplicate with template copy numbers ranging from 10 to 10,000.

Western Blot

Binding of final sera to whole cell lysates from borrelia belonging to the corresponding OspA serotype was analyzed by western blot. Briefly, 2.5 µg of spirochete lysate per mouse sera to be analyzed was separated by SDS-PAGE under reducing conditions using 4-12% Tris-Glycine ZOOM gels (Invitrogen). Separated proteins were transferred onto a nitrocellulose membrane using the iBlot® Dry blotting system (Invitrogen). After blocking in 5% milk for 1 hour, final sera were added at a 1:2000 dilution and incubated at +4° C. overnight. The membranes were then washed three times with PBS/0.1T followed by a one hour incubation in polyclonal rabbit anti mouse IgG conjugated to HRP (Dako) diluted 1:10,000. The immunoblots were visualized with Amersham ECL Plus™ Western blotting detection reagents (GE Healthcare) and Kodak BioMax films (Kodak).

Infection Readout

The final infection readout was based on two separate methods: detecting the presence of Borrelia-specific antibodies (western blot and VlsE ELISA) and presence of Borrelia DNA (qPCR targeting recA). In experiments where B. burgdorferi strain ZS7 was used for challenge (experiments 1 and 2), western blot together with qPCR were applied. In all other experiments, VlsE ELISA and qPCR were used. There was a high consistency between the two methods (>95%); therefore a mouse was regarded as infected when at least one of the two methods was positive. Statistical significance was determined by Fisher's exact test (two-tailed).

Results

The improved heterodimer combination vaccine was tested for protective capacity against Borrelia challenge. The results of these experiments are summarized in Table 2. Immunized mice were challenged with B. burgdorferi s.s. (OspA serotype 1, strain ZS7, needle challenge, Experiments 1 and 2 or strains Pra1 or Pra 4, tick challenge, Experiments 3 or 4 and 5, respectively), B. afzelii (OspA serotype 2, strain IS1, tick challenge, Experiments 6-9), B. garinii (OspA serotype 5, strain PHei, needle challenge, Experiments 10-13) or B. garinii (OspA serotype 6, strain Ma, needle challenge, Experiments 14-17). In some experiments, other OspA-based antigens, such as the chimera combination vaccine or a lipidated full-length OspA protein, were included. A group of mice immunized with PBS or formulation buffer combined with Al(OH)$_3$ served as a placebo (adjuvant alone) control group in each experiment.

The protection data from the 17 experiments are summarized in Table 2. In all experiments, a high level of infection was seen in all placebo groups. Additionally, a low infection rate was observed in the groups receiving the corresponding full length OspA protein, with the exception of the full-length OspA serotype 6, wherein only partial protection was observed (experiments 14 to 17). These results validate the experimental set-up and readout methods.

The improved heterodimer combination vaccine conferred significant protection (p-values <0.05), at a 3 µg dose, when mice were challenged with in vitro grown B. burgdorferi s.s. or B. garinii (OspA serotype 5 or 6), or ticks harboring B. burgdorferi or B. afzelii. Furthermore, when different immunization doses were assessed for vaccine efficacy, highly significant protection (p-values <0.01) could be shown when 0.03 µg of the improved heterodimer combination vaccine was administered and the mice were challenged with B. afzelii or B. garinii (OspA serotype 5 or 6) (Experiment 8, 9, 12, 13 and 16). In summary, the improved heterodimer combination vaccine induced protective immunity against three Borrelia species (B. burgdorferi, B. afzelii and B. garinii) including four clinically relevant OspA serotypes (1, 2, 5 and 6), as shown in mouse models using either in vitro grown spirochetes or infected ticks for challenge.

Protection against serotypes 5 and 6 comparable to that conferred by the improved heterodimer combination vaccine was also observed in mice immunized with the chimera combination vaccine (data not shown).

TABLE 2

Protective capacity of the improved mutant OspA heterodimer combination vaccine of the invention against OspA serotype 1, serotype 2, serotype 5 and serotype 6 *Borrelia* challenge. Groups of mice were immunized three times with the indicated doses of immunogen or Al(OH)$_3$ adjuvant alone at two-week intervals. Immunogens used were a 1:1:1 combination of the mutant OspA heterodimers Lip-S1D1-S2D1, Lip-S4D1-S3hybD1 and Lip-S5D1-S6D1 ("Improved heterodimer combination vaccine"), a 1:1:1 combination of Lip-Chimeric OspA ST1/ST2-His, Lip-Chimeric OspA ST5/ST3-His and Lip-Chimeric OspA ST6/ST4-His ("Chimera combination vaccine") and Lip-OspA1-His (lipidated full-length OspA protein from *B. burgdorferi* strain B31) or Lip-OspA2-His (lipidated full-length OspA protein from *B. afzelii* strain K78), Lip-OspA5-His (lipidated full-length OspA protein from *B. garinii* strain PHei) or Lip-OspA6-His (lipidated full-length OspA protein from *B. garinii* strain DK29). Immunized mice were challenged s.c. two weeks after the last immunization with the indicated *borrelia* species using a syringe (*B. burgdorferi* strain ZS7, *B. garinii* strain PHei or *B. garinii* strain Ma) or using ticks (*B. burgdorferi* strain Pra1 or Pra4 or *B. afzelii* strain IS1).

A Protection against needle challenge with serotype 1 OspA *borrelia* by chimera combination vaccine and improved heterodimer combination vaccine (one dose: 3 µg)

| Immunogen | Dose | Challenge | Experiment 1: Infected/Total (p-value) | Experiment 2: Infected/Total (p-value) |
|---|---|---|---|---|
| Lip-OspA1-His (SEQ ID NO: 34) | 3 × 1.0 µg | *B. burgdorferi* (OspA serotype 1) strain ZS7 | 0/10 (<0.0001) | 1/10 (<0.0001) |
| Chimera combination vaccine: | | *B. burgdorferi* (OspA serotype 1) strain ZS7 | 0/10 (<0.0001) | 0/10 (<0.0001) |
| Lip-Chimeric OspA ST1/ST2-His (Seq ID No: 40) | 3 × 1.0 µg | | | |
| Lip-Chimeric OspA ST5/ST3-His (Seq ID No: 41) | 3 × 1.0 µg | | | |
| Lip-Chimeric OspA ST6/ST4-His (Seq ID No: 42) | 3 × 1.0 µg | | | |
| Improved heterodimer combination vaccine: | | *B. burgdorferi* (OspA serotype 1) strain ZS7 | 0/10 (<0.0001) | 0/10 (<0.0001) |
| Lip-S1D1-S2D1 (Seq ID No: 29) | 3 × 1.0 µg | | | |
| Lip-S4D1-S3hybD1 (Seq ID No: 27) | 3 × 1.0 µg | | | |
| Lip-S5D1-S6D1 (Seq ID No: 33) | 3 × 1.0 µg | | | |
| Al(OH)$_3$ adjuvant alone | — | *B. burgdorferi* (OspA serotype 1) strain ZS7 | 9/9 | 10/10 |

B Protection against tick challenge with serotype 1 OspA *borrelia* by chimera combination vaccine and improved heterodimer combination vaccine (one dose: 3 µg)

| Immunogen | Dose | Challenge | Experiment 3: Infected/Total (p-value) | Experiment 4: Infected/Total (p-value) |
|---|---|---|---|---|
| Lip-OspA1-His (SEQ ID NO: 34) | 3 × 1.0 µg | Tick challenge with *B. burgdorferi* (OspA serotype 1) strain Pra4 (Exp. 3) or Pra1 (Exp. 4) | 0/4 (0.0475) | 1/9 (0.0216) |
| Chimera combination vaccine: | | Tick challenge with *B. burgdorferi* (OspA serotype 1) strain Pra4 (Exp. 3) or Pra1 (Exp. 4) | 0/8 (0.0060) | 0/7 (0.0093) |
| Lip-Chimeric OspA ST1/ST2-His (Seq ID No: 40) | 3 × 1.0 µg | | | |
| Lip-Chimeric OspA ST5/ST3-His (Seq ID No: 41) | 3 × 1.0 µg | | | |
| Lip-Chimeric OspA ST6/ST4-His (Seq ID No: 42) | 3 × 1.0 µg | | | |
| Improved heterodimer combination vaccine: | | Tick challenge with *B. burgdorferi* (OspA serotype 1) strain Pra4 (Exp. 3) or Pra1 (Exp. 4) | 0/5 (0.0260) | 0/7 (0.0093) |
| Lip-S1D1-S2D1 (Seq ID No: 29) | 3 × 1.0 µg | | | |
| Lip-S4D1-S3hybD1 (Seq ID No: 27) | 3 × 1.0 µg | | | |
| Lip-S5D1-S6D1 (Seq ID No: 33) | 3 × 1.0 µg | | | |
| Al(OH)$_3$ adjuvant alone | — | Tick challenge with *B. burgdorferi* (OspA serotype 1) strain Pra4 (Exp. 3) or Pra1 (Exp. 4) | 5/6 | 5/6 |

C Protection against tick challenge with serotype 1 OspA *borrelia* by improved heterodimer combination vaccine (decreasing doses: 3 µg and 0.3 µg)

| Immunogen | Dose | Challenge | Experiment 5: Infected/Total (p-value) |
|---|---|---|---|
| Improved heterodimer combination vaccine: | | Tick challenge with *B. burgdorferi* (OspA serotype 1) | 1/7 (0.0174) |
| Lip-S1D1-S2D1 (Seq ID No: 29) | 3 × 1.0 µg | | |

TABLE 2-continued

Protective capacity of the improved mutant OspA heterodimer combination vaccine of the invention against OspA serotype 1, serotype 2, serotype 5 and serotype 6 *Borrelia* challenge. Groups of mice were immunized three times with the indicated doses of immunogen or Al(OH)$_3$ adjuvant alone at two-week intervals. Immunogens used were a 1:1:1 combination of the mutant OspA heterodimers Lip-S1D1-S2D1, Lip-S4D1-S3hybD1 and Lip-S5D1-S6D1 ("Improved heterodimer combination vaccine"), a 1:1:1 combination of Lip-Chimeric OspA ST1/ST2-His, Lip-Chimeric OspA ST5/ST3-His and Lip-Chimeric OspA ST6/ST4-His ("Chimera combination vaccine") and Lip-OspA1-His (lipidated full-length OspA protein from *B. burgdorferi* strain B31) or Lip-OspA2-His (lipidated full-length OspA protein from *B. afzelii* strain K78), Lip-OspA5-His (lipidated full-length OspA protein from *B. garinii* strain PHei) or Lip-OspA6-His (lipidated full-length OspA protein from *B. garinii* strain DK29). Immunized mice were challenged s.c. two weeks after the last immunization with the indicated *borrelia* species using a syringe (*B. burgdorferi* strain ZS7, *B. garinii* strain PHei or *B. garinii* strain Ma) or using ticks (*B. burgdorferi* strain Pra1 or Pra4 or *B. afzelii* strain IS1).

| Immunogen | Dose | Challenge | Infected/Total (p-value) |
|---|---|---|---|
| Lip-S4D1-S3hybD1 (Seq ID No: 27) | 3 × 1.0 μg | strain Pra1 | |
| Lip-S5D1-S6D1 (Seq ID No: 33) | 3 × 1.0 μg | | |
| Improved heterodimer combination vaccine: | | Tick challenge with *B. burgdorferi* | 1/9 (0.0059) |
| Lip-S1D1-S2D1 (Seq ID No: 29) | 3 × 0.1 μg | (OspA serotype 1) | |
| Lip-S4D1-S3hybD1 (Seq ID No: 27) | 3 × 0.1 μg | strain Pra1 | |
| Lip-S5D1-S6D1 (Seq ID No: 33) | 3 × 0.1 μg | | |
| Al(OH)$_3$ adjuvant alone | — | Tick challenge with *B. burgdorferi* (OspA serotype 1) strain Pra1 | 7/8 |

D Protection against tick challenge with serotype 2 OspA *borrelia* by chimera combination vaccine and improved heterodimer combination vaccine (one dose: 3 μg)

| Immunogen | Dose | Challenge | Experiment 6: Infected/Total (p-value) | Experiment 7: Infected/Total (p-value) |
|---|---|---|---|---|
| Lip-OspA2-His (SEQ ID NO: 35) | 3 × 1.0 μg | Tick challenge with *B. afzelii* (OspA serotype 2) strain IS1 | 0/8 (0.0016) | 0/9 (0.0002) |
| Chimera combination vaccine: | | Tick challenge with *B. afzelii* (OspA serotype 2) strain IS1 | 0/7 (0.0025) | 0/9 (0.0002) |
| Lip-Chimeric OspA ST1/ST2-His (Seq ID No: 40) | 3 × 1.0 μg | | | |
| Lip-Chimeric OspA ST5/ST3-His (Seq ID No: 41) | 3 × 1.0 μg | | | |
| Lip-Chimeric OspA ST6/ST4-His (Seq ID No: 42) | 3 × 1.0 μg | | | |
| Improved heterodimer combination vaccine: | | Tick challenge with *B. afzelii* (OspA serotype 2) strain IS1 | 0/9 (0.0010) | 0/7 (0.0003) |
| Lip-S1D1-S2D1 (Seq ID No: 29) | 3 × 1.0 μg | | | |
| Lip-S4D1-S3hybD1 (Seq ID No: 27) | 3 × 1.0 μg | | | |
| Lip-S5D1-S6D1 (Seq ID No: 33) | 3 × 1.0 μg | | | |
| Al(OH)$_3$ adjuvant alone | — | Tick challenge with *B. afzelii* (OspA serotype 2) strain IS1 | 5/5 | 8/8 |

E Protection against tick challenge with serotype 2 OspA *borrelia* by improved heterodimer combination vaccine (decreasing doses: 0.03 μg and 0.003 μg)

| Immunogen | Dose | Challenge | Experiment 8: Infected/Total (p-value) | Experiment 9: Infected/Total (p-value) |
|---|---|---|---|---|
| Improved heterodimer combination vaccine: | | Tick challenge with *B. afzelii* (OspA serotype 2) strain IS1 | 0/9 (0.0004) | 2/7 (0.0096) |
| Lip-S1D1-S2D1 (Seq ID No: 29) | 3 × 0.01 μg | | | |
| Lip-S4D1-S3hybD1 (Seq ID No: 27) | 3 × 0.01 μg | | | |
| Lip-S5D1-S6D1 (Seq ID No: 33) | 3 × 0.01 μg | | | |
| Improved heterodimer combination vaccine: | | Tick challenge with *B. afzelii* (OspA serotype 2) strain IS1 | 7/10 (n.s.) | 1/8 (0.0008) |
| Lip-S1D1-S2D1 (Seq ID No: 29) | 3 × 0.001 μg | | | |
| Lip-S4D1-S3hybD1 (Seq ID No: 27) | 3 × 0.001 μg | | | |
| Lip-S5D1-S6D1 (Seq ID No: 33) | 3 × 0.001 μg | | | |
| Al(OH)$_3$ adjuvant alone | — | Tick challenge with *B. afzelii* (OspA serotype 2) strain IS1 | 6/6 | 9/9 |

TABLE 2-continued

Protective capacity of the improved mutant OspA heterodimer combination vaccine of the invention against OspA serotype 1, serotype 2, serotype 5 and serotype 6 *Borrelia* challenge. Groups of mice were immunized three times with the indicated doses of immunogen or Al(OH)$_3$ adjuvant alone at two-week intervals. Immunogens used were a 1:1:1 combination of the mutant OspA heterodimers Lip-S1D1-S2D1, Lip-S4D1-S3hybD1 and Lip-S5D1-S6D1 ("Improved heterodimer combination vaccine"), a 1:1:1 combination of Lip-Chimeric OspA ST1/ST2-His, Lip-Chimeric OspA ST5/ST3-His and Lip-Chimeric OspA ST6/ST4-His ("Chimera combination vaccine") and Lip-OspA1-His (lipidated full-length OspA protein from *B. burgdorferi* strain B31) or Lip-OspA2-His (lipidated full-length OspA protein from *B. afzelii* strain K78), Lip-OspA5-His (lipidated full-length OspA protein from *B. garinii* strain PHei) or Lip-OspA6-His (lipidated full-length OspA protein from *B. garinii* strain DK29). Immunized mice were challenged s.c. two weeks after the last immunization with the indicated *borrelia* species using a syringe (*B. burgdorferi* strain ZS7, *B. garinii* strain PHei or *B. garinii* strain Ma) or using ticks (*B. burgdorferi* strain Pra1 or Pra4 or *B. afzelii* strain IS1).

F Protection against needle challenge with serotype 5 OspA *borrelia* by improved heterodimer combination vaccine (one dose: 3 µg)

| Immunogen | Dose | Challenge | Experiment 10: Infected/Total (p-value) | Experiment 11: Infected/Total (p-value) |
|---|---|---|---|---|
| Lip-OspA5-His (SEQ ID NO: 38) | 3 × 1.0 µg | *B. garinii* (OspA serotype 5) strain PHei) | 0/10 (<0.0001) | 0/10 (<0.0001) |
| Improved heterodimer combination vaccine: Lip-S1D1-S2D1 (Seq ID No: 29) Lip-S4D1-S3hybD1 (Seq ID No: 27) Lip-S5D1-S6D1 (Seq ID No: 33) | 3 × 1.0 µg 3 × 1.0 µg 3 × 1.0 µg | *B. garinii* (OspA serotype 5) strain PHei) | 0/10 (<0.0001) | 1/10 (<0.0001) |
| Al(OH)$_3$ adjuvant alone | — | *B. garinii* (OspA serotype 5) strain PHei) | 10/10 | 10/10 |

G Protection against needle challenge with serotype 5 OspA *borrelia* by improved heterodimer combination vaccine (decreasing doses: 3 µg, 0.3 µg and 0.03 µg)

| Immunogen | Dose | Challenge | Experiment 12: Infected/Total (p-value) | Experiment 13: Infected/Total (p-value) |
|---|---|---|---|---|
| Lip-OspA5-His (SEQ ID NO: 38) | 3 × 1.0 µg | *B. garinii* (OspA serotype 5) strain PHei) | 0/10 (0.0007) | 0/10 (<0.001) |
| Improved heterodimer combination vaccine: Lip-S1D1-S2D1 (Seq ID No: 29) Lip-S4D1-S3hybD1 (Seq ID No: 27) Lip-S5D1-S6D1 (Seq ID No: 33) | 3 × 1.0 µg 3 × 1.0 µg 3 × 1.0 µg | *B. garinii* (OspA serotype 5) strain PHei) | 0/10 (<0.0007) | 1/10 (0.0002) |
| Improved heterodimer combination vaccine: Lip-S1D1-S2D1 (Seq ID No: 29) Lip-S4D1-S3hybD1 (Seq ID No: 27) Lip-S5D1-S6D1 (Seq ID No: 33) | 3 × 0.1 µg 3 × 0.1 µg 3 × 0.1 µg | *B. garinii* (OspA serotype 5) strain PHei) | 0/10 (<0.0007) | 0/10 (<0.0001) |
| Improved heterodimer combination vaccine: Lip-S1D1-S2D1 (Seq ID No: 29) Lip-S4D1-S3hybD1 (Seq ID No: 27) Lip-S5D1-S6D1 (Seq ID No: 33) | 3 × 0.01 µg 3 × 0.01 µg 3 × 0.01 µg | *B. garinii* (OspA serotype 5) strain PHei) | 2/10 (<0.0219) | 3/10 (0.0047) |
| Al(OH)$_3$ adjuvant alone | — | *B. garinii* (OspA serotype 5) strain PHei) | 8/10 | 9/9 |

H Protection against needle challenge with serotype 6 OspA *borrelia* by improved heterodimer combination vaccine (one dose: 3 µg)

| Immunogen | Dose | Challenge | Experiment 14: Infected/Total (p-value) | Experiment 15: Infected/Total (p-value) |
|---|---|---|---|---|
| Lip-OspA6-His (SEQ ID NO: 39) | 3 × 1.0 µg | *B. garinii* (OspA serotype 6) strain Ma) | 4/10 (0.0108) | 6/10 (n.s.) |
| Improved heterodimer combination vaccine: Lip-S1D1-S2D1 (Seq ID No: 29) Lip-S4D1-S3hybD1 (Seq ID No: 27) Lip-S5D1-S6D1 (Seq ID No: 33) | 3 × 1.0 µg 3 × 1.0 µg 3 × 1.0 µg | *B. garinii* (OspA serotype 6) strain Ma) | 0/10 (<0.0001) | 0/10 (0.0007) |
| Al(OH)$_3$ adjuvant alone | — | *B. garinii* (OspA serotype 6) strain Ma) | 10/10 | 8/10 |

TABLE 2-continued

Protective capacity of the improved mutant OspA heterodimer combination vaccine of the invention against OspA serotype 1, serotype 2, serotype 5 and serotype 6 *Borrelia* challenge. Groups of mice were immunized three times with the indicated doses of immunogen or Al(OH)$_3$ adjuvant alone at two-week intervals. Immunogens used were a 1:1:1 combination of the mutant OspA heterodimers Lip-S1D1-S2D1, Lip-S4D1-S3hybD1 and Lip-S5D1-S6D1 ("Improved heterodimer combination vaccine"), a 1:1:1 combination of Lip-Chimeric OspA ST1/ST2-His, Lip-Chimeric OspA ST5/ST3-His and Lip-Chimeric OspA ST6/ST4-His ("Chimera combination vaccine") and Lip-OspA1-His (lipidated full-length OspA protein from *B. burgdorferi* strain B31) or Lip-OspA2-His (lipidated full-length OspA protein from *B. afzelii* strain K78), Lip-OspA5-His (lipidated full-length OspA protein from *B. garinii* strain PHei) or Lip-OspA6-His (lipidated full-length OspA protein from *B. garinii* strain DK29). Immunized mice were challenged s.c. two weeks after the last immunization with the indicated *borrelia* species using a syringe (*B. burgdorferi* strain ZS7, *B. garinii* strain PHei or *B. garinii* strain Ma) or using ticks (*B. burgdorferi* strain Pra1 or Pra4 or *B. afzelii* strain IS1).

I Protection against needle challenge with serotype 6 OspA *borrelia* by improved heterodimer combination vaccine (decreasing doses: 3 µg, 0.3 µg and 0.03 µg)

| Immunogen | Dose | Challenge | Experiment 16: Infected/Total (p-value) | Experiment 17: Infected/Total (p-value) |
|---|---|---|---|---|
| Lip-OspA6-His (SEQ ID NO: 39) | 3 × 1.0 µg | *B. garinii* (OspA serotype 6) strain Ma) | 4/10 (0.0108) | 8/10 (n.s.) |
| Improved heterodimer combination vaccine: Lip-S1D1-S2D1 (Seq ID No: 29) Lip-S4D1-S3hybD1 (Seq ID No: 27) Lip-S5D1-S6D1 (Seq ID No: 33) | 3 × 1.0 µg 3 × 1.0 µg 3 × 1.0 µg | *B. garinii* (OspA serotype 6) strain Ma) | 0/10 (<0.0001) | 0/10 (0.0001) |
| Improved heterodimer combination vaccine: Lip-S1D1-S2D1 (Seq ID No: 29) Lip-S4D1-S3hybD1 (Seq ID No: 27) Lip-S5D1-S6D1 (Seq ID No: 33) | 3 × 0.1 µg 3 × 0.1 µg 3 × 0.1 µg | *B. garinii* (OspA serotype 6) strain Ma) | 2/10 (0.0007) | 2/10 (0.0054) |
| Improved heterodimer combination vaccine: Lip-S1D1-S2D1 (Seq ID No: 29) Lip-S4D1-S3hybD1 (Seq ID No: 27) Lip-S5D1-S6D1 (Seq ID No: 33) | 3 × 0.01 µg 3 × 0.01 µg 3 × 0.01 µg | *B. garinii* (OspA serotype 6) strain Ma) | 3/10 (0.0031) | 4/10 (n.s.) |
| Al(OH)$_3$ adjuvant alone | — | *B. garinii* (OspA serotype 6) strain Ma) | 10/10 | 9/10 |

P-value; Fisher's exact test, two-tailed, as compared to the adjuvant alone group, are indicated in parenthesis. not significant (n.s.).

```
SEQUENCES
                                                              SEQ ID NO: 1
S3hybD1: hybrid OspA C-terminal fragment; amino acids
of positions 125-176 from Borrelia valaisiana, strain
VS116, and amino acids 177-274 from Borrelia garinii,
strain PBr, with disulfide bond type 1 and T in
position 233
FNEKGEVSEKILTRSNGTTLEYSQMTDAENATKAVETLKNGIKLPGNLVGGKTKLTVTCGTV

TLSKNISKSGEITVALNDTETTPADKKTGEWKSDTSTLTISKNSQKTKQLVFTKENTITVQNYN

RAGNALEGSPAEIKDLAELCAALK

SEQ ID NO: 2
B. valaisiana (strain VS116), OspA aa 125-176
FNEKGEVSEKILTRSNGTTLEYSQMTDAENATKAVETLKNGIKLPGNLVGGK SEQ ID NO: 3
B. garinii (strain PBr, serotype 3), OspA aa 177-274,
with T in position 233, from full-length OspA (SEQ ID NO: 8)
TKLTVTCGTVTLSKNISKSGEITVALNDTETTPADKKTGEWKSDTSTLTISKNSQKTKQLVFTK

ENTITVQNYNRAGNALEGSPAEIKDLAELCAALK

SEQ ID NO: 4
B. valaisiana (strain VS116), OspA
MKKYLLGIGLILALIACKQNVSSLDEKNSASVDLPGEMKVLVSKEKDKDGKYSLVATVDKVE

LKGTSDKNNGSGTLEGVKDDKSKVKLTISDDLGETKLETFKEDGTLVSRKVNFKDKSFTEEK

FNEKGEVSEKILTRSNGTTLEYSQMTDAENATKAVETLKNGIKLPGNLVGGKTTLKITEGTVT
```

LSKHIAKSGEVTVEINDTSSTPNTKKTGKWDARNSTLTIIVDSKNKTKLVFTKQDTITVQSYNP

AGNKLEGTAVEIKTLQELKNALK

SEQ ID NO: 5
B. burgdorferi s.s. (strain B31, OspA serotype 1)
MKKYLLGIGLILALIACKQNVSSLDEKNSVSVDLPGEMKVLVSKEKNKDGKYDLIATVDKLE

LKGTSDKNNGSGVLEGVKADKSKVKLTISDDLGQTTLEVFKEDGKTLVSKKVTSKDKSSTEE

KFNEKGEVSEKIITRADGTRLEYTGIKSDGSGKAKEVLKGYVLEGTLTAEKTTLVVKEGTVTL

SKNISKSGEVSVELNDTDSSAATKKTAAWNSGTSTLTITVNSKKTKDLVFTKENTITVQQYDS

NGTKLEGSAVEITKLDEIKNALK

SEQ ID NO: 6
B. afzelii (strain K78; OspA serotype 2)
MKKYLLGIGLILALIACKQNVSSLDEKNSASVDLPGEMKVLVSKEKDKDGKYSLKATVDKIE

LKGTSDKDNGSGVLEGTKDDKSKAKLTIADDLSKTTFELFKEDGKTLVSRKVSSKDKTSTDE

MFNEKGELSAKTMTRENGTKLEYTEMKSDGTGKAKEVLKNFTLEGKVANDKVTLEVKEGT

VTLSKEIAKSGEVTVALNDTNTTQATKKTGAWDSKTSTLTISVNSKKTTQLVFTKQDTITVQK

YDSAGTNLEGTAVEIKTLDELKNALK

SEQ ID NO: 7
B. garinii (strain PBr, OspA serotype 3) with P in
position 233 (embl accession X80256.1)
MKKYLLGIGLILALIACKQNVSSLDEKNSVSVDLPGGMKVLVSKEKDKDGKYSLMATVEKLE

LKGTSDKSNGSGVLEGEKADKSKAKLTISQDLNQTTFEIFKEDGKTLVSRKVNSKDKSSTEEK

FNDKGKLSEKVVTRANGTRLEYTEIKNDGSGKAKEVLKGFALEGTLTDGGETKLTVTEGTVT

LSKNISKSGEITVALNDTETTPADKKTGEWKSDTSTLTISKNSQKPKQLVFTKENTITVQNYNR

AGNALEGSPAEIKDLAELKAALK

SEQ ID NO: 8
B. garinii (strain PBr, OspA serotype 3) with T in
position 233 (embl accession ACL34827.1)
MKKYLLGIGLILALIACKQNVSSLDEKNSVSVDLPGGMKVLVSKEKDKDGKYSLMATVEKLE

LKGTSDKSNGSGVLEGEKADKSKAKLTISQDLNQTTFEIFKEDGKTLVSRKVNSKDKSSTEEK

FNDKGKLSEKVVTRANGTRLEYTEIKNDGSGKAKEVLKGFALEGTLTDGGETKLTVTEGTVT

LSKNISKSGEITVALNDTETTPADKKTGEWKSDTSTLTISKNSQKTKQLVFTKENTITVQNYNR

AGNALEGSPAEIKDLAELKAALK

SEQ ID NO: 9
B. bavariensis (strain PBi, OspA serotype 4)
MKKYLLGIGLILALIACKQNVSSLDEKNSVSVDLPGEMKVLVSKEKDKDGKYSLMATVDKLE

LKGTSDKSNGSGTLEGEKSDKSKAKLTISEDLSKTTFEIFKEDGKTLVSKKVNSKDKSSIEEKF

NAKGELSEKTILRANGTRLEYTEIKSDGTGKAKEVLKDFALEGTLAADKTTLKVTEGTVVLS

KHIPNSGEITVELNDSNSTQATKKTGKWDSNTSTLTISVNSKKTKNIVFTKEDTITVQKYDSAG

TNLEGNAVEIKTLDELKNALK

SEQ ID NO: 10
B. garinii (strain PHei, OspA serotype 5)
MKKYLLGIGLILALIACKQNVSSLDEKNSVSVDLPGGMKVLVSKEKDKDGKYSLMATVEKLE

LKGTSDKNNGSGTLEGEKTDKSKVKLTIAEDLSKTTFEIFKEDGKTLVSKKVTLKDKSSTEEK

FNEKGEISEKTIVRANGTRLEYTDIKSDKTGKAKEVLKDFTLEGTLAADGKTTLKVTEGTVTL

SKNISKSGEITVALDDTDSSGNKKSGTWDSGTSTLTISKNRTKTKQLVFTKEDTITVQNYDSAG

TNLEGKAVEITTLKELKNALK

SEQ ID NO: 11
B. garinii (strain DK29, OspA serotype 6)

-continued

MKKYLLGIGLILALIACKQNVSSLDEKNSVSVDLPGGMTVLVSKEKDKDGKYSLEATVDKLE

LKGTSDKNNGSGTLEGEKTDKSKVKSTIADDLSQTKFEIFKEDGKTLVSKKVTLKDKSSTEEK

FNGKGETSEKTIVRANGTRLEYTDIKSDGSGKAKEVLKDFTLEGTLAADGKTTLKVTEGTVV

LSKNILKSGEITAALDDSDTTRATKKTGKWDSKTSTLTISVNSQKTKNLVFTKEDTITVQRYDS

AGTNLEGKAVEITTLKELKNALK

SEQ ID NO: 12
*B. garinii* (strain T25, OspA serotype 7)
MKKYLLGIGLILALIACKQNVSSLDEKNSVSVDLPGEMKVLVSKEKDKDGKYSLEATVDKLE

LKGTSDKNNGSGVLEGVKAAKSKAKLTIADDLSQTKFEIFKEDGKTLVSKKVTLKDKSSTEE

KFNDKGKLSEKVVTRANGTRLEYTEIQNDGSGKAKEVLKSLTLEGTLTADGETKLTVEAGTV

TLSKNISESGEITVELKDTETTPADKKSGTWDSKTSTLTISKNSQKTKQLVFTKENTITVQKYN

TAGTKLEGSPAEIKDLEALKAALK

SEQ ID NO: 13
*Borrelia* OspA lipidation signal
MKKYLLGIGLILALIA

SEQ ID NO: 14
*Borrelia* OspB lipidation signal
MRLLIGFALALALIG

SEQ ID NO: 15
*E. coli* lpp lipidation signal
MKATKLVLGAVILGSTLLAG

SEQ ID NO: 16
LN1 peptide linker constructed from two separate loop regions
of the N-terminal half of OspA from *B. burgdorferi* s.s. strain
B31 (aa 65-74 and aa 42-53, amino acid exchange at position
53: D53S)
GTSDKNNGSGSKEKNKDGKYS SEQ ID NO: 17
hLFA-1-like sequence from *B. burgdorferi* s.s. strain B31
(OspA serotype 1)
GYVLEGTLTAE SEQ ID NO: 18
Non-hLFA-1-like sequence from *B. afzelii* strain K78
(OspA serotype 2)
NFTLEGKVAND SEQ ID NO: 19
*B. burgdorferi* s.s. (strain B31, serotype 1), OspA aa 126-273
with replaced hLFA-like sequence from serotype 1 OspA
FNEKGEVSEKIITRADGTRLEYTGIKSDGSGKAKEVLKNFTLEGKVANDKTTLVVKEGTVTLS

KNISKSGEVSVELNDTDSSAATKKTAAWNSGTSTLTITVNSKKTKDLVFTKENTITVQQYDSN

GTKLEGSAVEITKLDEIKNALK

SEQ ID NO: 20
*B. afzelii* (strain K78, serotype 2), OspA aa 126-273
FNEKGELSAKTMTRENGTKLEYTEMKSDGTGKAKEVLKNFTLEGKVANDKVTLEVKEGTVT

LSKEIAKSGEVTVALNDTNTTQATKKTGAWDSKTSTLTISVNSKKTTQLVFTKQDTITVQKYD

SAGTNLEGTAVEIKTLDELKNALK

SEQ ID NO: 21
*B. garinii* (strain PBr, serotype 3), OspA aa 126-274
FNDKGKLSEKVVTRANGTRLEYTEIKNDGSGKAKEVLKGFALEGTLTDGGETKLTVTEGTVT

LSKNISKSGEITVALNDTETTPADKKTGEWKSDTSTLTISKNSQKPKQLVFTKENTITVQNYNR

AGNALEGSPAEIKDLAELKAALK

SEQ ID NO: 22
*B. bavariensis* (strain PBi, serotype 4), OspA aa 126-273
FNAKGELSEKTILRANGTRLEYTEIKSDGTGKAKEVLKDFALEGTLAADKTTLKVTEGTVVLS -continued

KHIPNSGEITVELNDSNSTQATKKTGKWDSNTSTLTISVNSKKTKNIVFTKEDTITVQKYDSAG

TNLEGNAVEIKTLDELKNALK

SEQ ID NO: 23
B. garinii (strain PHei, serotype 5), OspA aa 126-273
FNEKGEISEKTIVRANGTRLEYTDIKSDKTGKAKEVLKDFTLEGTLAADGKTTLKVTEGTVTL

SKNISKSGEITVALDDTDSSGNKKSGTWDSGTSTLTISKNRTKTKQLVFTKEDTITVQNYDSAG

TNLEGKAVEITTLKELKNALK

SEQ ID NO: 24
B. garinii (strain DK29, serotype 6), OspA aa 126-274
FNGKGETSEKTIVRANGTRLEYTDIKSDGSGKAKEVLKDFTLEGTLAADGKTTLKVTEGTVV

LSKNILKSGEITAALDDSDTTRATKKTGKWDSKTSTLTISVNSQKTKNLVFTKEDTITVQRYDS

AGTNLEGKAVEITTLKELKNALK

SEQ ID NO: 25
B. garinii (strain T25, serotype 7) OspA aa 126-274
FNDKGKLSEKVVTRANGTRLEYTEIQNDGSGKAKEVLKSLTLEGTLTADGETKLTVEAGTVT

LSKNISESGEITVELKDTETTPADKKSGTWDSKTSTLTISKNSQKTKQLVFTKENTITVQKYNT

AGTKLEGSPAEIKDLEALKAALK

SEQ ID NO: 26
Lip-S4D1-S3hybD1-nt Coding sequence for intermediate and
final heterodimer fusion proteins of OspA serotype 4 and
OspA serotype 3 with disulfide bond type 1, E. coli lpp
lipidation signal, LN1 linker sequence, serotype 3 OspA
fragment comprising amino acids 125-176 of B. valaisiana,
strain VS116 (SEQ ID NO: 2) and amino acids 177-274 of B.
garinii, strain PBr, serotype 3

(SEQ ID NO: 3)
ATGAAAGCTACTAAACTGGTACTGGGCGCGGTAATCCTGGGTTCTACTCTGCTGGCAGGT

TGCTCAAGCTTCAATGCTAAGGGCGAACTGAGCGAAAAAACGATCCTGCGTGCGAATGG

CACCCGTCTGGAATACACCGAAATCAAATCCGATGGTACGGGCAAAGCAAAGGAAGTCC

TGAAAGATTTTGCTCTGGAAGGTACCCTGGCGGCCGACAAAACCACGCTGAAGGTGACGT

GCGGCACCGTGGTTCTGAGCAAACATATTCCGAACTCTGGTGAAATCACCGTTGAACTGA

ACGATAGCAATTCTACGCAGGCAACCAAAAAGACGGGCAAATGGGACAGTAATACCTCC

ACGCTGACCATTTCAGTCAACTCGAAAAAGACCAAAAATATTGTGTTCACGAAGGAAGAT

ACGATCACCGTTCAAAAATATGACTCCGCGGGCACCAACCTGGAAGGCAATGCCGTCGA

AATCAAAACCCTGGATGAACTGTGTAACGCCCTGAAGGGTACTAGTGACAAAAACAATG

GCTCTGGTAGCAAAGAGAAAAACAAAGATGGCAAGTACTCATTCAACGAAAAAGGCGAA

GTGAGCGAAAAAATTCTGACCCGTAGCAATGGCACCACCCTGGAATATAGCCAGATGAC

CGATGCAGAAAATGCAACCAAAGCAGTTGAAACCCTGAAAAACGGTATTAAACTGCCTG

GTAATCTGGTTGGTGGTAAAACCAAACTGACCGTTACCTGTGGCACCGTTACCCTGAGCA

AAAACATTAGCAAAAGCGGTGAAATTACCGTGGCACTGAATGATACCGAAACCACACCG

GCAGACAAAAAACCGGTGAATGGAAAAGCGATACCAGCACCCTGACCATTAGTAAAAA

TAGCCAGAAAACAAAACAGCTGGTGTTTACCAAAGAAAACACCATTACCGTGCAGAATT

ATAACCGTGCAGGTAATGCACTGGAAGGTAGTCCGGCAGAAATTAAAGATCTGGCAGAA

CTGTGTGCAGCCCTGAAATAA

SEQ ID NO: 27
Lip-S4D1-S3hybD1-aa: Heterodimer fusion protein of OspA
serotype 4 and OspA serotype 3, comprising amino acids
125-176 of B. valaisiana, strain VS116 (SEQ ID NO: 2)
and amino acids 177-274 of B. garinii, strain PBr,
serotype 3 (SEQ ID NO: 3), with disulfide bond type 1, N-terminal CSS for addition of lipids, LN1 linker sequence, N-terminal lipidation Lip
LipCSSFNAKGELSEKTILRANGTRLEYTEIKSDGTGKAKEVLKDFALEGTLAADKTTLKVTCG

TVVLSKHIPNSGEITVELNDSNSTQATKKTGKWDSNTSTLTISVNSKKTKNIVFTKEDTITVQK

YDSAGTNLEGNAVEIKTLDELCNALKGTSDKNNGSGSKEKNKDGKYSFNEKGEVSEKILTRS

NGTTLEYSQMTDAENATKAVETLKNGIKLPGNLVGGKTKLTVTCGTVTLSKNISKSGEITVAL

NDTETTPADKKTGEWKSDTSTLTISKNSQKTKQLVFTKENTITVQNYNRAGNALEGSPAEIKD

LAELCAALK

SEQ ID NO: 28

Lip-S1D1-S2D1-nt: Coding sequence for intermediate and final heterodimer fusion proteins of OspA serotype 1 and OspA serotype 2 with disulfide bond type 1, E. coli lpp lipidation signal, LN1 linker sequence, aa 164-174 of OspA serotype 1 replaced by non-hLFA-1-like sequence NFTLEGKVAND

ATGAAAGCTACTAAACTGGTACTGGGCGCGGTAATCCTGGGTTCTACTCTGCTGGCAGGT

TGCTCAAGCTTCAACGAAAAGGGCGAAGTCAGCGAAAAAATCATTACCCGCGCAGACGG

CACCCGCCTGGAATACACCGGCATCAAATCGGACGGCAGCGGCAAAGCGAAAGAAGTTC

TGAAAAACTTTACCCTGGAAGGCAAAGTCGCAAATGATAAAACCACCCTGGTGGTGAAA

TGCGGCACCGTTACGCTGAGCAAAAACATTAGTAAATCCGGTGAAGTCTCTGTGGAACTG

AATGATACCGACAGCTCTGCGGCCACCAAGAAAACCGCAGCTTGGAACTCAGGCACCTC

GACGCTGACCATTACGGTTAATAGCAAGAAAACCAAAGATCTGGTCTTCACGAAAGAAA

ACACCATCACGGTGCAGCAATATGACAGCAATGGTACCAAACTGGAAGGCTCCGCTGTG

GAAATCACGAAACTGGATGAAATCTGTAATGCTCTGAAAGGTACTAGTGACAAAAACAA

TGGCTCTGGTAGCAAAGAGAAAAACAAAGATGGCAAGTACTCATTCAACGAAAAGGCG

AACTGTCGGCGAAAACGATGACGCGTGAAAACGGCACCAAACTGGAATATACGGAAATG

AAAAGCGATGGCACCGGTAAAGCGAAAGAAGTTCTGAAAAACTTTACCCTGGAAGGCAA

AGTCGCCAATGACAAAGTCACCCTGGAAGTGAAATGCGGCACCGTTACGCTGTCAAAAG

AAATTGCAAAATCGGGTGAAGTGACCGTTGCTCTGAACGATACGAATACCACGCAAGCG

ACCAAGAAAACCGGCGCCTGGGACAGCAAAACCTCTACGCTGACCATTAGTGTTAATAG

CAAGAAAACCACGCAGCTGGTCTTCACCAAACAAGATACGATCACCGTGCAGAAATACG

ACAGTGCGGGTACCAACCTGGAAGGCACGGCTGTTGAAATCAAAACCCTGGACGAACTG

TGTAACGCCCTGAAA

SEQ ID NO: 29

Lip-S1D1-S2D1-aa: Heterodimer fusion protein of OspA serotype 1 and OspA serotype 2 with disulfide bond type 1, N-terminal CSS for addition of lipids, LN1 linker sequence, aa 164-174 of OspA serotype 1 replaced by non-hLFA-1-like sequence NFTLEGKVAND, N-terminal lipidation
LipCSSFNEKGEVSEKIITRADGTRLEYTGIKSDGSGKAKEVLKNFTLEGKVANDKTTLVVKCG

TVTLSKNISKSGEVSVELNDTDSSAATKKTAAWNSGTSTLTITVNSKKTKDLVFTKENTITVQ

QYDSNGTKLEGSAVEITKLDEICNALKGTSDKNNGSGSKEKNKDGKYSFNEKGELSAKTMTR

ENGTKLEYTEMKSDGTGKAKEVLKNFTLEGKVANDKVTLEVKCGTVTLSKEIAKSGEVTVA

LNDTNTTQATKKTGAWDSKTSTLTISVNSKKTTQLVFTKQDTITVQKYDSAGTNLEGTAVEIK

TLDELCNALK

SEQ ID NO: 30

Lip-S4D1-S3D1-nt: Coding sequence for intermediate and final heterodimer fusion proteins of OspA serotypes 4 and 3 both with disulfide bond type 1, E. coli lpp -continued lipidation signal, N-terminal CSS for addition of
lipids, LN1 linker sequence
ATGAAAGCTACTAAACTGGTACTGGGCGCGGTAATCCTGGGTTCTACTCTGCTGGCAGGT

TGCTCAAGCTTCAATGCTAAGGGCGAACTGAGCGAAAAAACGATCCTGCGTGCGAATGG

CACCCGTCTGGAATACACCGAAATCAAATCCGATGGTACGGGCAAAGCAAAGGAAGTCC

TGAAAGATTTTGCTCTGGAAGGTACCCTGGCGGCCGACAAAACCACGCTGAAGGTGACGT

GCGGCACCGTGGTTCTGAGCAAACATATTCCGAACTCTGGTGAAATCACCGTTGAACTGA

ACGATAGCAATTCTACGCAGGCAACCAAAAAGACGGGCAAATGGGACAGTAATACCTCC

ACGCTGACCATTTCAGTCAACTCGAAAAAGACCAAAAATATTGTGTTCACGAAGGAAGAT

ACGATCACCGTTCAAAAATATGACTCCGCGGGCACCAACCTGGAAGGCAATGCCGTCGA

AATCAAAACCCTGGATGAACTGTGTAACGCCCTGAAGGGTACTAGTGACAAAAACAATG

GCTCTGGTAGCAAAGAGAAAAACAAAGATGGCAAGTACTCATTTAACGATAAGGGCAAA

CTGTCGGAAAAAGTGGTCACCCGCGCAAATGGCACCCGCCTGGAATACACGGAAATCAA

AAACGATGGTAGCGGCAAAGCGAAGGAAGTTCTGAAAGGCTTTGCCCTGGAAGGTACCC

TGACGGATGGCGGTGAAACCAAACTGACCGTGACGTGCGGCACCGTTACGCTGTCTAAA

AACATTAGCAAGTCTGGTGAAATCACGGTCGCACTGAATGATACCGAAACCACGCCGGCT

GACAAAAAGACCGGCGAATGGAAAAGTGACACCTCCACGCTGACCATTTCAAAGAACTC

GCAGAAACCGAAGCAACTGGTCTTCACCAAAGAAAACACGATCACCGTGCAGAACTATA

ATCGTGCCGGTAATGCTCTGGAAGGCTCACCGGCTGAAATCAAGGACCTGGCTGAACTGT

GTGCGGCACTGAAA

SEQ ID NO: 31
Lip-S4D1-S3D1-aa: Heterodimer fusion protein of OspA
serotypes 4 and 3 both with disulfide bond type 1,
N-terminal CSS for addition of lipids, LN1 linker
sequence, N-terminal lipidation
LipCSSFNAKGELSEKTILRANGTRLEYTEIKSDGTGKAKEVLKDFALEGTLAADKTTLKVTCG

TVVLSKHIPNSGEITVELNDSNSTQATKKTGKWDSNTSTLTISVNSKKTKNIVFTKEDTITVQK

YDSAGTNLEGNAVEIKTLDELCNALKGTSDKNNGSGSKEKNKDGKYSFNDKGKLSEKVVTR

ANGTRLEYTEIKNDGSGKAKEVLKGFALEGTLTDGGETKLTVTCGTVTLSKNISKSGEITVAL

NDTETTPADKKTGEWKSDTSTLTISKNSQKPKQLVFTKENTITVQNYNRAGNALEGSPAEIKD

LAELCAALK

SEQ ID NO: 32
Lip-S5D1-S6D1-nt: Coding sequence for intermediate and
final heterodimer fusion proteins of OspA serotypes 6
both with disulfide bond type 1, E. coli lpp lipidation
signal, N-terminal CSS for addition of lipids, LN1
linker sequence
ATGAAAGCTACTAAACTGGTACTGGGCGCGGTAATCCTGGGTTCTACTCTGCTGGCAGGT

TGCTCAAGCTTCAACGAAAAGGGCGAAATCTCAGAAAAAACCATCGTCCGCGCTAACGG

CACCCGCCTGGAATACACCGACATCAAATCAGACAAGACCGGTAAAGCGAAGGAAGTTC

TGAAAGATTTTACGCTGGAAGGTACCCTGGCAGCAGACGGTAAAACCACGCTGAAGGTG

ACCTGCGGTACCGTTACGCTGTCCAAAAACATTAGTAAGTCCGGCGAAATCACGGTCGCC

CTGGATGACACCGATAGCTCTGGCAACAAAAAGAGCGGTACCTGGGATTCAGGCACCTC

GACGCTGACCATTTCTAAAAATCGTACGAAAACCAAGCAGCTGGTCTTCACGAAAGAAG

ATACGATCACCGTGCAAAACTATGACAGCGCAGGTACCAATCTGGAAGGCAAAGCTGTG

GAAATTACCACGCTGAAAGAACTGTGTAATGCTCTGAAAGGTACTAGTGACAAAAACAA

TGGCTCTGGTAGCAAAGAGAAAAACAAAGATGGCAAGTACTCATTCAACGGCAAAGGTG

```
AAACGAGCGAAAAGACCATCGTGCGTGCGAACGGTACCCGCCTGGAATATACGGACATT

AAATCGGACGGCAGCGGCAAAGCAAAGGAAGTCCTGAAAGATTTTACGCTGGAAGGTAC

CCTGGCAGCAGACGGTAAAACCACGCTGAAGGTGACGTGCGGCACCGTGGTTCTGTCAA

AAAACATTCTGAAGTCGGGTGAAATCACCGCAGCTCTGGATGACAGCGATACCACGCGT

GCTACGAAAAGACCGGTAAATGGGATAGCAAGACCTCTACGCTGACCATTAGTGTCAA

CTCCCAGAAAACGAAGAATCTGGTGTTCACCAAAGAAGATACGATCACCGTTCAACGCTA

TGACAGTGCGGGCACCAACCTGGAAGGCAAAGCCGTTGAAATTACCACGCTGAAAGAAC

TGTGTAATGCTCTGAAA
```

SEQ ID NO: 33
Lip-S5D1-S6D1-aa: Heterodimer fusion protein of OspA serotypes 6 both with disulfide bond type 1, N-terminal CSS for addition of lipids, LN1 linker sequence, N-terminal lipidation

```
LipCSSFNEKGEISEKTIVRANGTRLEYTDIKSDKTGKAKEVLKDFTLEGTLAADGKTTLKVTC

GTVTLSKNISKSGEITVALDDTDSSGNKKSGTWDSGTSTLTISKNRTKTKQLVFTKEDTITVQN

YDSAGTNLEGKAVEITTLKELCNALKGTSDKNNGSGSKEKNKDGKYSFNGKGETSEKTIVRA

NGTRLEYTDIKSDGSGKAKEVLKDFTLEGTLAADGKTTLKVTCGTVVLSKNILKSGEITAALD

DSDTTRATKKTGKWDSKTSTLTISVNSQKTKNLVFTKEDTITVQRYDSAGTNLEGKAVEITTL

KELCNALK
```

SEQ ID NO: 34
B. burgdorferi (strain B31, OspA serotype 1) aa 18-273, lpp lipidation signal sequence removed (MKATKLVLGAVILGSTLLAG, SEQ ID NO: 15), C-terminal His tag (LEHHHHHH), N-terminal CSSF for addition of lipids

```
CSSFKQNVSSLDEKNSVSVDLPGEMKVLVSKEKNKDGKYDLIATVDKLELKGTSDKNNGSG

VLEGVKADKSKVKLTISDDLGQTTLEVFKEDGKTLVSKKVTSKDKSSTEEKFNEKGEVSEKII

TRADGTRLEYTGIKSDGSGKAKEVLKGYVLEGTLTAEKTTLVVKEGTVTLSKNISKSGEVSVE

LNDTDSSAATKKTAAWNSGTSTLTITVNSKKTKDLVFTKENTITVQQYDSNGTKLEGSAVEIT

KLDEIKNALKLEHHHHHH
```

SEQ ID NO: 35
B. afzelii (strain K78; OspA serotype 2) aa 18-273, lpp lipidation signal sequence removed (MKATKLVLGAVILGSTLLAG, SEQ ID NO: 15), C-terminal His tag (LEHHHHHH), N-terminal CSSF for addition of lipids

```
CSSFKQNVSSLDEKNSASVDLPGEMKVLVSKEKDKDGKYSLKATVDKIELKGTSDKDNGSG

VLEGTKDDKSKAKLTIADDLSKTTFELFKEDGKTLVSRKVSSKDKTSTDEMFNEKGELSAKT

MTRENGTKLEYTEMKSDGTGKAKEVLKNFTLEGKVANDKVTLEVKEGTVTLSKEIAKSGEV

TVALNDTNTTQATKKTGAWDSKTSTLTISVNSKKTTQLVFTKQDTITVQKYDSAGTNLEGTA

VEIKTLDELKNALKLEHHHHHH
```

SEQ ID NO: 36
B. garinii (strain PBr; OspA serotype 3) aa 18-274, lpp lipidation signal sequence removed (MKATKLVLGAVILGSTLLAG, SEQ ID NO: 15), C-terminal His tag (LEHHHHHH), N-terminal CSSF for addition of lipids

```
CSSFKQNVSSLDEKNSVSVDLPGGMKVLVSKEKDKDGKYSLMATVEKLELKGTSDKSNGSG

VLEGEKADKSKAKLTISQDLNQTTFEIFKEDGKTLVSRKVNSKDKSSTEEKFNDKGKLSEKVV

TRANGTRLEYTEIKNDGSGKAKEVLKGFALEGTLTDGGETKLTVTEGTVTLSKNISKSGEITV

ALNDTETTPADKKTGEWKSDTSTLTISKNSQKTKQLVFTKENTITVQNYNRAGNALEGSPAEI

KDLAELKAALKLEHHHHHH
```

SEQ ID NO: 37
B. bavariensis (strain PBi; OspA serotype 4) aa 18-273, lpp lipidation signal sequence removed (MKATKLVLGAVILGSTLLAG, -continued SEQ ID NO: 15), C-terminal His tag (LEHHHHHH), N-terminal CSSF for addition of lipids

CSSFKQNVSSLDEKNSVSVDLPGEMKVLVSKEKDKDGKYSLMATVDKLELKGTSDKSNGSG

TLEGEKSDKSKAKLTISEDLSKTTFEIFKEDGKTLVSKKVNSKDKSSIEEKFNAKGELSEKTILR

ANGTRLEYTEIKSDGTGKAKEVLKDFALEGTLAADKTTLKVTEGTVVLSKHIPNSGEITVELN

DSNSTQATKKTGKWDSNTSTLTISVNSKKTKNIVFTKEDTITVQKYDSAGTNLEGNAVEIKTL

DELKNALKLEHHHHHH

SEQ ID NO: 38

*B. garinii* (strain PHei; OspA serotype 5) aa 18-273, lpp lipidation signal sequence removed (MKATKLVLGAVILGSTLLAG, SEQ ID NO: 15), C-terminal His tag (LEHHHHHH), N-terminal CSSF for addition of lipids

CSSFKQNVSSLDEKNSVSVDLPGGMKVLVSKEKDKDGKYSLMATVEKLELKGTSDKNNGSG

TLEGEKTDKSKVKLTIAEDLSKTTFEIFKEDGKTLVSKKVTLKDKSSTEEKFNEKGEISEKTIVR

ANGTRLEYTDIKSDKTGKAKEVLKDFTLEGTLAADGKTTLKVTEGTVTLSKNISKSGEITVAL

DDTDSSGNKKSGTWDSGTSTLTISKNRTKTKQLVFTKEDTITVQNYDSAGTNLEGKAVEITTL

KELKNALKLEHHHHHH

SEQ ID NO: 39

*B. garinii* (strain DK29; OspA serotype 6) aa 18-274,lpp lipidation signal sequence removed (MKATKLVLGAVILGSTLLAG, SEQ ID NO: 15), C-terminal His tag (LEHHHHHH), N-terminal CSSF for addition of lipids

CSSFKQNVSSLDEKNSVSVDLPGGMTVLVSKEKDKDGKYSLEATVDKLELKGTSDKNNGSG

TLEGEKTDKSKVKSTIADDLSQTKFEIFKEDGKTLVSKKVTLKDKSSTEEKFNGKGETSEKTIV

RANGTRLEYTDIKSDGSGKAKEVLKDFTLEGTLAADGKTTLKVTEGTVVLSKNILKSGEITAA

LDDSDTTRATKKTGKWDSKTSTLTISVNSQKTKNLVFTKEDTITVQRYDSAGTNLEGKAVEIT

TLKELKNALKLEHHHHHH

SEQ ID NO: 40

Chimeric OspA Serotype1/Serotype2, N-terminal lipidation, His-tagged, including the OspB lipidation signal sequence: MRLLIGFALALALIG (SEQ ID NO: 14) which is cleaved during processing

MRLLIGFALALALIGCAQKGAESIGSVSVDLPGEMKVLVSKEKDKNGKYDLIATVDKLELKG

TSDKNNGSGVLEGVKTNKSKVKLTISDDLGQTTLEVFKEDGKTLVSKKVTSKDKSSTEEKFN

EKGEVSEKIITMADGTRLEYTGIKSDGTGKAKYVLKNFTLEGKVANDKTTLEVKEGTVTLSM

NISKSGEVSVELNDTDSSAATKKTAAWNSKTSTLTISVNSKKTTQLVFTKQDTITVQKYDSAG

TNLEGTAVEIKTLDELKNALKLEHHHHHH

SEQ ID NO: 41

Chimeric OspA Serotype5/Serotype3, N-terminal lipidation, His-tagged, including the OspB lipidation signal sequence: MRLLIGFALALALIG (SEQ ID NO: 14) which is cleaved during processing

MRLLIGFALALALIGCAQKGAESIGSVSVDLPGGMKVLVSKEKDKNGKYSLMATVEKLELKG

TSDKNNGSGTLEGEKTNKSKVKLTIAEDLSKTTFEIFKEDGKTLVSKKVTLKDKSSTEEKFNE

KGEISEKTIVMANGTRLEYTDIKSDKTGKAKYVLKDFTLEGTLAADGKTTLKVTEGTVTLSM

NISKSGEITVALDDTDSSGNKKSGTWDSDTSTLTISKNSQKTKQLVFTKENTITVQNYNRAGN

ALEGSPAEIKDLAELKAALKLEHHHHHH

SEQ ID NO: 42

Chimeric OspA Serotype6/Serotype4, N-terminal lipidation, His-tagged, including the OspB lipidation signal sequence: MRLLIGFALALALIG (SEQ ID NO: 14) which is cleaved during processing

MRLLIGFALALALIGCAQKGAESIGSVSVDLPGGMTVLVSKEKDKNGKYSLEATVDKLELKG

TSDKNNGSGTLEGEKTNKSKVKLTIADDLSQTKFEIFKEDAKTLVSKKVTLKDKSSTEEKFNE

```
KGETSEKTIVMANGTRLEYTDIKSDGSGKAKYVLKDFTLEGTLAADGKTTLKVTEGTVVLSM

NILKSGEITVALDDSDTTQATKKTGKWDSNTSTLTISVNSKKTKNIVFTKEDTITVQKYDSAGT

NLEGNAVEIKTLDELKNALKLEHHHHHH
```

SEQ ID NO: 43

S1D1
```
FNEKGEVSEKIITRADGTRLEYTGIKSDGSGKAKEVLKNFTLEGKVANDKTTLVVKCGTVTLS

KNISKSGEVSVELNDTDSSAATKKTAAWNSGTSTLTITVNSKKTKDLVFTKENTITVQQYDSN

GTKLEGSAVEITKLDEICNALK
```

SEQ ID NO: 44

S2D1
```
FNEKGELSAKTMTRENGTKLEYTEMKSDGTGKAKEVLKNFTLEGKVANDKVTLEVKCGTVT

LSKEIAKSGEVTVALNDTNTTQATKKTGAWDSKTSTLTISVNSKKTTQLVFTKQDTITVQKYD

SAGTNLEGTAVEIKTLDELCNALK
```

SEQ ID NO: 45

S3D1
```
FNDKGKLSEKVVTRANGTRLEYTEIKNDGSGKAKEVLKGFALEGTLTDGGETKLTVTCGTVT

LSKNISKSGEITVALNDTETTPADKKTGEWKSDTSTLTISKNSQKTKQLVFTKENTITVQNYNR

AGNALEGSPAEIKDLAELCAALK
```

SEQ ID NO: 46

S4D1
```
FNAKGELSEKTILRANGTRLEYTEIKSDGTGKAKEVLKDFALEGTLAADKTTLKVTCGTVVLS

KHIPNSGEITVELNDSNSTQATKKTGKWDSNTSTLTISVNSKKTKNIVFTKEDTITVQKYDSAG

TNLEGNAVEIKTLDELCNALK
```

SEQ ID NO: 47

S5D1
```
FNEKGEISEKTIVRANGTRLEYTDIKSDKTGKAKEVLKDFTLEGTLAADGKTTLKVTCGTVTL

SKNISKSGEITVALDDTDSSGNKKSGTWDSGTSTLTISKNRTKTKQLVFTKEDTITVQNYDSAG

TNLEGKAVEITTLKELCNALK
```

SEQ ID NO: 48

S6D1
```
FNGKGETSEKTIVRANGTRLEYTDIKSDGSGKAKEVLKDFTLEGTLAADGKTTLKVTCGTVV

LSKNILKSGEITAALDDSDTTRATKKTGKWDSKTSTLTISVNSQKTKNLVFTKEDTITVQRYDS

AGTNLEGKAVEITTLKELCNALK
```

SEQ ID NO: 49

S3HYBD1 (BVA)
```
FNEKGEVSEKILTRSNGTTLEYSQMTDAENATKAVETLKNGIKLPGNLVGGKTKLTVTCGTV

TLSKNISKSGEITVALNDTETTPADKKTGEWKSDTSTLTISKNSQKTKQLVFTKENTITVQNYN

RAGNALEGSPAEIKDLAELCAALK
```

SEQ ID NO: 50

BVAD1
```
FNEKGEVSEKILTRSNGTTLEYSQMTDAENATKAVETLKNGIKLPGNLVGGKTTLKITCGTVT

LSKHIAKSGEVTVEINDTSSTPNTKKTGKWDARNSTLTIIVDSKNKTKLVFTKQDTITVQSYNP

AGNKLEGTAVEIKTLQELCNALK
```

SEQ ID NO: 51

S3hybD1(Bsp): hybrid OspA C-terminal fragment; amino acids
126-175 from Borrelia spielmanii and amino acids 177-274
from Borrelia garinii, strain PBr, with disulfide bond type
1 and T in position 233
```
FNEKGELSEKTLVRANGTKLEYTEIKSDGTGKAKEVLKDFTLEGTLANEKTKLTVTCGTVTLS

KNISKSGEITVALNDTETTPADKKTGEWKSDTSTLTISKNSQKTKQLVFTKENTITVQNYNRA

GNALEGSPAEIKDLAELCAALK
```

-continued

SEQ ID NO: 52
MSPD1
FNEKGELSEKTLVRANGTKLEYTEIKSDGTGKAKEVLKDFTLEGTLANEKATLTVKCGTVTL

SKNIDKSGEVTVALNDTDSTAATKKTGAWDSKTSTLTITVNSKKTKDLVFTKQDTITVQKYD

SAGTTLEGSAVEIKTLDELCNALK

SEQ ID NO: 53
Forward primer for the 16S-23S intergenic spacer
GTATGTTTAGTGAGGGGGTG SEQ ID NO: 54
Reverse primer for the 16S-23S intergenic spacer
GGATCATAGCTCAGGTGGTTAG SEQ ID NO: 55
Forward nested primer for the 16S-23S intergenic spacer
AGGGGGGTGAAGTCGTAACAAG SEQ ID NO: 56
Reverse nested primer for the 16S-23S intergenic spacer
GTCTGATAAACCTGAGGTCGGA SEQ ID NO: 57
Forward primer for the RecA gene of *Borrelia*
CATGCTCTTGATCCTGTTTA SEQ ID NO: 58
Reverse primer for the RecA gene of *Borrelia*
CCCATTTCTCCATCTATCTC SEQ ID NO: 59
25-mer peptide from the Invariable Region 6 (IR6) of VlsE
MKKDDQIAAAMVLRGMAKDGQFALK SEQ ID NO: 60
Mouse cathelin
RLAGLLRKGGEKIGEKLKKIGQKIKNFFQKLVPQPE SEQ ID NO: 61
KLK peptide
KLKLLLLLKLK SEQ ID NO: 62
N-terminal peptide for lipidation
CKQN SEQ ID NO: 63
5'-(dIdC)$_{13}$-3'
dIdC dIdC dIdC dIdC dIdC dIdC dIdC dIdC dIdC dIdC dIdC dIdC dIdC The entire contents of all of the references (including literature references, issued patents, published patent applications, and co-pending patent applications) cited throughout this application are hereby expressly incorporated by reference.

---

The invention claimed is:

1. A polypeptide comprising or consisting of the amino acid sequence of SEQ ID NO: 27.

2. A pharmaceutical composition comprising the polypeptide according to claim 1, and optionally a pharmaceutically acceptable carrier or excipient.

3. The pharmaceutical composition according to claim 2, wherein the pharmaceutically acceptable excipient comprises L-methionine and/or aluminium hydroxide.

4. A pharmaceutical composition comprising the amino acid sequences of SEQ ID NO: 29, SEQ ID NO: 27 and SEQ ID NO: 33.

5. The polypeptide according to claim 1 for use in a method of treating or protecting against a *Borrelia* infection, wherein the *Borrelia* infection is a *B. burgdorferi* s.s. or *B. afzelii* infection.

6. The pharmaceutical composition according to claim 2 for use in a method of treating or protecting against a *Borrelia* infection, wherein the *Borrelia* infection is a *B. burgdorferi* s.s. or *B. afzelii* infection.

7. The pharmaceutical composition according to claim 4, wherein the pharmaceutical composition is a vaccine.

8. The pharmaceutical composition according to claim 4, further comprising a pharmaceutically acceptable carrier or excipient.

9. The pharmaceutical composition according to claim 8, wherein the pharmaceutically acceptable excipient comprises L-methionine and/or aluminium hydroxide.

10. The pharmaceutical composition according to claim 2, wherein the pharmaceutical composition is a vaccine.

11. The pharmaceutical composition according to claim 4 for use in a method of treating or protecting against a *Borrelia* infection, wherein the *Borrelia* infection is *B. burgdorferi* s.s. or *B. afzelii* infection.

* * * * *

SEQUENCE LISTING

<160> NUMBER OF SEQ ID NOS: 65

<210> SEQ ID NO 1
<211> LENGTH: 150
<212> TYPE: PRT
<213> ORGANISM: Artificial Sequence
<220> FEATURE:
<223> OTHER INFORMATION: S3hybD1

<400> SEQUENCE: 1

Phe Asn Glu Lys Gly Glu Val Ser Glu Lys Ile Leu Thr Arg Ser Asn
1               5                   10                  15

Gly Thr Thr Leu Glu Tyr Ser Gln Met Thr Asp Ala Glu Asn Ala Thr
            20                  25                  30

```
Lys Ala Val Glu Thr Leu Lys Asn Gly Ile Lys Leu Pro Gly Asn Leu
            35                  40                  45

Val Gly Gly Lys Thr Lys Leu Thr Val Thr Cys Gly Thr Val Thr Leu
 50                  55                  60

Ser Lys Asn Ile Ser Lys Ser Gly Glu Ile Thr Val Ala Leu Asn Asp
 65                  70                  75                  80

Thr Glu Thr Thr Pro Ala Asp Lys Lys Thr Gly Glu Trp Lys Ser Asp
                 85                  90                  95

Thr Ser Thr Leu Thr Ile Ser Lys Asn Ser Gln Lys Thr Lys Gln Leu
                100                 105                 110

Val Phe Thr Lys Glu Asn Thr Ile Thr Val Gln Asn Tyr Asn Arg Ala
            115                 120                 125

Gly Asn Ala Leu Glu Gly Ser Pro Ala Glu Ile Lys Asp Leu Ala Glu
        130                 135                 140

Leu Cys Ala Ala Leu Lys
145                 150

<210> SEQ ID NO 2
<211> LENGTH: 52
<212> TYPE: PRT
<213> ORGANISM: Borrelia valaisiana

<400> SEQUENCE: 2

Phe Asn Glu Lys Gly Glu Val Ser Glu Lys Ile Leu Thr Arg Ser Asn
 1               5                  10                  15

Gly Thr Thr Leu Glu Tyr Ser Gln Met Thr Asp Ala Glu Asn Ala Thr
             20                  25                  30

Lys Ala Val Glu Thr Leu Lys Asn Gly Ile Lys Leu Pro Gly Asn Leu
            35                  40                  45

Val Gly Gly Lys
 50

<210> SEQ ID NO 3
<211> LENGTH: 98
<212> TYPE: PRT
<213> ORGANISM: Borrelia garinii

<400> SEQUENCE: 3

Thr Lys Leu Thr Val Thr Cys Gly Thr Val Thr Leu Ser Lys Asn Ile
 1               5                  10                  15

Ser Lys Ser Gly Glu Ile Thr Val Ala Leu Asn Asp Thr Glu Thr Thr
             20                  25                  30

Pro Ala Asp Lys Lys Thr Gly Glu Trp Lys Ser Asp Thr Ser Thr Leu
            35                  40                  45

Thr Ile Ser Lys Asn Ser Gln Lys Thr Lys Gln Leu Val Phe Thr Lys
 50                  55                  60

Glu Asn Thr Ile Thr Val Gln Asn Tyr Asn Arg Ala Gly Asn Ala Leu
 65                  70                  75                  80

Glu Gly Ser Pro Ala Glu Ile Lys Asp Leu Ala Glu Leu Cys Ala Ala
             85                  90                  95

Leu Lys

<210> SEQ ID NO 4
<211> LENGTH: 274
<212> TYPE: PRT
<213> ORGANISM: Borrelia valaisiana

<400> SEQUENCE: 4
```

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Ala Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Val Ala Thr Val Asp Lys Val Glu Leu Lys
    50                  55                  60

Gly Thr Ser Asp Lys Asn Asn Gly Ser Gly Thr Leu Glu Gly Val Lys
65                  70                  75                  80

Asp Asp Lys Ser Lys Val Lys Leu Thr Ile Ser Asp Asp Leu Gly Glu
            85                  90                  95

Thr Lys Leu Glu Thr Phe Lys Glu Asp Gly Thr Leu Val Ser Arg Lys
        100                 105                 110

Val Asn Phe Lys Asp Lys Ser Phe Thr Glu Glu Lys Phe Asn Glu Lys
            115                 120                 125

Gly Glu Val Ser Glu Lys Ile Leu Thr Arg Ser Asn Gly Thr Thr Leu
    130                 135                 140

Glu Tyr Ser Gln Met Thr Asp Ala Glu Asn Ala Thr Lys Ala Val Glu
145                 150                 155                 160

Thr Leu Lys Asn Gly Ile Lys Leu Pro Gly Asn Leu Val Gly Gly Lys
            165                 170                 175

Thr Thr Leu Lys Ile Thr Glu Gly Thr Val Thr Leu Ser Lys His Ile
        180                 185                 190

Ala Lys Ser Gly Glu Val Thr Val Glu Ile Asn Asp Thr Ser Ser Thr
    195                 200                 205

Pro Asn Thr Lys Lys Thr Gly Lys Trp Asp Ala Arg Asn Ser Thr Leu
210                 215                 220

Thr Ile Ile Val Asp Ser Lys Asn Lys Thr Lys Leu Val Phe Thr Lys
225                 230                 235                 240

Gln Asp Thr Ile Thr Val Gln Ser Tyr Asn Pro Ala Gly Asn Lys Leu
            245                 250                 255

Glu Gly Thr Ala Val Glu Ile Lys Thr Leu Gln Glu Leu Lys Asn Ala
        260                 265                 270

Leu Lys

<210> SEQ ID NO 5
<211> LENGTH: 273
<212> TYPE: PRT
<213> ORGANISM: Borrelia burgdorferi

<400> SEQUENCE: 5

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
            85                  90                  95
```

```
Thr Thr Leu Glu Val Phe Lys Glu Asp Gly Lys Thr Leu Val Ser Lys
             100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Gly Tyr Val Leu Glu Gly Thr Leu Thr Ala Glu Lys Thr
                165                 170                 175

Thr Leu Val Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Gly Thr Ser Thr Leu Thr
    210                 215                 220

Ile Thr Val Asn Ser Lys Lys Thr Lys Asp Leu Val Phe Thr Lys Glu
225                 230                 235                 240

Asn Thr Ile Thr Val Gln Gln Tyr Asp Ser Asn Gly Thr Lys Leu Glu
                245                 250                 255

Gly Ser Ala Val Glu Ile Thr Lys Leu Asp Glu Ile Lys Asn Ala Leu
            260                 265                 270

Lys

<210> SEQ ID NO 6
<211> LENGTH: 273
<212> TYPE: PRT
<213> ORGANISM: Borrelia afzelii

<400> SEQUENCE: 6

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Ala Ser Val
            20                  25                  30

Asp Leu Pro Gly Glu Met Lys Val Leu Val Ser Lys Glu Lys Asp Lys
        35                  40                  45

Asp Gly Lys Tyr Ser Leu Lys Ala Thr Val Asp Lys Ile Glu Leu Lys
    50                  55                  60

Gly Thr Ser Asp Lys Asp Asn Gly Ser Gly Val Leu Glu Gly Thr Lys
65                  70                  75                  80

Asp Asp Lys Ser Lys Ala Lys Leu Thr Ile Ala Asp Asp Leu Ser Lys
                85                  90                  95

Thr Thr Phe Glu Leu Phe Lys Glu Asp Gly Lys Thr Leu Val Ser Arg
            100                 105                 110

Lys Val Ser Ser Lys Asp Lys Thr Ser Thr Asp Glu Met Phe Asn Glu
        115                 120                 125

Lys Gly Glu Leu Ser Ala Lys Thr Met Thr Arg Glu Asn Gly Thr Lys
    130                 135                 140

Leu Glu Tyr Thr Glu Met Lys Ser Asp Gly Thr Gly Lys Ala Lys Glu
145                 150                 155                 160

Val Leu Lys Asn Phe Thr Leu Glu Gly Lys Val Ala Asn Asp Lys Val
                165                 170                 175

Thr Leu Glu Val Lys Glu Gly Thr Val Thr Leu Ser Lys Glu Ile Ala
            180                 185                 190
```

Lys Ser Gly Glu Val Thr Val Ala Leu Asn Asp Thr Asn Thr Thr Gln
            195                 200                 205

Ala Thr Lys Lys Thr Gly Ala Trp Asp Ser Lys Thr Ser Thr Leu Thr
210                 215                 220

Ile Ser Val Asn Ser Lys Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
            245                 250                 255

Gly Thr Ala Val Glu Ile Lys Thr Leu Asp Glu Leu Lys Asn Ala Leu
            260                 265                 270

Lys

<210> SEQ ID NO 7
<211> LENGTH: 274
<212> TYPE: PRT
<213> ORGANISM: Borrelia garinii

<400> SEQUENCE: 7

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Lys Val Leu Val Ser Lys Glu Lys Asp Lys
        35                  40                  45

Asp Gly Lys Tyr Ser Leu Met Ala Thr Val Glu Lys Leu Glu Leu Lys
    50                  55                  60

Gly Thr Ser Asp Lys Ser Asn Gly Ser Gly Val Leu Glu Gly Glu Lys
65                  70                  75                  80

Ala Asp Lys Ser Lys Ala Lys Leu Thr Ile Ser Gln Asp Leu Asn Gln
            85                  90                  95

Thr Thr Phe Glu Ile Phe Lys Glu Asp Gly Lys Thr Leu Val Ser Arg
            100                 105                 110

Lys Val Asn Ser Lys Asp Lys Ser Ser Thr Glu Glu Lys Phe Asn Asp
            115                 120                 125

Lys Gly Lys Leu Ser Glu Lys Val Val Thr Arg Ala Asn Gly Thr Arg
130                 135                 140

Leu Glu Tyr Thr Glu Ile Lys Asn Asp Gly Ser Gly Lys Ala Lys Glu
145                 150                 155                 160

Val Leu Lys Gly Phe Ala Leu Glu Gly Thr Leu Thr Asp Gly Gly Glu
            165                 170                 175

Thr Lys Leu Thr Val Thr Gly Thr Val Thr Leu Ser Lys Asn Ile
            180                 185                 190

Ser Lys Ser Gly Glu Ile Thr Val Ala Leu Asn Asp Thr Glu Thr Thr
            195                 200                 205

Pro Ala Asp Lys Lys Thr Gly Glu Trp Lys Ser Asp Thr Ser Thr Leu
210                 215                 220

Thr Ile Ser Lys Asn Ser Gln Lys Pro Lys Gln Leu Val Phe Thr Lys
225                 230                 235                 240

Glu Asn Thr Ile Thr Val Gln Asn Tyr Asn Arg Ala Gly Asn Ala Leu
            245                 250                 255

Glu Gly Ser Pro Ala Glu Ile Lys Asp Leu Ala Glu Leu Lys Ala Ala
            260                 265                 270

Leu Lys

-continued

<210> SEQ ID NO 8
<211> LENGTH: 274
<212> TYPE: PRT
<213> ORGANISM: Borrelia garinii

<400> SEQUENCE: 8

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
                20                  25                  30

Asp Leu Pro Gly Gly Met Lys Val Leu Val Ser Lys Glu Lys Asp Lys
            35                  40                  45

Asp Gly Lys Tyr Ser Leu Met Ala Thr Val Glu Lys Leu Glu Leu Lys
        50                  55                  60

Gly Thr Ser Asp Lys Ser Asn Gly Ser Gly Val Leu Glu Gly Glu Lys
65                  70                  75                  80

Ala Asp Lys Ser Lys Ala Lys Leu Thr Ile Ser Gln Asp Leu Asn Gln
                85                  90                  95

Thr Thr Phe Glu Ile Phe Lys Glu Asp Gly Lys Thr Leu Val Ser Arg
            100                 105                 110

Lys Val Asn Ser Lys Asp Lys Ser Ser Thr Glu Glu Lys Phe Asn Asp
        115                 120                 125

Lys Gly Lys Leu Ser Glu Lys Val Val Thr Arg Ala Asn Gly Thr Arg
130                 135                 140

Leu Glu Tyr Thr Glu Ile Lys Asn Asp Gly Ser Gly Lys Ala Lys Glu
145                 150                 155                 160

Val Leu Lys Gly Phe Ala Leu Glu Gly Thr Leu Thr Asp Gly Gly Glu
                165                 170                 175

Thr Lys Leu Thr Val Thr Glu Gly Thr Val Thr Leu Ser Lys Asn Ile
            180                 185                 190

Ser Lys Ser Gly Glu Ile Thr Val Ala Leu Asn Asp Thr Glu Thr Thr
        195                 200                 205

Pro Ala Asp Lys Lys Thr Gly Glu Trp Lys Ser Asp Thr Ser Thr Leu
    210                 215                 220

Thr Ile Ser Lys Asn Ser Gln Lys Thr Lys Gln Leu Val Phe Thr Lys
225                 230                 235                 240

Glu Asn Thr Ile Thr Val Gln Asn Tyr Asn Arg Ala Gly Asn Ala Leu
                245                 250                 255

Glu Gly Ser Pro Ala Glu Ile Lys Asp Leu Ala Glu Leu Lys Ala Ala
            260                 265                 270

Leu Lys

<210> SEQ ID NO 9
<211> LENGTH: 273
<212> TYPE: PRT
<213> ORGANISM: Borrelia bavariensis

<400> SEQUENCE: 9

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asp Lys
            35                  40                  45

Asp Gly Lys Tyr Ser Leu Met Ala Thr Val Asp Lys Leu Glu Leu Lys
        50                  55                  60

```
Gly Thr Ser Asp Lys Ser Asn Gly Ser Gly Thr Leu Glu Gly Glu Lys
 65                  70                  75                  80

Ser Asp Lys Ser Lys Ala Lys Leu Thr Ile Ser Glu Asp Leu Ser Lys
                 85                  90                  95

Thr Thr Phe Glu Ile Phe Lys Glu Asp Gly Lys Thr Leu Val Ser Lys
            100                 105                 110

Lys Val Asn Ser Lys Asp Lys Ser Ser Ile Glu Glu Lys Phe Asn Ala
        115                 120                 125

Lys Gly Glu Leu Ser Glu Lys Thr Ile Leu Arg Ala Asn Gly Thr Arg
    130                 135                 140

Leu Glu Tyr Thr Glu Ile Lys Ser Asp Gly Thr Gly Lys Ala Lys Glu
145                 150                 155                 160

Val Leu Lys Asp Phe Ala Leu Glu Gly Thr Leu Ala Ala Asp Lys Thr
                165                 170                 175

Thr Leu Lys Val Thr Glu Gly Thr Val Val Leu Ser Lys His Ile Pro
            180                 185                 190

Asn Ser Gly Glu Ile Thr Val Glu Leu Asn Asp Ser Asn Ser Thr Gln
        195                 200                 205

Ala Thr Lys Lys Thr Gly Lys Trp Asp Ser Asn Thr Ser Thr Leu Thr
    210                 215                 220

Ile Ser Val Asn Ser Lys Lys Thr Lys Asn Ile Val Phe Thr Lys Glu
225                 230                 235                 240

Asp Thr Ile Thr Val Gln Lys Tyr Asp Ser Ala Gly Thr Asn Leu Glu
                245                 250                 255

Gly Asn Ala Val Glu Ile Lys Thr Leu Asp Glu Leu Lys Asn Ala Leu
            260                 265                 270

Lys

<210> SEQ ID NO 10
<211> LENGTH: 273
<212> TYPE: PRT
<213> ORGANISM: Borrelia garinii

<400> SEQUENCE: 10

Met Lys Lys Tyr Leu Leu Gly Ile Gly Leu Ile Leu Ala Leu Ile Ala
 1               5                  10                  15

Cys Lys Gln Asn Val Ser Ser Leu Asp Glu Lys Asn Ser Val Ser Val
                 20                  25                  30

Asp Leu Pro Gly Gly Met Lys Val Leu Val Ser Lys Glu Lys Asp Lys
            35                  40                  45

Asp Gly Lys Tyr Ser Leu Met Ala Thr Val Glu Lys Leu Glu Leu Lys
    50                  55                  60

Gly Thr Ser Asp Lys Asn Gly Ser Gly Thr Leu Glu Gly Glu Lys
 65                  70                  75                  80

Thr Asp Lys Ser Lys Val Lys Leu Thr Ile Ala Glu Asp Leu Ser Lys
                 85                  90                  95

Thr Thr Phe Glu Ile Phe Lys Glu Asp Gly Lys Thr Leu Val Ser Lys
            100                 105                 110

Lys Val Thr Leu Lys Asp Lys Ser Ser Thr Glu Glu Lys Phe Asn Glu
        115                 120                 125

Lys Gly Glu Ile Ser Glu Lys Thr Ile Val Arg Ala Asn Gly Thr Arg
    130                 135                 140

Leu Glu Tyr Thr Asp Ile Lys Ser Asp Lys Thr Gly Lys Ala Lys Glu
145                 150                 155                 160
```

```
Val Leu Lys Asp Phe Thr Leu Glu Gly Thr Leu Ala Ala Asp Gly Lys
                165                 170                 175

Thr Thr Leu Lys Val Thr Glu Gly Thr Val Thr Leu Ser Lys Asn Ile
            180                 185                 190

Ser Lys Ser Gly Glu Ile Thr Val Ala Leu Asp Asp Thr Asp Ser Ser
        195                 200                 205

Gly Asn Lys Lys Ser Gly Thr Trp Asp Ser Gly Thr Ser Thr Leu Thr
    210                 215                 220

Ile Ser Lys Asn Arg Thr Lys Thr Lys Gln Leu Val Phe Thr Lys Glu
225                 230                 235                 240

Asp Thr Ile Thr Val Gln Asn Tyr Asp Ser Ala Gly Thr Asn Leu Glu
                245                 250                 255

Gly Lys Ala Val Glu Ile Thr Thr Leu Lys Glu Leu Lys Asn Ala Leu
                260                 265                 270

Lys

<210> SEQ ID NO 11
<211> LENGTH: 274
<212> TYPE: PRT
<213> ORGANISM: Borrelia garinii

<400> SEQUENCE: 11

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Thr Val Leu Val Ser Lys Glu Lys Asp Lys
        35                  40                  45

Asp Gly Lys Tyr Ser Leu Glu Ala Thr Val Asp Lys Leu Glu Leu Lys
    50                  55                  60

Gly Thr Ser Asp Lys Asn Asn Gly Ser Gly Thr Leu Glu Gly Glu Lys
65                  70                  75                  80

Thr Asp Lys Ser Lys Val Lys Ser Thr Ile Ala Asp Asp Leu Ser Gln
                85                  90                  95

Thr Lys Phe Glu Ile Phe Lys Glu Asp Gly Lys Thr Leu Val Ser Lys
            100                 105                 110

Lys Val Thr Leu Lys Asp Lys Ser Ser Thr Glu Glu Lys Phe Asn Gly
        115                 120                 125

Lys Gly Glu Thr Ser Glu Lys Thr Ile Val Arg Ala Asn Gly Thr Arg
    130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
            180                 185                 190

Leu Lys Ser Gly Glu Ile Thr Ala Ala Leu Asp Asp Ser Asp Thr Thr
        195                 200                 205

Arg Ala Thr Lys Lys Thr Gly Lys Trp Asp Ser Lys Thr Ser Thr Leu
    210                 215                 220

Thr Ile Ser Val Asn Ser Gln Lys Thr Lys Asn Leu Val Phe Thr Lys
225                 230                 235                 240

Glu Asp Thr Ile Thr Val Gln Arg Tyr Asp Ser Ala Gly Thr Asn Leu
                245                 250                 255
```

Glu Gly Lys Ala Val Glu Ile Thr Thr Leu Lys Glu Leu Lys Asn Ala
                260                 265                 270

Leu Lys

<210> SEQ ID NO 12
<211> LENGTH: 274
<212> TYPE: PRT
<213> ORGANISM: Borrelia garinii

<400> SEQUENCE: 12

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
                20                  25                  30

Asp Leu Pro Gly Glu Met Lys Val Leu Val Ser Lys Glu Lys Asp Lys
            35                  40                  45

Asp Gly Lys Tyr Ser Leu Glu Ala Thr Val Asp Lys Leu Glu Leu Lys
        50                  55                  60

Gly Thr Ser Asp Lys Asn Asn Gly Ser Gly Val Leu Glu Gly Val Lys
65                  70                  75                  80

Ala Ala Lys Ser Lys Ala Lys Leu Thr Ile Ala Asp Asp Leu Ser Gln
                85                  90                  95

Thr Lys Phe Glu Ile Phe Lys Glu Asp Gly Lys Thr Leu Val Ser Lys
            100                 105                 110

Lys Val Thr Leu Lys Asp Lys Ser Ser Thr Glu Glu Lys Phe Asn Asp
        115                 120                 125

Lys Gly Lys Leu Ser Glu Lys Val Val Thr Arg Ala Asn Gly Thr Arg
130                 135                 140

Leu Glu Tyr Thr Glu Ile Gln Asn Asp Gly Ser Gly Lys Ala Lys Glu
145                 150                 155                 160

Val Leu Lys Ser Leu Thr Leu Glu Gly Thr Leu Thr Ala Asp Gly Glu
                165                 170                 175

Thr Lys Leu Thr Val Glu Ala Gly Thr Val Thr Leu Ser Lys Asn Ile
            180                 185                 190

Ser Glu Ser Gly Glu Ile Thr Val Glu Leu Lys Asp Thr Glu Thr Thr
        195                 200                 205

Pro Ala Asp Lys Lys Ser Gly Thr Trp Asp Ser Lys Thr Ser Thr Leu
210                 215                 220

Thr Ile Ser Lys Asn Ser Gln Lys Thr Lys Gln Leu Val Phe Thr Lys
225                 230                 235                 240

Glu Asn Thr Ile Thr Val Gln Lys Tyr Asn Thr Ala Gly Thr Lys Leu
                245                 250                 255

Glu Gly Ser Pro Ala Glu Ile Lys Asp Leu Glu Ala Leu Lys Ala Ala
            260                 265                 270

Leu Lys

<210> SEQ ID NO 13
<211> LENGTH: 16
<212> TYPE: PRT
<213> ORGANISM: Borrelia burgdorferi

<400> SEQUENCE: 13

Met Lys Lys Tyr Leu Leu Gly Ile Gly Leu Ile Leu Ala Leu Ile Ala
1               5                   10                  15

-continued

```
<210> SEQ ID NO 14
<211> LENGTH: 15
<212> TYPE: PRT
<213> ORGANISM: Borrelia burgdorferi

<400> SEQUENCE: 14

Met Arg Leu Leu Ile Gly Phe Ala Leu Ala Leu Ala Leu Ile Gly
1               5                   10                  15

<210> SEQ ID NO 15
<211> LENGTH: 20
<212> TYPE: PRT
<213> ORGANISM: Escherichia coli

<400> SEQUENCE: 15

Met Lys Ala Thr Lys Leu Val Leu Gly Ala Val Ile Leu Gly Ser Thr
1               5                   10                  15

Leu Leu Ala Gly
            20

<210> SEQ ID NO 16
<211> LENGTH: 21
<212> TYPE: PRT
<213> ORGANISM: Artificial Sequence
<220> FEATURE:
<223> OTHER INFORMATION: LN1 peptide linker

<400> SEQUENCE: 16

Gly Thr Ser Asp Lys Asn Asn Gly Ser Gly Ser Lys Glu Lys Asn Lys
1               5                   10                  15

Asp Gly Lys Tyr Ser
            20

<210> SEQ ID NO 17
<211> LENGTH: 11
<212> TYPE: PRT
<213> ORGANISM: Borrelia burgdorferi

<400> SEQUENCE: 17

Gly Tyr Val Leu Glu Gly Thr Leu Thr Ala Glu
1               5                   10

<210> SEQ ID NO 18
<211> LENGTH: 11
<212> TYPE: PRT
<213> ORGANISM: Borrelia afzelii

<400> SEQUENCE: 18

Asn Phe Thr Leu Glu Gly Lys Val Ala Asn Asp
1               5                   10

<210> SEQ ID NO 19
<211> LENGTH: 148
<212> TYPE: PRT
<213> ORGANISM: Artificial Sequence
<220> FEATURE:
<223> OTHER INFORMATION: B. burgdorferi OspA 126-273 with replaced
      hLFA-like sequence

<400> SEQUENCE: 19

Phe Asn Glu Lys Gly Glu Val Ser Glu Lys Ile Ile Thr Arg Ala Asp
1               5                   10                  15

Gly Thr Arg Leu Glu Tyr Thr Gly Ile Lys Ser Asp Gly Ser Gly Lys
            20                  25                  30
```

```
Ala Lys Glu Val Leu Lys Asn Phe Thr Leu Glu Gly Lys Val Ala Asn
         35                  40                  45

Asp Lys Thr Thr Leu Val Val Lys Glu Gly Thr Val Thr Leu Ser Lys
 50                  55                  60

Asn Ile Ser Lys Ser Gly Glu Val Ser Val Glu Leu Asn Asp Thr Asp
 65                  70                  75                  80

Ser Ser Ala Ala Thr Lys Lys Thr Ala Ala Trp Asn Ser Gly Thr Ser
                 85                  90                  95

Thr Leu Thr Ile Thr Val Asn Ser Lys Lys Thr Lys Asp Leu Val Phe
            100                 105                 110

Thr Lys Glu Asn Thr Ile Thr Val Gln Gln Tyr Asp Ser Asn Gly Thr
        115                 120                 125

Lys Leu Glu Gly Ser Ala Val Glu Ile Thr Lys Leu Asp Glu Ile Lys
    130                 135                 140

Asn Ala Leu Lys
145

<210> SEQ ID NO 20
<211> LENGTH: 148
<212> TYPE: PRT
<213> ORGANISM: Borrelia afzelii

<400> SEQUENCE: 20

Phe Asn Glu Lys Gly Glu Leu Ser Ala Lys Thr Met Thr Arg Glu Asn
 1               5                  10                  15

Gly Thr Lys Leu Glu Tyr Thr Glu Met Lys Ser Asp Gly Thr Gly Lys
             20                  25                  30

Ala Lys Glu Val Leu Lys Asn Phe Thr Leu Glu Gly Lys Val Ala Asn
         35                  40                  45

Asp Lys Val Thr Leu Glu Val Lys Glu Gly Thr Val Thr Leu Ser Lys
 50                  55                  60

Glu Ile Ala Lys Ser Gly Glu Val Thr Val Ala Leu Asn Asp Thr Asn
 65                  70                  75                  80

Thr Thr Gln Ala Thr Lys Lys Thr Gly Ala Trp Asp Ser Lys Thr Ser
                 85                  90                  95

Thr Leu Thr Ile Ser Val Asn Ser Lys Lys Thr Thr Gln Leu Val Phe
            100                 105                 110

Thr Lys Gln Asp Thr Ile Thr Val Gln Lys Tyr Asp Ser Ala Gly Thr
        115                 120                 125

Asn Leu Glu Gly Thr Ala Val Glu Ile Lys Thr Leu Asp Glu Leu Lys
    130                 135                 140

Asn Ala Leu Lys
145

<210> SEQ ID NO 21
<211> LENGTH: 149
<212> TYPE: PRT
<213> ORGANISM: Borrelia garinii

<400> SEQUENCE: 21

Phe Asn Asp Lys Gly Lys Leu Ser Glu Lys Val Val Thr Arg Ala Asn
 1               5                  10                  15

Gly Thr Arg Leu Glu Tyr Thr Glu Ile Lys Asn Asp Gly Ser Gly Lys
             20                  25                  30

Ala Lys Glu Val Leu Lys Gly Phe Ala Leu Glu Gly Thr Leu Thr Asp
         35                  40                  45
```

-continued

Gly Gly Glu Thr Lys Leu Thr Val Thr Glu Gly Thr Val Thr Leu Ser
            50                  55                  60

Lys Asn Ile Ser Lys Ser Gly Glu Ile Thr Val Ala Leu Asn Asp Thr
 65                  70                  75                  80

Glu Thr Thr Pro Ala Asp Lys Lys Thr Gly Glu Trp Lys Ser Asp Thr
                    85                  90                  95

Ser Thr Leu Thr Ile Ser Lys Asn Ser Gln Lys Pro Lys Gln Leu Val
                100                 105                 110

Phe Thr Lys Glu Asn Thr Ile Thr Val Gln Asn Tyr Asn Arg Ala Gly
            115                 120                 125

Asn Ala Leu Glu Gly Ser Pro Ala Glu Ile Lys Asp Leu Ala Glu Leu
        130                 135                 140

Lys Ala Ala Leu Lys
145

<210> SEQ ID NO 22
<211> LENGTH: 148
<212> TYPE: PRT
<213> ORGANISM: Borrelia bavariensis

<400> SEQUENCE: 22

Phe Asn Ala Lys Gly Glu Leu Ser Glu Lys Thr Ile Leu Arg Ala Asn
 1               5                  10                  15

Gly Thr Arg Leu Glu Tyr Thr Glu Ile Lys Ser Asp Gly Thr Gly Lys
                20                  25                  30

Ala Lys Glu Val Leu Lys Asp Phe Ala Leu Glu Gly Thr Leu Ala Ala
            35                  40                  45

Asp Lys Thr Thr Leu Lys Val Thr Glu Gly Thr Val Val Leu Ser Lys
 50                  55                  60

His Ile Pro Asn Ser Gly Glu Ile Thr Val Glu Leu Asn Asp Ser Asn
 65                  70                  75                  80

Ser Thr Gln Ala Thr Lys Lys Thr Gly Lys Trp Asp Ser Asn Thr Ser
                    85                  90                  95

Thr Leu Thr Ile Ser Val Asn Ser Lys Lys Thr Lys Asn Ile Val Phe
                100                 105                 110

Thr Lys Glu Asp Thr Ile Thr Val Gln Lys Tyr Asp Ser Ala Gly Thr
            115                 120                 125

Asn Leu Glu Gly Asn Ala Val Glu Ile Lys Thr Leu Asp Glu Leu Lys
        130                 135                 140

Asn Ala Leu Lys
145

<210> SEQ ID NO 23
<211> LENGTH: 148
<212> TYPE: PRT
<213> ORGANISM: Borrelia garinii

<400> SEQUENCE: 23

Phe Asn Glu Lys Gly Glu Ile Ser Glu Lys Thr Ile Val Arg Ala Asn
 1               5                  10                  15

Gly Thr Arg Leu Glu Tyr Thr Asp Ile Lys Ser Asp Lys Thr Gly Lys
                20                  25                  30

Ala Lys Glu Val Leu Lys Asp Phe Thr Leu Glu Gly Thr Leu Ala Ala
            35                  40                  45

Asp Gly Lys Thr Thr Leu Lys Val Thr Glu Gly Thr Val Thr Leu Ser
 50                  55                  60

```
Lys Asn Ile Ser Lys Ser Gly Glu Ile Thr Val Ala Leu Asp Asp Thr
 65                  70                  75                  80

Asp Ser Ser Gly Asn Lys Lys Ser Gly Thr Trp Asp Ser Gly Thr Ser
                 85                  90                  95

Thr Leu Thr Ile Ser Lys Asn Arg Thr Lys Thr Lys Gln Leu Val Phe
            100                 105                 110

Thr Lys Glu Asp Thr Ile Thr Val Gln Asn Tyr Asp Ser Ala Gly Thr
        115                 120                 125

Asn Leu Glu Gly Lys Ala Val Glu Ile Thr Thr Leu Lys Glu Leu Lys
    130                 135                 140

Asn Ala Leu Lys
145

<210> SEQ ID NO 24
<211> LENGTH: 149
<212> TYPE: PRT
<213> ORGANISM: Borrelia garinii

<400> SEQUENCE: 24

Phe Asn Gly Lys Gly Glu Thr Ser Glu Lys Thr Ile Val Arg Ala Asn
 1                5                  10                  15

Gly Thr Arg Leu Glu Tyr Thr Asp Ile Lys Ser Asp Gly Ser Gly Lys
             20                  25                  30

Ala Lys Glu Val Leu Lys Asp Phe Thr Leu Glu Gly Thr Leu Ala Ala
         35                  40                  45

Asp Gly Lys Thr Thr Leu Lys Val Thr Glu Gly Thr Val Val Leu Ser
     50                  55                  60

Lys Asn Ile Leu Lys Ser Gly Glu Ile Thr Ala Ala Leu Asp Asp Ser
 65                  70                  75                  80

Asp Thr Thr Arg Ala Thr Lys Lys Thr Gly Lys Trp Asp Ser Lys Thr
                 85                  90                  95

Ser Thr Leu Thr Ile Ser Val Asn Ser Gln Lys Thr Lys Asn Leu Val
            100                 105                 110

Phe Thr Lys Glu Asp Thr Ile Thr Val Gln Arg Tyr Asp Ser Ala Gly
        115                 120                 125

Thr Asn Leu Glu Gly Lys Ala Val Glu Ile Thr Thr Leu Lys Glu Leu
    130                 135                 140

Lys Asn Ala Leu Lys
145

<210> SEQ ID NO 25
<211> LENGTH: 149
<212> TYPE: PRT
<213> ORGANISM: Borrelia garinii

<400> SEQUENCE: 25

Phe Asn Asp Lys Gly Lys Leu Ser Glu Lys Val Val Thr Arg Ala Asn
 1                5                  10                  15

Gly Thr Arg Leu Glu Tyr Thr Glu Ile Gln Asn Asp Gly Ser Gly Lys
             20                  25                  30

Ala Lys Glu Val Leu Lys Ser Leu Thr Leu Glu Gly Thr Leu Thr Ala
         35                  40                  45

Asp Gly Glu Thr Lys Leu Thr Val Glu Ala Gly Thr Val Thr Leu Ser
     50                  55                  60

Lys Asn Ile Ser Glu Ser Gly Glu Ile Thr Val Glu Leu Lys Asp Thr
 65                  70                  75                  80
```

```
Glu Thr Thr Pro Ala Asp Lys Lys Ser Gly Thr Trp Asp Ser Lys Thr
                85                  90                  95

Ser Thr Leu Thr Ile Ser Lys Asn Ser Gln Lys Thr Lys Gln Leu Val
            100                 105                 110

Phe Thr Lys Glu Asn Thr Ile Thr Val Gln Lys Tyr Asn Thr Ala Gly
        115                 120                 125

Thr Lys Leu Glu Gly Ser Pro Ala Glu Ile Lys Asp Leu Glu Ala Leu
    130                 135                 140

Lys Ala Ala Leu Lys
145

<210> SEQ ID NO 26
<211> LENGTH: 1029
<212> TYPE: DNA
<213> ORGANISM: Artificial Sequence
<220> FEATURE:
<223> OTHER INFORMATION: Lip-S4D1-S3hybD1-nt

<400> SEQUENCE: 26
atgaaagcta ctaaactggt actgggcgcg gtaatcctgg ttctactct gctggcaggt       60 tgctcaagct tcaatgctaa gggcgaactg agcgaaaaaa cgatcctgcg tgcgaatggc      120
acccgtctgg aatacaccga atcaaatcc gatggtacgg gcaaagcaaa ggaagtcctg      180
aaagattttg ctctggaagg tacccctggcg ccgacaaaa ccacgctgaa ggtgacgtgc      240
ggcaccgtgg ttctgagcaa acatattccg aactctggtg aaatcaccgt tgaactgaac     300
gatagcaatt ctacgcaggc aaccaaaaag acgggcaaat gggacagtaa tacctccacg     360
ctgaccattt cagtcaactc gaaaaagacc aaaaatattg tgttcacgaa ggaagatacg     420
atcaccgttc aaaatatga ctccgcgggc accaacctgg aaggcaatgc cgtcgaaatc      480
aaaaccctgg atgaactgtg taacgccctg aagggtacta gtgacaaaaa caatggctct     540
ggtagcaaag agaaaaacaa agatggcaag tactcattca cgaaaaagg cgaagtgagc     600 gaaaaaattc tgacccgtag caatggcacc accctggaat atagccagat gaccgatgca     660
gaaaatgcaa ccaaagcagt tgaaaccctg aaaaacggta ttaaactgcc tggtaatctg     720
gttggtggta aaaccaaact gaccgttacc tgtggcaccg ttaccctgag caaaaacatt     780
agcaaaagcg gtgaaattac cgtggcactg aatgataccg aaaccacacc ggcagacaaa     840 aaaccggtg aatggaaaag cgataccagc accctgacca ttagtaaaaa tagccagaaa    900
acaaaacagc tggtgtttac caaagaaaac accattaccg tgcagaatta taaccgtgca     960
ggtaatgcac tggaaggtag tccggcagaa attaaagatc tggcagaact gtgtgcagcc   1020
ctgaaataa                                                            1029

<210> SEQ ID NO 27
<211> LENGTH: 322
<212> TYPE: PRT
<213> ORGANISM: Artificial Sequence
<220> FEATURE:
<223> OTHER INFORMATION: Lip-S4D1-S3hybD1-aa
<220> FEATURE:
<221> NAME/KEY: LIPID
<222> LOCATION: (1)..(1)

<400> SEQUENCE: 27

Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
            20                  25                  30
```

```
Thr Gly Lys Ala Lys Glu Val Leu Lys Asp Phe Ala Leu Glu Gly Thr
        35                  40                  45
Leu Ala Ala Asp Lys Thr Thr Leu Lys Val Thr Cys Gly Thr Val Val
 50                  55                  60
Leu Ser Lys His Ile Pro Asn Ser Gly Glu Ile Thr Val Glu Leu Asn
 65                  70                  75                  80
Asp Ser Asn Ser Thr Gln Ala Thr Lys Lys Thr Gly Lys Trp Asp Ser
                85                  90                  95
Asn Thr Ser Thr Leu Thr Ile Ser Val Asn Ser Lys Lys Thr Lys Asn
                100                 105                 110
Ile Val Phe Thr Lys Glu Asp Thr Ile Thr Val Gln Lys Tyr Asp Ser
                115                 120                 125
Ala Gly Thr Asn Leu Glu Gly Asn Ala Val Glu Ile Lys Thr Leu Asp
        130                 135                 140
Glu Leu Cys Asn Ala Leu Lys Gly Thr Ser Asp Lys Asn Asn Gly Ser
145                 150                 155                 160
Gly Ser Lys Glu Lys Asn Lys Asp Gly Lys Tyr Ser Phe Asn Glu Lys
                165                 170                 175
Gly Glu Val Ser Glu Lys Ile Leu Thr Arg Ser Asn Gly Thr Thr Leu
                180                 185                 190
Glu Tyr Ser Gln Met Thr Asp Ala Glu Asn Ala Thr Lys Ala Val Glu
                195                 200                 205
Thr Leu Lys Asn Gly Ile Lys Leu Pro Gly Asn Leu Val Gly Gly Lys
        210                 215                 220
Thr Lys Leu Thr Val Thr Cys Gly Thr Val Thr Leu Ser Lys Asn Ile
225                 230                 235                 240
Ser Lys Ser Gly Glu Ile Thr Val Ala Leu Asn Asp Thr Glu Thr Thr
                245                 250                 255
Pro Ala Asp Lys Lys Thr Gly Glu Trp Lys Ser Asp Thr Ser Thr Leu
                260                 265                 270
Thr Ile Ser Lys Asn Ser Gln Lys Thr Lys Gln Leu Val Phe Thr Lys
        275                 280                 285
Glu Asn Thr Ile Thr Val Gln Asn Tyr Asn Arg Ala Gly Asn Ala Leu
        290                 295                 300
Glu Gly Ser Pro Ala Glu Ile Lys Asp Leu Ala Glu Leu Cys Ala Ala
305                 310                 315                 320
Leu Lys

<210> SEQ ID NO 28
<211> LENGTH: 1020
<212> TYPE: DNA
<213> ORGANISM: Artificial Sequence
<220> FEATURE:
<223> OTHER INFORMATION: Lip-S1D1-S2D1-nt

<400> SEQUENCE: 28
atgaaagcta ctaaactggt actgggcgcg gtaatcctgg ttctactct gctggcaggt      60 tgctcaagct tcaacgaaaa gggcgaagtc agcgaaaaaa tcattacccg cgcagacggc    120
acccgcctgg aatacaccgg catcaaatcg acggcagcg gcaaagcgaa agaagttctg    180
aaaaacttta ccctggaagg caaagtcgca atgataaaa ccaccctggt ggtgaaatgc    240
ggcaccgtta cgctgagcaa aaacattagt aaatccggtg aagtctctgt ggaactgaat    300
gataccgaca gctctgcggc caccaagaaa accgcagctt ggaactcagg cacctcgacg    360
```

```
ctgaccatta cggttaatag caagaaaacc aaagatctgg tcttcacgaa agaaaacacc    420
atcacggtgc agcaatatga cagcaatggt accaaactgg aaggctccgc tgtggaaatc    480
acgaaactgg atgaaatctg taatgctctg aaaggtacta gtgacaaaaa caatggctct    540
ggtagcaaag agaaaaacaa agatggcaag tactcattca cgaaaaaagg cgaactgtcg    600
gcgaaaacga tgacgcgtga aaacggcacc aaactggaat atacggaaat gaaaagcgat    660
ggcaccggta agcgaaaga agttctgaaa aactttaccc tggaaggcaa agtcgccaat    720
gacaaagtca ccctggaagt gaatgcggc accgttacgc tgtcaaaaga aattgcaaaa    780
tcgggtgaag tgaccgttgc tctgaacgat acgaatacca cgcaagcgac caagaaaacc    840
ggcgcctggg acagcaaaac ctctacgctg accattagtg ttaatagcaa gaaaaccacg    900
cagctggtct tcaccaaaca agatacgatc accgtgcaga atacgacag tgcgggtacc    960 aacctggaag gcacggctgt tgaaatcaaa accctggacg aactgtgtaa cgccctgaaa   1020

<210> SEQ ID NO 29
<211> LENGTH: 320
<212> TYPE: PRT
<213> ORGANISM: Artificial Sequence
<220> FEATURE:
<223> OTHER INFORMATION: Lip-S1D1-S2D1-aa
<220> FEATURE:
<221> NAME/KEY: LIPID
<222> LOCATION: (1)..(1)

<400> SEQUENCE: 29

Cys Ser Ser Phe Asn Glu Lys Gly Glu Val Ser Glu Lys Ile Ile Thr
 1               5                  10                  15

Arg Ala Asp Gly Thr Arg Leu Glu Tyr Thr Gly Ile Lys Ser Asp Gly
             20                  25                  30

Ser Gly Lys Ala Lys Glu Val Leu Lys Asn Phe Thr Leu Glu Gly Lys
         35                  40                  45

Val Ala Asn Asp Lys Thr Thr Leu Val Val Lys Cys Gly Thr Val Thr
     50                  55                  60

Leu Ser Lys Asn Ile Ser Lys Ser Gly Glu Val Ser Val Glu Leu Asn
 65                  70                  75                  80

Asp Thr Asp Ser Ser Ala Ala Thr Lys Lys Thr Ala Ala Trp Asn Ser
                 85                  90                  95

Gly Thr Ser Thr Leu Thr Ile Thr Val Asn Ser Lys Lys Thr Lys Asp
            100                 105                 110

Leu Val Phe Thr Lys Glu Asn Thr Ile Thr Val Gln Gln Tyr Asp Ser
        115                 120                 125

Asn Gly Thr Lys Leu Glu Gly Ser Ala Val Glu Ile Thr Lys Leu Asp
    130                 135                 140

Glu Ile Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Glu Lys
                165                 170                 175

Gly Glu Leu Ser Ala Lys Thr Met Thr Arg Glu Asn Gly Thr Lys Leu
            180                 185                 190

Glu Tyr Thr Glu Met Lys Ser Asp Gly Thr Gly Lys Ala Lys Glu Val
        195                 200                 205

Leu Lys Asn Phe Thr Leu Glu Gly Lys Val Ala Asn Asp Lys Val Thr
    210                 215                 220

Leu Glu Val Lys Cys Gly Thr Val Thr Leu Ser Lys Glu Ile Ala Lys
225                 230                 235                 240
```

```
Ser Gly Glu Val Thr Val Ala Leu Asn Asp Thr Asn Thr Thr Gln Ala
            245                 250                 255

Thr Lys Lys Thr Gly Ala Trp Asp Ser Lys Thr Ser Thr Leu Thr Ile
        260                 265                 270

Ser Val Asn Ser Lys Lys Thr Thr Gln Leu Val Phe Thr Lys Gln Asp
        275                 280                 285

Thr Ile Thr Val Gln Lys Tyr Asp Ser Ala Gly Thr Asn Leu Glu Gly
        290                 295                 300

Thr Ala Val Glu Ile Lys Thr Leu Asp Glu Leu Cys Asn Ala Leu Lys
305                 310                 315                 320

<210> SEQ ID NO 30
<211> LENGTH: 1023
<212> TYPE: DNA
<213> ORGANISM: Artificial Sequence
<220> FEATURE:
<223> OTHER INFORMATION: Lip-S4D1-S3D1-nt

<400> SEQUENCE: 30
atgaaagcta ctaaactggt actgggcgcg gtaatcctgg gttctactct gctggcaggt      60
tgctcaagct tcaatgctaa gggcgaactg agcgaaaaaa cgatcctgcg tgcgaatggc    120
acccgtctgg aatacaccga aatcaaatcc gatggtacgg gcaaagcaaa ggaagtcctg    180
aaagattttg ctctggaagg taccctggcg gccgacaaaa ccacgctgaa ggtgacgtgc    240
ggcaccgtgg ttctgagcaa acatattccg aactctggtg aaatcaccgt tgaactgaac    300
gatagcaatt ctacgcaggc aaccaaaaag acgggcaaat gggacagtaa tacctccacg    360
ctgaccattt cagtcaactc gaaaaagacc aaaaatattg tgttcacgaa ggaagatacg    420
atcaccgttc aaaaatatga ctccgcgggc accaacctgg aaggcaatgc cgtcgaaatc    480
aaaaccctgg atgaactgtg taacgccctg aagggtacta gtgacaaaaa caatggctct    540
ggtagcaaag agaaaaacaa agatggcaag tactcattta cgataagggg caaactgtcg    600
gaaaaagtgg tcacccgcgc aaatggcacc cgcctggaat acacggaaat caaaaacgat    660
ggtagcggca agcgaagga agttctgaaa ggctttgccc tggaaggtac cctgacggat    720
ggcggtgaaa ccaaactgac cgtgacgtgc ggcaccgtta cgctgtctaa aaacattagc    780
aagtctggtg aaatcacggt cgcactgaat gataccgaaa ccacgccggc tgacaaaaag    840
accggcgaat ggaaaagtga cacctccacg ctgaccattt caaagaactc gcagaaaccg    900
aagcaactgg tcttcaccaa agaaaacacg atcaccgtgc agaactataa tcgtgccggt    960
aatgctctgg aaggctcacc ggctgaaatc aaggacctgg ctgaactgtg tgcggcactg   1020
aaa                                                                 1023

<210> SEQ ID NO 31
<211> LENGTH: 321
<212> TYPE: PRT
<213> ORGANISM: Artificial Sequence
<220> FEATURE:
<223> OTHER INFORMATION: Lip-S4D1-S3D1-aa
<220> FEATURE:
<221> NAME/KEY: LIPID
<222> LOCATION: (1)..(1)

<400> SEQUENCE: 31

Cys Ser Ser Phe Asn Ala Lys Gly Glu Leu Ser Glu Lys Thr Ile Leu
1               5                   10                  15

Arg Ala Asn Gly Thr Arg Leu Glu Tyr Thr Glu Ile Lys Ser Asp Gly
```

```
                    20                  25                  30
Thr Gly Lys Ala Lys Glu Val Leu Lys Asp Phe Ala Leu Glu Gly Thr
                35                  40                  45

Leu Ala Ala Asp Lys Thr Thr Leu Lys Val Thr Cys Gly Thr Val Val
 50                  55                  60

Leu Ser Lys His Ile Pro Asn Ser Gly Glu Ile Thr Val Glu Leu Asn
 65                  70                  75                  80

Asp Ser Asn Ser Thr Gln Ala Thr Lys Lys Thr Gly Lys Trp Asp Ser
                 85                  90                  95

Asn Thr Ser Thr Leu Thr Ile Ser Val Asn Ser Lys Lys Thr Lys Asn
                100                 105                 110

Ile Val Phe Thr Lys Glu Asp Thr Ile Thr Val Gln Lys Tyr Asp Ser
                115                 120                 125

Ala Gly Thr Asn Leu Glu Gly Asn Ala Val Glu Ile Lys Thr Leu Asp
            130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Asp Lys
                165                 170                 175

Gly Lys Leu Ser Glu Lys Val Val Thr Arg Ala Asn Gly Thr Arg Leu
                180                 185                 190

Glu Tyr Thr Glu Ile Lys Asn Asp Gly Ser Gly Lys Ala Lys Glu Val
                195                 200                 205

Leu Lys Gly Phe Ala Leu Glu Gly Thr Leu Thr Asp Gly Gly Glu Thr
            210                 215                 220

Lys Leu Thr Val Thr Cys Gly Thr Val Thr Leu Ser Lys Asn Ile Ser
225                 230                 235                 240

Lys Ser Gly Glu Ile Thr Val Ala Leu Asn Asp Thr Glu Thr Thr Pro
                245                 250                 255

Ala Asp Lys Lys Thr Gly Glu Trp Lys Ser Asp Thr Ser Thr Leu Thr
                260                 265                 270

Ile Ser Lys Asn Ser Gln Lys Pro Lys Gln Leu Val Phe Thr Lys Glu
                275                 280                 285

Asn Thr Ile Thr Val Gln Asn Tyr Asn Arg Ala Gly Asn Ala Leu Glu
                290                 295                 300

Gly Ser Pro Ala Glu Ile Lys Asp Leu Ala Glu Leu Cys Ala Ala Leu
305                 310                 315                 320

Lys

<210> SEQ ID NO 32
<211> LENGTH: 1023
<212> TYPE: DNA
<213> ORGANISM: Artificial Sequence
<220> FEATURE:
<223> OTHER INFORMATION: Lip-S5D1-S6D1-nt

<400> SEQUENCE: 32
atgaaagcta ctaaactggt actgggcgcg gtaatcctgg ttctactct gctggcaggt    60 tgctcaagct tcaacgaaaa gggcgaaatc tcagaaaaaa ccatcgtccg cgctaacggc   120
acccgcctgg aatacaccga catcaaatca gacaagaccg gtaaagcgaa ggaagttctg   180
aaagatttta cgctggaagg taccctggca gcagacggta aaaccacgct gaaggtgacc   240
tgcggtacct ttcgctgtc caaaaacatt agtaagtccg gcgaaatcac ggtcgccctg   300
gatgacaccg atagctctgg caacaaaaag agcggtacct gggattcagg cacctcgacg   360
```

```
ctgaccattt ctaaaaatcg tacgaaaacc aagcagctgg tcttcacgaa agaagatacg    420
atcaccgtgc aaaactatga cagcgcaggt accaatctgg aaggcaaagc tgtggaaatt    480
accacgctga agaactgtgt aatgctctg aaaggtacta gtgacaaaaa caatggctct    540
ggtagcaaag agaaaaacaa agatggcaag tactcattca acggcaaagg tgaaacgagc    600
gaaaagacca tcgtgcgtgc gaacggtacc cgcctggaat atacggacat aaatcggac    660 ggcagcggca agcaaagga agtcctgaaa gattttacgc tggaaggtac cctggcagca    720
gacggtaaaa ccacgctgaa ggtgacgtgc ggcaccgtgg ttctgtcaaa aaacattctg    780
aagtcgggtg aaatcaccgc agctctggat gacagcgata ccacgcgtgc tacgaaaaag    840
accggtaaat gggatagcaa gacctctacg ctgaccatta gtgtcaactc ccagaaaacg    900
aagaatctgg tgttcaccaa agaagatacg atcaccgttc aacgctatga cagtgcgggc    960
accaacctgg aaggcaaagc cgttgaaatt accacgctga agaactgtgt aatgctctg   1020 aaa                                                                1023
```

<210> SEQ ID NO 33
<211> LENGTH: 321
<212> TYPE: PRT
<213> ORGANISM: Artificial Sequence
<220> FEATURE:
<223> OTHER INFORMATION: Lip-S5D1-S6D1-aa
<220> FEATURE:
<221> NAME/KEY: LIPID
<222> LOCATION: (1)..(1)

<400> SEQUENCE: 33

```
Cys Ser Ser Phe Asn Glu Lys Gly Glu Ile Ser Glu Lys Thr Ile Val
1               5                   10                  15

Arg Ala Asn Gly Thr Arg Leu Glu Tyr Thr Asp Ile Lys Ser Asp Lys
            20                  25                  30

Thr Gly Lys Ala Lys Glu Val Leu Lys Asp Phe Thr Leu Glu Gly Thr
        35                  40                  45

Leu Ala Ala Asp Gly Lys Thr Thr Leu Lys Val Thr Cys Gly Thr Val
    50                  55                  60

Thr Leu Ser Lys Asn Ile Ser Lys Ser Gly Glu Ile Thr Val Ala Leu
65                  70                  75                  80

Asp Asp Thr Asp Ser Ser Gly Asn Lys Lys Ser Gly Thr Trp Asp Ser
                85                  90                  95

Gly Thr Ser Thr Leu Thr Ile Ser Lys Asn Arg Thr Lys Thr Lys Gln
            100                 105                 110

Leu Val Phe Thr Lys Glu Asp Thr Ile Thr Val Gln Asn Tyr Asp Ser
        115                 120                 125

Ala Gly Thr Asn Leu Glu Gly Lys Ala Val Glu Ile Thr Thr Leu Lys
    130                 135                 140

Glu Leu Cys Asn Ala Leu Lys Gly Thr Ser Asp Lys Asn Asn Gly Ser
145                 150                 155                 160

Gly Ser Lys Glu Lys Asn Lys Asp Gly Lys Tyr Ser Phe Asn Gly Lys
                165                 170                 175

Gly Glu Thr Ser Glu Lys Thr Ile Val Arg Ala Asn Gly Thr Arg Leu
            180                 185                 190

Glu Tyr Thr Asp Ile Lys Ser Asp Gly Ser Gly Lys Ala Lys Glu Val
        195                 200                 205

Leu Lys Asp Phe Thr Leu Glu Gly Thr Leu Ala Ala Asp Gly Lys Thr
    210                 215                 220
```

Thr Leu Lys Val Thr Cys Gly Thr Val Val Leu Ser Lys Asn Ile Leu
225                 230                 235                 240

Lys Ser Gly Glu Ile Thr Ala Ala Leu Asp Asp Ser Asp Thr Thr Arg
                245                 250                 255

Ala Thr Lys Thr Gly Lys Trp Asp Ser Lys Thr Ser Thr Leu Thr
            260                 265                 270

Ile Ser Val Asn Ser Gln Lys Thr Lys Asn Leu Val Phe Thr Lys Glu
                275                 280                 285

Asp Thr Ile Thr Val Gln Arg Tyr Asp Ser Ala Gly Thr Asn Leu Glu
            290                 295                 300

Gly Lys Ala Val Glu Ile Thr Thr Leu Lys Glu Leu Cys Asn Ala Leu
305                 310                 315                 320

Lys

<210> SEQ ID NO 34
<211> LENGTH: 268
<212> TYPE: PRT
<213> ORGANISM: Artificial Sequence
<220> FEATURE:
<223> OTHER INFORMATION: B. burgdorferi (strain B31, OspA serotype 1)
      aa 18-273

<400> SEQUENCE: 34

Cys Ser Ser Phe Lys Gln Asn Val Ser Ser Leu Asp Glu Lys Asn Ser
1               5                   10                  15

Val Ser Val Asp Leu Pro Gly Glu Met Lys Val Leu Val Ser Lys Glu
                20                  25                  30

Lys Asn Lys Asp Gly Lys Tyr Asp Leu Ile Ala Thr Val Asp Lys Leu
            35                  40                  45

Glu Leu Lys Gly Thr Ser Asp Lys Asn Asn Gly Ser Gly Val Leu Glu
        50                  55                  60

Gly Val Lys Ala Asp Lys Ser Lys Val Lys Leu Thr Ile Ser Asp Asp
65                  70                  75                  80

Leu Gly Gln Thr Thr Leu Glu Val Phe Lys Glu Asp Gly Lys Thr Leu
                85                  90                  95

Val Ser Lys Lys Val Thr Ser Lys Asp Lys Ser Ser Thr Glu Glu Lys
            100                 105                 110

Phe Asn Glu Lys Gly Glu Val Ser Glu Lys Ile Ile Thr Arg Ala Asp
        115                 120                 125

Gly Thr Arg Leu Glu Tyr Thr Gly Ile Lys Ser Asp Gly Ser Gly Lys
130                 135                 140

Ala Lys Glu Val Leu Lys Gly Tyr Val Leu Glu Gly Thr Leu Thr Ala
145                 150                 155                 160

Glu Lys Thr Thr Leu Val Val Lys Glu Gly Thr Val Thr Leu Ser Lys
                165                 170                 175

Asn Ile Ser Lys Ser Gly Glu Val Ser Val Glu Leu Asn Asp Thr Asp
            180                 185                 190

Ser Ser Ala Ala Thr Lys Lys Thr Ala Ala Trp Asn Ser Gly Thr Ser
        195                 200                 205

Thr Leu Thr Ile Thr Val Asn Ser Lys Lys Thr Lys Asp Leu Val Phe
210                 215                 220

Thr Lys Glu Asn Thr Ile Thr Val Gln Gln Tyr Asp Ser Asn Gly Thr
225                 230                 235                 240

Lys Leu Glu Gly Ser Ala Val Glu Ile Thr Lys Leu Asp Glu Ile Lys
                245                 250                 255

```
Asn Ala Leu Lys Leu Glu His His His His His
            260                 265

<210> SEQ ID NO 35
<211> LENGTH: 268
<212> TYPE: PRT
<213> ORGANISM: Artificial Sequence
<220> FEATURE:
<223> OTHER INFORMATION: B. afzelii (strain K78; OspA serotype 2) aa
      18-273

<400> SEQUENCE: 35

Cys Ser Ser Phe Lys Gln Asn Val Ser Ser Leu Asp Glu Lys Asn Ser
1               5                   10                  15

Ala Ser Val Asp Leu Pro Gly Glu Met Lys Val Leu Val Ser Lys Glu
            20                  25                  30

Lys Asp Lys Asp Gly Lys Tyr Ser Leu Lys Ala Thr Val Asp Lys Ile
        35                  40                  45

Glu Leu Lys Gly Thr Ser Asp Lys Asp Asn Gly Ser Gly Val Leu Glu
    50                  55                  60

Gly Thr Lys Asp Asp Lys Ser Lys Ala Lys Leu Thr Ile Ala Asp Asp
65                  70                  75                  80

Leu Ser Lys Thr Thr Phe Glu Leu Phe Lys Glu Asp Gly Lys Thr Leu
                85                  90                  95

Val Ser Arg Lys Val Ser Ser Lys Asp Lys Thr Ser Thr Asp Glu Met
            100                 105                 110

Phe Asn Glu Lys Gly Glu Leu Ser Ala Lys Thr Met Thr Arg Glu Asn
        115                 120                 125

Gly Thr Lys Leu Glu Tyr Thr Glu Met Lys Ser Asp Gly Thr Gly Lys
    130                 135                 140

Ala Lys Glu Val Leu Lys Asn Phe Thr Leu Glu Gly Lys Val Ala Asn
145                 150                 155                 160

Asp Lys Val Thr Leu Glu Val Lys Glu Gly Thr Val Thr Leu Ser Lys
                165                 170                 175

Glu Ile Ala Lys Ser Gly Glu Val Thr Val Ala Leu Asn Asp Thr Asn
            180                 185                 190

Thr Thr Gln Ala Thr Lys Lys Thr Gly Ala Trp Asp Ser Lys Thr Ser
        195                 200                 205

Thr Leu Thr Ile Ser Val Asn Ser Lys Lys Thr Thr Gln Leu Val Phe
    210                 215                 220

Thr Lys Gln Asp Thr Ile Thr Val Gln Lys Tyr Asp Ser Ala Gly Thr
225                 230                 235                 240

Asn Leu Glu Gly Thr Ala Val Glu Ile Lys Thr Leu Asp Glu Leu Lys
                245                 250                 255

Asn Ala Leu Lys Leu Glu His His His His His
            260                 265

<210> SEQ ID NO 36
<211> LENGTH: 269
<212> TYPE: PRT
<213> ORGANISM: Artificial Sequence
<220> FEATURE:
<223> OTHER INFORMATION: B. garinii (strain PBr; OspA serotype 3) aa
      18-274

<400> SEQUENCE: 36

Cys Ser Ser Phe Lys Gln Asn Val Ser Ser Leu Asp Glu Lys Asn Ser
1               5                   10                  15
```

Val Ser Val Asp Leu Pro Gly Met Lys Val Leu Val Ser Lys Glu
            20                  25                  30

Lys Asp Lys Asp Gly Lys Tyr Ser Leu Met Ala Thr Val Glu Lys Leu
            35                  40                  45

Glu Leu Lys Gly Thr Ser Asp Lys Ser Asn Gly Ser Gly Val Leu Glu
50                  55                  60

Gly Glu Lys Ala Asp Lys Ser Lys Ala Lys Leu Thr Ile Ser Gln Asp
65                  70                  75                  80

Leu Asn Gln Thr Thr Phe Glu Ile Phe Lys Glu Asp Gly Lys Thr Leu
                85                  90                  95

Val Ser Arg Lys Val Asn Ser Lys Asp Lys Ser Ser Thr Glu Glu Lys
            100                 105                 110

Phe Asn Asp Lys Gly Lys Leu Ser Glu Lys Val Val Thr Arg Ala Asn
            115                 120                 125

Gly Thr Arg Leu Glu Tyr Thr Glu Ile Lys Asn Asp Gly Ser Gly Lys
130                 135                 140

Ala Lys Glu Val Leu Lys Gly Phe Ala Leu Glu Gly Thr Leu Thr Asp
145                 150                 155                 160

Gly Gly Glu Thr Lys Leu Thr Val Thr Glu Gly Thr Val Thr Leu Ser
                165                 170                 175

Lys Asn Ile Ser Lys Ser Gly Glu Ile Thr Val Ala Leu Asn Asp Thr
            180                 185                 190

Glu Thr Thr Pro Ala Asp Lys Lys Thr Gly Glu Trp Lys Ser Asp Thr
            195                 200                 205

Ser Thr Leu Thr Ile Ser Lys Asn Ser Gln Lys Thr Lys Gln Leu Val
210                 215                 220

Phe Thr Lys Glu Asn Thr Ile Thr Val Gln Asn Tyr Asn Arg Ala Gly
225                 230                 235                 240

Asn Ala Leu Glu Gly Ser Pro Ala Glu Ile Lys Asp Leu Ala Glu Leu
                245                 250                 255

Lys Ala Ala Leu Lys Leu Glu His His His His His His
            260                 265

<210> SEQ ID NO 37
<211> LENGTH: 268
<212> TYPE: PRT
<213> ORGANISM: Artificial Sequence
<220> FEATURE:
<223> OTHER INFORMATION: B. bavariensis (strain PBi; OspA serotype 4)
      aa 18-273

<400> SEQUENCE: 37

Cys Ser Ser Phe Lys Gln Asn Val Ser Ser Leu Asp Glu Lys Asn Ser
1               5                   10                  15

Val Ser Val Asp Leu Pro Gly Glu Met Lys Val Leu Val Ser Lys Glu
            20                  25                  30

Lys Asp Lys Asp Gly Lys Tyr Ser Leu Met Ala Thr Val Asp Lys Leu
            35                  40                  45

Glu Leu Lys Gly Thr Ser Asp Lys Ser Asn Gly Ser Gly Thr Leu Glu
50                  55                  60

Gly Glu Lys Ser Asp Lys Ser Lys Ala Lys Leu Thr Ile Ser Glu Asp
65                  70                  75                  80

Leu Ser Lys Thr Thr Phe Glu Ile Phe Lys Glu Asp Gly Lys Thr Leu
                85                  90                  95

Val Ser Lys Lys Val Asn Ser Lys Asp Lys Ser Ser Ile Glu Glu Lys

-continued

```
                100                 105                 110
Phe Asn Ala Lys Gly Glu Leu Ser Glu Lys Thr Ile Leu Arg Ala Asn
            115                 120                 125
Gly Thr Arg Leu Glu Tyr Thr Glu Ile Lys Ser Asp Gly Thr Gly Lys
    130                 135                 140
Ala Lys Glu Val Leu Lys Asp Phe Ala Leu Glu Gly Thr Leu Ala Ala
145                 150                 155                 160
Asp Lys Thr Thr Leu Lys Val Thr Glu Gly Thr Val Val Leu Ser Lys
                165                 170                 175
His Ile Pro Asn Ser Gly Glu Ile Thr Val Glu Leu Asn Asp Ser Asn
            180                 185                 190
Ser Thr Gln Ala Thr Lys Lys Thr Gly Lys Trp Asp Ser Asn Thr Ser
    195                 200                 205
Thr Leu Thr Ile Ser Val Asn Ser Lys Lys Thr Lys Asn Ile Val Phe
210                 215                 220
Thr Lys Glu Asp Thr Ile Thr Val Gln Lys Tyr Asp Ser Ala Gly Thr
225                 230                 235                 240
Asn Leu Glu Gly Asn Ala Val Glu Ile Lys Thr Leu Asp Glu Leu Lys
                245                 250                 255
Asn Ala Leu Lys Leu Glu His His His His His
            260                 265

<210> SEQ ID NO 38
<211> LENGTH: 268
<212> TYPE: PRT
<213> ORGANISM: Artificial Sequence
<220> FEATURE:
<223> OTHER INFORMATION: B. garinii (strain PHei; OspA serotype 5) aa
      18-273

<400> SEQUENCE: 38

Cys Ser Ser Phe Lys Gln Asn Val Ser Leu Asp Glu Lys Asn Ser
1               5                   10                  15
Val Ser Val Asp Leu Pro Gly Gly Met Lys Val Leu Val Ser Lys Glu
                20                  25                  30
Lys Asp Lys Asp Gly Lys Tyr Ser Leu Met Ala Thr Val Glu Lys Leu
            35                  40                  45
Glu Leu Lys Gly Thr Ser Asp Lys Asn Asn Gly Ser Gly Thr Leu Glu
    50                  55                  60
Gly Glu Lys Thr Asp Lys Ser Lys Val Lys Leu Thr Ile Ala Glu Asp
65                  70                  75                  80
Leu Ser Lys Thr Thr Phe Glu Ile Phe Lys Glu Asp Gly Lys Thr Leu
                85                  90                  95
Val Ser Lys Lys Val Thr Leu Lys Asp Lys Ser Ser Thr Glu Glu Lys
                100                 105                 110
Phe Asn Glu Lys Gly Glu Ile Ser Glu Lys Thr Ile Val Arg Ala Asn
            115                 120                 125
Gly Thr Arg Leu Glu Tyr Thr Asp Ile Lys Ser Asp Lys Thr Gly Lys
    130                 135                 140
Ala Lys Glu Val Leu Lys Asp Phe Thr Leu Glu Gly Thr Leu Ala Ala
145                 150                 155                 160
Asp Gly Lys Thr Thr Leu Lys Val Thr Glu Gly Thr Val Thr Leu Ser
                165                 170                 175
Lys Asn Ile Ser Lys Ser Gly Glu Ile Thr Val Ala Leu Asp Asp Thr
            180                 185                 190
```

```
Asp Ser Ser Gly Asn Lys Lys Ser Gly Thr Trp Asp Ser Gly Thr Ser
            195                 200                 205

Thr Leu Thr Ile Ser Lys Asn Arg Thr Lys Thr Lys Gln Leu Val Phe
        210                 215                 220

Thr Lys Glu Asp Thr Ile Thr Val Gln Asn Tyr Asp Ser Ala Gly Thr
225                 230                 235                 240

Asn Leu Glu Gly Lys Ala Val Glu Ile Thr Thr Leu Lys Glu Leu Lys
                245                 250                 255

Asn Ala Leu Lys Leu Glu His His His His His His
            260                 265
```

<210> SEQ ID NO 39
<211> LENGTH: 269
<212> TYPE: PRT
<213> ORGANISM: Artificial Sequence
<220> FEATURE:
<223> OTHER INFORMATION: B. garinii (strain DK29; OspA serotype 6) aa 18-274

<400> SEQUENCE: 39

```
Cys Ser Ser Phe Lys Gln Asn Val Ser Ser Leu Asp Glu Lys Asn Ser
1               5                   10                  15

Val Ser Val Asp Leu Pro Gly Gly Met Thr Val Leu Val Ser Lys Glu
                20                  25                  30

Lys Asp Lys Asp Gly Lys Tyr Ser Leu Glu Ala Thr Val Asp Lys Leu
            35                  40                  45

Glu Leu Lys Gly Thr Ser Asp Lys Asn Asn Gly Ser Gly Thr Leu Glu
        50                  55                  60

Gly Glu Lys Thr Asp Lys Ser Lys Val Lys Ser Thr Ile Ala Asp Asp
65                  70                  75                  80

Leu Ser Gln Thr Lys Phe Glu Ile Phe Lys Glu Asp Gly Lys Thr Leu
                85                  90                  95

Val Ser Lys Lys Val Thr Leu Lys Asp Lys Ser Ser Thr Glu Glu Lys
            100                 105                 110

Phe Asn Gly Lys Gly Glu Thr Ser Glu Lys Thr Ile Val Arg Ala Asn
        115                 120                 125

Gly Thr Arg Leu Glu Tyr Thr Asp Ile Lys Ser Asp Gly Ser Gly Lys
130                 135                 140

Ala Lys Glu Val Leu Lys Asp Phe Thr Leu Glu Gly Thr Leu Ala Ala
145                 150                 155                 160

Asp Gly Lys Thr Thr Leu Lys Val Thr Glu Gly Thr Val Val Leu Ser
                165                 170                 175

Lys Asn Ile Leu Lys Ser Gly Glu Ile Thr Ala Ala Leu Asp Asp Ser
            180                 185                 190

Asp Thr Thr Arg Ala Thr Lys Lys Thr Gly Lys Trp Asp Ser Lys Thr
        195                 200                 205

Ser Thr Leu Thr Ile Ser Val Asn Ser Gln Lys Thr Lys Asn Leu Val
130                 215                 220

Phe Thr Lys Glu Asp Thr Ile Thr Val Gln Arg Tyr Asp Ser Ala Gly
225                 230                 235                 240

Thr Asn Leu Glu Gly Lys Ala Val Glu Ile Thr Thr Leu Lys Glu Leu
                245                 250                 255

Lys Asn Ala Leu Lys Leu Glu His His His His His His
            260                 265
```

<210> SEQ ID NO 40

<211> LENGTH: 278
<212> TYPE: PRT
<213> ORGANISM: Artificial Sequence
<220> FEATURE:
<223> OTHER INFORMATION: Chimeric OspA Serotype1/Serotype2, N-terminal
      lipidation

<400> SEQUENCE: 40

Met Arg Leu Leu Ile Gly Phe Ala Le

Gly Gly Met Lys Val Leu Val Ser Lys Glu Lys Asp Lys Asn Gly Lys
            35                  40                  45

Tyr Ser Leu Met Ala Thr Val Glu Lys Leu Glu Leu Lys Gly Thr Ser
    50                  55                  60

Asp Lys Asn Asn Gly Ser Gly Thr Leu Glu Gly Glu Lys Thr Asn Lys
65                  70                  75                  80

Ser Lys Val Lys Leu Thr Ile Ala Glu Asp Leu Ser Lys Thr Thr Phe
                85                  90                  95

Glu Ile Phe Lys Glu Asp Gly Lys Thr Leu Val Ser Lys Lys Val Thr
                100                 105                 110

Leu Lys Asp Lys Ser Ser Thr Glu Glu Lys Phe Asn Glu Lys Gly Glu
                115                 120                 125

Ile Ser Glu Lys Thr Ile Val Met Ala Asn Gly Thr Arg Leu Glu Tyr
            130                 135                 140

Thr Asp Ile Lys Ser Asp Lys Thr Gly Lys Ala Lys Tyr Val Leu Lys
145                 150                 155                 160

Asp Phe Thr Leu Glu Gly Thr Leu Ala Ala Asp Gly Lys Thr Thr Leu
                165                 170                 175

Lys Val Thr Glu Gly Thr Val Thr Leu Ser Met Asn Ile Ser Lys Ser
                180                 185                 190

Gly Glu Ile Thr Val Ala Leu Asp Asp Thr Asp Ser Ser Gly Asn Lys
            195                 200                 205

Lys Ser Gly Thr Trp Asp Ser Asp Thr Ser Thr Leu Thr Ile Ser Lys
            210                 215                 220

Asn Ser Gln Lys Thr Lys Gln Leu Val Phe Thr Lys Glu Asn Thr Ile
225                 230                 235                 240

Thr Val Gln Asn Tyr Asn Arg Ala Gly Asn Ala Leu Glu Gly Ser Pro
                245                 250                 255

Ala Glu Ile Lys Asp Leu Ala Glu Leu Lys Ala Ala Leu Lys Leu Glu
                260                 265                 270

His His His His His His
            275

<210> SEQ ID NO 42
<211> LENGTH: 279
<212> TYPE: PRT
<213> ORGANISM: Artificial Sequence
<220> FEATURE:
<223> OTHER INFORMATION: Chimeric OspA Serotype6/Serotype4, N-terminal
      lipidation

<400> SEQUENCE: 42

Met Arg Leu Leu Ile Gly Phe Ala Leu Ala Leu Ala Leu Ile Gly Cys
1               5                   10                  15

Ala Gln Lys Gly Ala Glu Ser

```
                100                 105                 110
Leu Lys Asp Lys Ser Ser Thr Glu Glu Lys Phe Asn Glu Lys Gly Glu
            115                 120                 125

Thr Ser Glu Lys Thr Ile Val Met Ala Asn Gly Thr Arg Leu Glu Tyr
        130                 135                 140

Thr Asp Ile Lys Ser Asp Gly Ser Gly Lys Ala Lys Tyr Val Leu Lys
145                 150                 155                 160

Asp Phe Thr Leu Glu Gly Thr Leu Ala Ala Asp Gly Lys Thr Thr Leu
                165                 170                 175

Lys Val Thr Glu Gly Thr Val Val Leu Ser Met Asn Ile Leu Lys Ser
            180                 185                 190

Gly Glu Ile Thr Val Ala Leu Asp Asp Ser Asp Thr Thr Gln Ala Thr
        195                 200                 205

Lys Lys Thr Gly Lys Trp Asp Ser Asn Thr Ser Thr Leu Thr Ile Ser
210                 215                 220

Val Asn Ser Lys Lys Thr Lys Asn Ile Val Phe Thr Lys Glu Asp Thr
225                 230                 235                 240

Ile Thr Val Gln Lys Tyr Asp Ser Ala Gly Thr Asn Leu Glu Gly Asn
                245                 250                 255

Ala Val Glu Ile Lys Thr Leu Asp Glu Leu Lys Asn Ala Leu Lys Leu
            260                 265                 270

Glu His His His His His His
        275

<210> SEQ ID NO 43
<211> LENGTH: 148
<212> TYPE: PRT
<213> ORGANISM: Artificial Sequence
<220> FEATURE:
<223> OTHER INFORMATION: S1D1

<400> SEQUENCE: 43

Phe Asn Glu Lys Gly Glu Val Ser Glu Lys Ile Ile Thr Arg Ala Asp
1               5                   10                  15

Gly Thr Arg Leu Glu Tyr Thr Gly Ile Lys Ser Asp Gly Ser Gly Lys
            20                  25                  30

Ala Lys Glu Val Leu Lys Asn Phe Thr Leu Glu Gly Lys Val Ala Asn
        35                  40                  45

Asp Lys Thr Thr Leu Val Val Lys Cys Gly Thr Val Thr Leu Ser Lys
    50                  55                  60

Asn Ile Ser Lys Ser Gly Glu Val Ser Val Glu Leu Asn Asp Thr Asp
65                  70                  75                  80

Ser Ser Ala Ala Thr Lys Lys Thr Ala Ala Trp Asn Ser Gly Thr Ser
                85                  90                  95

Thr Leu Thr Ile Thr Val Asn Ser Lys Lys Thr Lys Asp Leu Val Phe
            100                 105                 110

Thr Lys Glu Asn Thr Ile Thr Val Gln Gln Tyr Asp Ser Asn Gly Thr
        115                 120                 125

Lys Leu Glu Gly Ser Ala Val Glu Ile Thr Leu Asp Glu Ile Cys
    130                 135                 140

Asn Ala Leu Lys
145

<210> SEQ ID NO 44
<211> LENGTH: 148
<212> TYPE: PRT
```

<213> ORGANISM: Artificial Sequence
<220> FEATURE:
<223> OTHER INFORMATION: S2D1

<400> SEQUENCE: 44

```
Phe Asn Glu Lys Gly Glu Leu Ser Ala Lys Thr Met Thr Arg Glu Asn
1               5                   10                  15

Gly Thr Lys Leu Glu Tyr Thr Glu Met Lys Ser Asp Gly Thr Gly Lys
            20                  25                  30

Ala Lys Glu Val Leu Lys Asn Phe Thr Leu Glu Gly Lys Val Ala Asn
        35                  40                  45

Asp Lys Val Thr Leu Glu Val Lys Cys Gly Thr Val Thr Leu Ser Lys
    50                  55                  60

Glu Ile Ala Lys Ser Gly Glu Val Thr Val Ala Leu Asn Asp Thr Asn
65                  70                  75                  80

Thr Thr Gln Ala Thr Lys Lys Thr Gly Ala Trp Asp Ser Lys Thr Ser
                85                  90                  95

Thr Leu Thr Ile Ser Val Asn Ser Lys Lys Thr Thr Gln Leu Val Phe
            100                 105                 110

Thr Lys Gln Asp Thr Ile Thr Val Gln Lys Tyr Asp Ser Ala Gly Thr
        115                 120                 125

Asn Leu Glu Gly Thr Ala Val Glu Ile Lys Thr Leu Asp Glu Leu Cys
    130                 135                 140

Asn Ala Leu Lys
145
```

<210> SEQ ID NO 45
<211> LENGTH: 149
<212> TYPE: PRT
<213> ORGANISM: Artificial Sequence
<220> FEATURE:
<223> OTHER INFORMATION: S3D1

<400> SEQUENCE: 45

```
Phe Asn Asp Lys Gly Lys Leu Ser Glu Lys Val Val Thr Arg Ala Asn
1               5                   10                  15

Gly Thr Arg Leu Glu Tyr Thr Glu Ile Lys Asn Asp Gly Ser Gly Lys
            20                  25                  30

Ala Lys Glu Val Leu Lys Gly Phe Ala Leu Glu Gly Thr Leu Thr Asp
        35                  40                  45

Gly Gly Glu Thr Lys Leu Thr Val Thr Cys Gly Thr Val Thr Leu Ser
    50                  55                  60

Lys Asn Ile Ser Lys Ser Gly Glu Ile Thr Val Ala Leu Asn Asp Thr
65                  70                  75                  80

Glu Thr Thr Pro Ala Asp Lys Lys Thr Gly Glu Trp Lys Ser Asp Thr
                85                  90                  95

Ser Thr Leu Thr Ile Ser Lys Asn Ser Gln Lys Thr Lys Gln Leu Val
            100                 105                 110

Phe Thr Lys Glu Asn Thr Ile Thr Val Gln Asn Tyr Asn Arg Ala Gly
        115                 120                 125

Asn Ala Leu Glu Gly Ser Pro Ala Glu Ile Lys Asp Leu Ala Glu Leu
    130                 135                 140

Cys Ala Ala Leu Lys
145
```

<210> SEQ ID NO 46
<211> LENGTH: 148

<212> TYPE: PRT
<213> ORGANISM: Artificial Sequence
<220> FEATURE:
<223> OTHER INFORMATION: S4D1

<400> SEQUENCE: 46

Phe Asn Ala Lys Gly Glu Leu Ser Glu Lys Thr Ile Leu Arg Ala Asn
1               5                   10                  15

Gly Thr Arg Leu Glu Tyr Thr Glu Ile Lys Ser Asp Gly Thr Gly Lys
            20                  25                  30

Ala Lys Glu Val Leu Lys Asp Phe Ala Leu Glu Gly Thr Leu Ala Ala
        35                  40                  45

Asp Lys Thr Thr Leu Lys Val Thr Cys Gly Thr Val Val Leu Ser Lys
    50                  55                  60

His Ile Pro Asn Ser Gly Glu Ile Thr Val Glu Leu Asn Asp Ser Asn
65                  70                  75                  80

Ser Thr Gln Ala Thr Lys Lys Thr Gly Lys Trp Asp Ser Asn Thr Ser
                85                  90                  95

Thr Leu Thr Ile Ser Val Asn Ser Lys Thr Lys Asn Ile Val Phe
            100                 105                 110

Thr Lys Glu Asp Thr Ile Thr Val Gln Lys Tyr Asp Ser Ala Gly Thr
        115                 120                 125

Asn Leu Glu Gly Asn Ala Val Glu Ile Lys Thr Leu Asp Glu Leu Cys
    130                 135                 140

Asn Ala Leu Lys
145

<210> SEQ ID NO 47
<211> LENGTH: 148
<212> TYPE: PRT
<213> ORGANISM: Artificial Sequence
<220> FEATURE:
<223> OTHER INFORMATION: S5D1

<400> SEQUENCE: 47

Phe Asn Glu Lys Gly Glu Ile Ser Glu Lys Thr Ile Val Arg Ala Asn
1               5                   10                  15

Gly Thr Arg Leu Glu Tyr Thr Asp Ile Lys Ser Asp Lys Thr Gly Lys
            20                  25                  30

Ala Lys Glu Val Leu Lys Asp Phe Thr Leu Glu Gly Thr Leu Ala Ala
        35                  40                  45

Asp Gly Lys Thr Thr Leu Lys Val Thr Cys Gly Thr Val Thr Leu Ser
    50                  55                  60

Lys Asn Ile Ser Lys Ser Gly Glu Ile Thr Val Ala Leu Asp Asp Thr
65                  70                  75                  80

Asp Ser Ser Gly Asn Lys Lys Ser Gly Trp Asp Ser Gly Thr Ser
                85                  90                  95

Thr Leu Thr Ile Ser Lys Asn Arg Thr Lys Thr Lys Gln Leu Val Phe
            100                 105                 110

Thr Lys Glu Asp Thr Ile Thr Val Gln Asn Tyr Asp Ser Ala Gly Thr
        115                 120                 125

Asn Leu Glu Gly Lys Ala Val Glu Ile Thr Thr Leu Lys Glu Leu Cys
    130                 135                 140

Asn Ala Leu Lys
145

<210> SEQ ID NO 48

<211> LENGTH: 149
<212> TYPE: PRT
<213> ORGANISM: Artificial Sequence
<220> FEATURE:
<223> OTHER INFORMATION: S6D1

<400> SEQUENCE: 48

```
Phe Asn Gly Lys Gly Glu Thr Ser Glu Lys Thr Ile Val Arg Ala Asn
1               5                   10                  15
Gly Thr Arg Leu Glu Tyr Thr Asp Ile Lys Ser Asp Gly Ser Gly Lys
            20                  25                  30
Ala Lys Glu Val Leu Lys Asp Phe Thr Leu Glu Gly Thr Leu Ala Ala
        35                  40                  45
Asp Gly Lys Thr Thr Leu Lys Val Thr Cys Gly Thr Val Val Leu Ser
    50                  55                  60
Lys Asn Ile Leu Lys Ser Gly Glu Ile Thr Ala Ala Leu Asp Asp Ser
65                  70                  75                  80
Asp Thr Thr Arg Ala Thr Lys Lys Thr Gly Lys Trp Asp Ser Lys Thr
                85                  90                  95
Ser Thr Leu Thr Ile Ser Val Asn Ser Gln Lys Thr Lys Asn Leu Val
            100                 105                 110
Phe Thr Lys Glu Asp Thr Ile Thr Val Gln Arg Tyr Asp Ser Ala Gly
        115                 120                 125
Thr Asn Leu Glu Gly Lys Ala Val Glu Ile Thr Thr Leu Lys Glu Leu
    130                 135                 140
Cys Asn Ala Leu Lys
145
```

<210> SEQ ID NO 49
<211> LENGTH: 150
<212> TYPE: PRT
<213> ORGANISM: Artificial Sequence
<220> FEATURE:
<223> OTHER INFORMATION: S3HYBD1 (BVA)

<400> SEQUENCE: 49

```
Phe Asn Glu Lys Gly Glu Val Ser Glu Lys Ile Leu Thr Arg Ser Asn
1               5                   10                  15
Gly Thr Thr Leu Glu Tyr Ser Gln Met Thr Asp Ala Glu Asn Ala Thr
            20                  25                  30
Lys Ala Val Glu Thr Leu Lys Asn Gly Ile Lys Leu Pro Gly Asn Leu
        35                  40                  45
Val Gly Gly Lys Thr Lys Leu Thr Val Thr Cys Gly Thr Val Thr Leu
    50                  55                  60
Ser Lys Asn Ile Ser Lys Ser Gly Glu Ile Thr Val Ala Leu Asn Asp
65                  70                  75                  80
Thr Glu Thr Thr Pro Ala Asp Lys Lys Thr Gly Glu Trp Lys Ser Asp
                85                  90                  95
Thr Ser Thr Leu Thr Ile Ser Lys Asn Ser Gln Lys Thr Lys Gln Leu
            100                 105                 110
Val Phe Thr Lys Glu Asn Thr Ile Thr Val Gln Asn Tyr Asn Arg Ala
        115                 120                 125
Gly Asn Ala Leu Glu Gly Ser Pro Ala Glu Ile Lys Asp Leu Ala Glu
    130                 135                 140
Leu Cys Ala Ala Leu Lys
145                 150
```

```
<210> SEQ ID NO 50
<211> LENGTH: 150
<212> TYPE: PRT
<213> ORGANISM: Artificial Sequence
<220> FEATURE:
<223> OTHER INFORMATION: BVAD1

<400> SEQUENCE: 50

Phe Asn Glu Lys Gly Glu Val Ser Glu Lys Ile Leu Thr Arg Ser Asn
1               5                   10                  15

Gly Thr Thr Leu Glu Tyr Ser Gln Met Thr Asp Ala Glu Asn Ala Thr
            20                  25                  30

Lys Ala Val Glu Thr Leu Lys Asn Gly Ile Lys Leu Pro Gly Asn Leu
        35                  40                  45

Val Gly Gly Lys Thr Thr Leu Lys Ile Thr Cys Gly Thr Val Thr Leu
    50                  55                  60

Ser Lys His Ile Ala Lys Ser Gly Glu Val Thr Val Glu Ile Asn Asp
65                  70                  75                  80

Thr Ser Ser Thr Pro Asn Thr Lys Thr Gly Lys Trp Asp Ala Arg
                85                  90                  95

Asn Ser Thr Leu Thr Ile Ile Val Asp Ser Lys Asn Lys Thr Lys Leu
            100                 105                 110

Val Phe Thr Lys Gln Asp Thr Ile Thr Val Gln Ser Tyr Asn Pro Ala
        115                 120                 125

Gly Asn Lys Leu Glu Gly Thr Ala Val Glu Ile Lys Thr Leu Gln Glu
    130                 135                 140

Leu Cys Asn Ala Leu Lys
145                 150

<210> SEQ ID NO 51
<211> LENGTH: 148
<212> TYPE: PRT
<213> ORGANISM: Artificial Sequence
<220> FEATURE:
<223> OTHER INFORMATION: S3HYBD1 (BSP)

<400> SEQUENCE: 51

Phe Asn Glu Lys Gly Glu Leu Ser Glu Lys Thr Leu Val Arg Ala Asn
1               5                   10                  15

Gly Thr Lys Leu Glu Tyr Thr Glu Ile Lys Ser Asp Gly Thr Gly Lys
            20                  25                  30

Ala Lys Glu Val Leu Lys Asp Phe Thr Leu Glu Gly Thr Leu Ala Asn
        35                  40                  45

Glu Lys Thr Lys Leu Thr Val Thr Cys Gly Thr Val Thr Leu Ser Lys
    50                  55                  60

Asn Ile Ser Lys Ser Gly Glu Ile Thr Val Ala Leu Asn Asp Thr Glu
65                  70                  75                  80

Thr Thr Pro Ala Asp Lys Lys Thr Gly Glu Trp Lys Ser Asp Thr Ser
                85                  90                  95

Thr Leu Thr Ile Ser Lys Asn Ser Gln Lys Thr Lys Gln Leu Val Phe
            100                 105                 110

Thr Lys Glu Asn Thr Ile Thr Val Gln Asn Tyr Asn Arg Ala Gly Asn
        115                 120                 125

Ala Leu Glu Gly Ser Pro Ala Glu Ile Lys Asp Leu Ala Glu Leu Cys
    130                 135                 140

Ala Ala Leu Lys
145
```

<210> SEQ ID NO 52
<211> LENGTH: 148
<212> TYPE: PRT
<213> ORGANISM: Artificial Sequence
<220> FEATURE:
<223> OTHER INFORMATION: MSPD1

<400> SEQUENCE: 52

Phe Asn Glu Lys Gly Glu Leu Ser Lys Thr Leu Val Arg Ala Asn
1               5                   10                  15

Gly Thr Lys Leu Glu Tyr Thr Glu Ile Lys Ser Asp Gly Thr Gly Lys
            20                  25                  30

Ala Lys Glu Val Leu Lys Asp Phe Thr Leu Glu Gly Thr Leu Ala Asn
        35                  40                  45

Glu Lys Ala Thr Leu Thr Val Lys Cys Gly Thr Val Thr Leu Ser Lys
    50                  55                  60

Asn Ile Asp Lys Ser Gly Glu Val Thr Val Ala Leu Asn Asp Thr Asp
65                  70                  75                  80

Ser Thr Ala Ala Thr Lys Lys Thr Gly Ala Trp Asp Ser Lys Thr Ser
                85                  90                  95

Thr Leu Thr Ile Thr Val Asn Ser Lys Lys Thr Lys Asp Leu Val Phe
            100                 105                 110

Thr Lys Gln Asp Thr Ile Thr Val Gln Lys Tyr Asp Ser Ala Gly Thr
        115                 120                 125

Thr Leu Glu Gly Ser Ala Val Glu Ile Lys Thr Leu Asp Glu Leu Cys
    130                 135                 140

Asn Ala Leu Lys
145

<210> SEQ ID NO 53
<211> LENGTH: 21
<212> TYPE: DNA
<213> ORGANISM: Artificial Sequence
<220> FEATURE:
<223> OTHER INFORMATION: Forward primer for the 16S-23S intergenic
      spacer

<400> SEQUENCE: 53
gtatgtttag tgaggggggt g                                         21

<210> SEQ ID NO 54
<211> LENGTH: 22
<212> TYPE: DNA
<213> ORGANISM: Artificial Sequence
<220> FEATURE:
<223> OTHER INFORMATION: Reverse primer for the 16S-23S intergenic
      spacer

<400> SEQUENCE: 54
ggatcatagc tcaggtggtt ag                                        22

<210> SEQ ID NO 55
<211> LENGTH: 22
<212> TYPE: DNA
<213> ORGANISM: Artificial Sequence
<220> FEATURE:
<223> OTHER INFORMATION: Forward nested primer for the 16S-23S
      intergenic spacer

<400> SEQUENCE: 55 agggggggtga agtcgtaaca ag                                       22

<210> SEQ ID NO 56
<211> LENGTH: 22
<212> TYPE: DNA
<213> ORGANISM: Artificial Sequence
<220> FEATURE:
<223> OTHER INFORMATION: Reverse nested primer for the 16S-23S
      intergenic spacer

<400> SEQUENCE: 56
gtctgataaa cctgaggtcg ga                                              22

<210> SEQ ID NO 57
<211> LENGTH: 20
<212> TYPE: DNA
<213> ORGANISM: Artificial Sequence
<220> FEATURE:
<223> OTHER INFORMATION: Forward primer for the RecA gene of Borrelia

<400> SEQUENCE: 57
catgctcttg atcctgttta                                                 20

<210> SEQ ID NO 58
<211> LENGTH: 20
<212> TYPE: DNA
<213> ORGANISM: Artificial Sequence
<220> FEATURE:
<223> OTHER INFORMATION: Reverse primer for the RecA gene of Borrelia

<400> SEQUENCE: 58
cccatttctc catctatctc                                                 20

<210> SEQ ID NO 59
<211> LENGTH: 25
<212> TYPE: PRT
<213> ORGANISM: Artificial Sequence
<220> FEATURE:
<223> OTHER INFORMATION: 25-mer peptide from the Invariable Region 6
      (IR6) of VlsE

<400> SEQUENCE: 59

Met Lys Lys Asp Asp Gln Ile Ala Ala Ala Met Val Leu Arg Gly Met
1               5                   10                  15

Ala Lys Asp Gly Gln Phe Ala Leu Lys
            20                  25

<210> SEQ ID NO 60
<211> LENGTH: 36
<212> TYPE: PRT
<213> ORGANISM: Artificial Sequence
<220> FEATURE:
<223> OTHER INFORMATION: Mouse cathelin

<400> SEQUENCE: 60

Arg Leu Ala Gly Leu Leu Arg Lys Gly Gly Glu Lys Ile Gly Glu Lys
1               5                   10                  15

Leu Lys Lys Ile Gly Gln Lys Ile Lys Asn Phe Phe Gln Lys Leu Val
            20                  25                  30

Pro Gln Pro Glu
        35

<210> SEQ ID NO 61
<211> LENGTH: 11
<212> TYPE: PRT
<213> ORGANISM: Artificial Sequence
<220> FEATURE:

```
<223> OTHER INFORMATION: KLK peptide

<400> SEQUENCE: 61

Lys Leu Lys Leu Leu Leu Leu Leu Lys Leu Lys
1               5                   10

<210> SEQ ID NO 62
<211> LENGTH: 4
<212> TYPE: PRT
<213> ORGANISM: Artificial Sequence
<220> FEATURE:
<223> OTHER INFORMATION: N-terminal peptide for lipidation

<400> SEQUENCE: 62

Cys Lys Gln Asn
1

<210> SEQ ID NO 63
<211> LENGTH: 26
<212> TYPE: DNA
<213> ORGANISM: Artificial Sequence
<220> FEATURE:
<223> OTHER INFORMATION: 5'-(dIdC)13-3'
<220> FEATURE:
<221> NAME/KEY: misc_feature
<222> LOCATION: (1)..(26)
<223> OTHER INFORMATION: n=inosine

<400> SEQUENCE: 63 ncncncnc ncncncnc ncncnc                                           26

<210> SEQ ID NO 64
<211> LENGTH: 8
<212> TYPE: PRT
<213> ORGANISM: Artificial Sequence
<220> FEATURE:
<223> OTHER INFORMATION: C-terminal His tag

<400> SEQUENCE: 64

Leu Glu His His His His His His
1               5

<210> SEQ ID NO 65
<211> LENGTH: 4
<212> TYPE: PRT
<213> ORGANISM: Artificial Sequence
<220> FEATURE:
<223> OTHER INFORMATION: N-terminal CSSF for addition of lipids

<400> SEQUENCE: 65

Cys Ser Ser Phe
1
```